(12) United States Patent
Rezania et al.

(10) Patent No.: US 9,234,178 B2
(45) Date of Patent: Jan. 12, 2016

(54) DIFFERENTIATION OF HUMAN PLURIPOTENT STEM CELLS

(75) Inventors: Alireza Rezania, Skillman, NJ (US); Benjamin Fryer, Skillman, NJ (US)

(73) Assignee: Janssen Biotech, Inc., Horsham, PA (US)

( * ) Notice: Subject to any disclaimer, the term of this patent is extended or adjusted under 35 U.S.C. 154(b) by 1104 days.

(21) Appl. No.: 12/604,457

(22) Filed: Oct. 23, 2009

(65) Prior Publication Data

US 2010/0112693 A1 May 6, 2010

Related U.S. Application Data

(60) Provisional application No. 61/110,287, filed on Oct. 31, 2008.

(51) Int. Cl.
*C12N 5/071* (2010.01)

(52) U.S. Cl.
CPC ........ *C12N 5/0676* (2013.01); *C12N 2501/115* (2013.01); *C12N 2501/117* (2013.01); *C12N 2501/155* (2013.01); *C12N 2501/16* (2013.01); *C12N 2501/39* (2013.01); *C12N 2501/405* (2013.01); *C12N 2501/41* (2013.01); *C12N 2501/70* (2013.01); *C12N 2501/998* (2013.01); *C12N 2506/02* (2013.01)

(58) Field of Classification Search
None
See application file for complete search history.

(56) References Cited

U.S. PATENT DOCUMENTS

| | | |
|---|---|---|
| 3,935,067 A | 1/1976 | Thayer |
| 4,557,264 A | 12/1985 | Hinsch |
| 4,737,578 A | 4/1988 | Evans et al. |
| 5,215,893 A | 6/1993 | Mason et al. |
| 5,449,383 A | 9/1995 | Chatelier et al. |
| 5,525,488 A | 6/1996 | Mason et al. |
| 5,567,612 A | 10/1996 | Vacanti et al. |
| 5,665,568 A | 9/1997 | Mason et al. |
| 5,716,810 A | 2/1998 | Mason et al. |
| 5,718,922 A | 2/1998 | Herrero-Vanrell |
| 5,759,830 A | 6/1998 | Vacanti et al. |
| 5,770,417 A | 6/1998 | Vacanti et al. |
| 5,834,308 A | 11/1998 | Peck et al. |
| 5,843,780 A | 12/1998 | Thomson |
| 5,908,782 A | 6/1999 | Marshak et al. |
| 5,914,262 A | 6/1999 | MacMichael et al. |
| 5,942,435 A | 8/1999 | Wheeler |
| 6,001,647 A | 12/1999 | Peck et al. |
| 6,022,743 A | 2/2000 | Naughton et al. |
| 6,087,113 A | 7/2000 | Caplan et al. |
| 6,200,806 B1 | 3/2001 | Thomson |
| 6,261,549 B1 | 7/2001 | Fernandez et al. |
| 6,281,012 B1 | 8/2001 | McIntosh et al. |
| 6,306,424 B1 | 10/2001 | Vyakarnam et al. |
| 6,328,960 B1 | 12/2001 | McIntosh et al. |
| 6,331,298 B1 | 12/2001 | Ferguson et al. |
| 6,333,029 B1 | 12/2001 | Vyakarnam et al. |
| 6,365,149 B2 | 4/2002 | Vyakarnam et al. |
| 6,436,704 B1 | 8/2002 | Roberts et al. |
| 6,458,589 B1 | 10/2002 | Rambhatla et al. |
| 6,458,593 B1 | 10/2002 | Musick et al. |
| 6,509,369 B2 | 1/2003 | Scott et al. |
| 6,521,427 B1 | 2/2003 | Evans |
| 6,534,084 B1 | 3/2003 | Vyakarnam et al. |
| 6,599,323 B2 | 7/2003 | Melican et al. |
| 6,617,152 B2 | 9/2003 | Bryhan et al. |
| 6,626,950 B2 | 9/2003 | Brown et al. |
| 6,642,048 B2 | 11/2003 | Xu et al. |
| 6,656,488 B2 | 12/2003 | Yi et al. |
| 6,670,127 B2 | 12/2003 | Evans |
| 6,703,017 B1 | 3/2004 | Peck et al. |
| 6,793,945 B2 | 9/2004 | Bathurst et al. |
| 6,800,480 B1 | 10/2004 | Bodnar et al. |
| 6,815,203 B1 | 11/2004 | Bonner-Weir et al. |
| 6,987,110 B2 | 1/2006 | Zhang et al. |
| 7,005,252 B1 | 2/2006 | Thomson et al. |
| 7,033,831 B2 | 4/2006 | Fisk et al. |
| 7,157,275 B2 | 1/2007 | Guarino et al. |
| 7,297,539 B2 | 11/2007 | Mandalam et al. |
| 7,326,572 B2 | 2/2008 | Fisk et al. |
| 7,371,576 B2 | 5/2008 | Tsang et al. |
| 7,410,798 B2 | 8/2008 | Mandalam et al. |
| 7,413,734 B2 | 8/2008 | Mistry et al. |
| 7,442,548 B2 | 10/2008 | Thomson et al. |
| 7,449,334 B2 | 11/2008 | Thomson et al. |
| 7,510,876 B2 | 3/2009 | D'Amour et al. |
| 7,534,608 B2 | 5/2009 | Martinson et al. |

(Continued)

FOREIGN PATENT DOCUMENTS

| | | |
|---|---|---|
| CN | 1602351 A | 3/2005 |
| EP | 0363125 A2 | 4/1990 |
| EP | 348969 B1 | 5/1993 |
| EP | 0617126 B1 | 9/1994 |
| EP | 0800829 B1 | 10/1997 |
| EP | 92302 B1 | 11/2006 |
| EP | 1873237 A1 | 1/2008 |
| EP | 1391505 B1 | 1/2009 |
| KR | 10-2008-0020098 A | 3/2008 |
| WO | WO9219759 A2 | 2/1992 |

(Continued)

OTHER PUBLICATIONS

Ackermann et al, "Molecular regulation of beta-cell mass" (J of Molecular Endocrinology: 2007, vol. 38, pp. 193-206).*

(Continued)

*Primary Examiner* — Catherine S Hibbert
(74) *Attorney, Agent, or Firm* — Lois A. Gianneschi

(57) ABSTRACT

The present invention provides a method for increasing the expression of MAFA in cells expressing markers characteristic of the pancreatic endocrine lineage comprising the steps of culturing the cells expressing markers characteristic of the pancreatic endocrine lineage in medium comprising a sufficient amount of a cyclin-dependant kinase inhibitor to cause an increase in expression of MAFA.

2 Claims, 15 Drawing Sheets

(56) References Cited

U.S. PATENT DOCUMENTS

| | | |
|---|---|---|
| 7,569,385 B2 | 8/2009 | Haas |
| 7,585,672 B2 | 9/2009 | Odorico et al. |
| 7,704,738 B2 | 4/2010 | D'Amour et al. |
| 7,993,920 B2 | 8/2011 | Martinson et al. |
| 2002/0072117 A1 | 6/2002 | Xu et al. |
| 2003/0082155 A1 | 5/2003 | Habener et al. |
| 2003/0138948 A1 | 7/2003 | Fisk et al. |
| 2003/0180903 A1 | 9/2003 | Bryhan et al. |
| 2004/0015805 A1 | 1/2004 | Kidd et al. |
| 2004/0058412 A1 | 3/2004 | Ho et al. |
| 2004/0062753 A1 | 4/2004 | Rezania |
| 2004/0121461 A1 | 6/2004 | Honmou et al. |
| 2004/0132729 A1 | 7/2004 | Salituro et al. |
| 2004/0161419 A1 | 8/2004 | Strom et al. |
| 2004/0171623 A1 | 9/2004 | Reynolds et al. |
| 2004/0209901 A1 | 10/2004 | Adams et al. |
| 2004/0220393 A1 | 11/2004 | Ward et al. |
| 2004/0241761 A1 | 12/2004 | Sarvetnick et al. |
| 2005/0037488 A1 | 2/2005 | Mitalipova et al. |
| 2005/0037491 A1 | 2/2005 | Mistry et al. |
| 2005/0053588 A1 | 3/2005 | Yin et al. |
| 2005/0054093 A1 | 3/2005 | Haas |
| 2005/0054098 A1 | 3/2005 | Mistry et al. |
| 2005/0054102 A1 | 3/2005 | Wobus et al. |
| 2005/0058631 A1 | 3/2005 | Kihm et al. |
| 2005/0063961 A1 | 3/2005 | Friedlander et al. |
| 2005/0148070 A1 | 7/2005 | Thomson |
| 2005/0158852 A1 | 7/2005 | D'Amour et al. |
| 2005/0187298 A1 | 8/2005 | Vasudevan et al. |
| 2005/0208029 A1 | 9/2005 | Umezawa et al. |
| 2005/0233446 A1 | 10/2005 | Parsons et al. |
| 2005/0244962 A1 | 11/2005 | Thomson |
| 2005/0260749 A1 | 11/2005 | Odorico et al. |
| 2005/0266554 A1 | 12/2005 | D'Amour et al. |
| 2006/0003446 A1 | 1/2006 | Keller et al. |
| 2006/0030042 A1 | 2/2006 | Brivaniou et al. |
| 2006/0040387 A1 | 2/2006 | Fisk et al. |
| 2006/0194315 A1 | 8/2006 | Condie et al. |
| 2006/0194321 A1 | 8/2006 | Colman et al. |
| 2006/0281174 A1 | 12/2006 | Xu et al. |
| 2007/0010011 A1 | 1/2007 | Parsons et al. |
| 2007/0082397 A1 | 4/2007 | Hasson et al. |
| 2007/0154981 A1 | 7/2007 | Hori et al. |
| 2007/0254359 A1 | 11/2007 | Rezania |
| 2007/0259421 A1 | 11/2007 | D'Amour et al. |
| 2007/0259423 A1 | 11/2007 | Odorico et al. |
| 2007/0264713 A1 | 11/2007 | Terstegge et al. |
| 2008/0091234 A1 | 4/2008 | Kladakis et al. |
| 2008/0241107 A1 | 10/2008 | Copland, III et al. |
| 2008/0268533 A1 | 10/2008 | Dalton et al. |
| 2008/0268534 A1 | 10/2008 | Robins et al. |
| 2009/0203141 A1 | 8/2009 | Lin et al. |
| 2009/0298178 A1 | 12/2009 | D'Amour |
| 2010/0003749 A1 | 1/2010 | Uchida et al. |
| 2010/0015711 A1 | 1/2010 | Davis et al. |
| 2010/0028307 A1 | 2/2010 | O'Neil |
| 2010/0093053 A1 | 4/2010 | Oh et al. |
| 2010/0255580 A1 | 10/2010 | Rezania |
| 2011/0014703 A1 | 1/2011 | Xu et al. |
| 2012/0010178 A1* | 1/2012 | Rubin et al. .................. 514/158 |
| 2012/0045830 A1 | 2/2012 | Green et al. |

FOREIGN PATENT DOCUMENTS

| | | | |
|---|---|---|---|
| WO | 9847892 A1 | 10/1998 |
| WO | WO 99/20741 A1 | 4/1999 |
| WO | 0029549 A1 | 5/2000 |
| WO | WO 01/51616 A2 | 7/2001 |
| WO | WO 01/81549 A2 | 11/2001 |
| WO | WO 01/81549 A3 | 11/2001 |
| WO | 0246183 A2 | 6/2002 |
| WO | 0246197 A1 | 6/2002 |
| WO | 02092756 A2 | 11/2002 |
| WO | 03033697 A1 | 4/2003 |
| WO | 03042405 A2 | 5/2003 |
| WO | WO0305049 A1 | 6/2003 |
| WO | 03062405 A2 | 7/2003 |
| WO | 03095452 A1 | 11/2003 |
| WO | WO 03/102134 A2 | 12/2003 |
| WO | 2004016747 A2 | 2/2004 |
| WO | WO 2004/011621 A2 | 2/2004 |
| WO | 2004055155 A2 | 7/2004 |
| WO | 2004073633 A1 | 9/2004 |
| WO | 2004087885 | 10/2004 |
| WO | WO 2004/090110 A2 | 10/2004 |
| WO | WO2005001077 A2 | 1/2005 |
| WO | 2005017117 A2 | 2/2005 |
| WO | WO 2005/014799 A1 | 2/2005 |
| WO | 2005058301 A1 | 6/2005 |
| WO | 2005063971 A1 | 7/2005 |
| WO | WO 2005/065354 A2 | 7/2005 |
| WO | WO 2005/086845 A2 | 9/2005 |
| WO | WO 2005/116073 A2 | 12/2005 |
| WO | WO 2005/116073 A3 | 12/2005 |
| WO | WO2005116073 A3 | 12/2005 |
| WO | 2006020919 A2 | 2/2006 |
| WO | WO 2006/016999 A | 2/2006 |
| WO | 2006026473 A1 | 3/2006 |
| WO | 2006100490 A1 | 9/2006 |
| WO | WO 2006/094286 A2 | 9/2006 |
| WO | 2006114098 A2 | 11/2006 |
| WO | 2006135824 A1 | 12/2006 |
| WO | 2006137787 A1 | 12/2006 |
| WO | WO 2006/138433 A | 12/2006 |
| WO | 2007012144 A1 | 2/2007 |
| WO | 2007016485 A2 | 2/2007 |
| WO | WO 2007/030870 A1 | 3/2007 |
| WO | WO 2007027157 A1 | 3/2007 |
| WO | 2007047509 A1 | 4/2007 |
| WO | 2007051038 A2 | 5/2007 |
| WO | WO 2007/082963 A | 7/2007 |
| WO | WO 2007/103282 A | 9/2007 |
| WO | 2007149182 A2 | 12/2007 |
| WO | WO 2007/139929 A2 | 12/2007 |
| WO | WO 2007/139929 A3 | 12/2007 |
| WO | 2008004990 A2 | 1/2008 |
| WO | 2008013664 A1 | 1/2008 |
| WO | 2008035110 A1 | 3/2008 |
| WO | 2008036447 A2 | 3/2008 |
| WO | 2008048671 A1 | 4/2008 |
| WO | WO2008048647 A1 | 4/2008 |
| WO | 2008094597 | 8/2008 |
| WO | 2008102118 A1 | 8/2008 |
| WO | 2009012428 A1 | 1/2009 |
| WO | 2009018453 A1 | 2/2009 |
| WO | 2009070592 A1 | 6/2009 |
| WO | 2009096902 A1 | 8/2009 |
| WO | 2009101407 A2 | 8/2009 |
| WO | WO2009105570 A2 | 8/2009 |
| WO | 2009131568 A1 | 10/2009 |
| WO | 2010000415 A1 | 1/2010 |

OTHER PUBLICATIONS

Wei et al. (2005, Stem Cells, vol. 23, pp. 166-185).*
Nishimura et al in the post-filing art "Expression of MafA in pancreatic progenitors is detrimental for pancreatic development" (Dev Biol: Sep. 1, 2009, vol. 333, No. 1 pp. 108-120).*
Macfarlane et al in "Glucose Stimulates Translocation of the Homeodomain Transcription Factor PDX1 from the Cytoplasm to the Nucleus in Pancreatic beta-Cells" (JBC, 1999: vol. 274, No. 2, pp. 1011-1016).*
Lee et al (Ann. N.Y. Acad. Sci. 2006: vol. 1070: pp. 393-398).*
Amit et al (Biol. Reprod 68: 2150-2156, 2003).
Ausubel et al.Current Protocols in Molecular Biology, eds. 2001 supplement.
Benvenistry et al. (Benvenistry et al, Stem Cells 2006; 24:1923-1930).
Blyszczuk et al. (PNAS 100:998, 2003).
Cheon et al BioReprod 77 2007.
Ricordi et al Diabetes 37:413-420 (1988).
D'Amour et al, Nature Biotechnology 24, 1392-1401 (2006).

(56) References Cited

OTHER PUBLICATIONS

D'Amour et al, Nature Biotechnology 23, 1534-1541 (2005).
Gordon et al. (PNAS 103: 16806, 2006).
Harlow and Lane, Using Antibodies: A Laboratory Manual, New York: Cold Spring Harbor Laboratory Press (1998).
Hori et al. (PNAS 99: 16105, 2002).
Inzunza et al (Stem Cells 23: 544-549, 2005).
Lee, J.B. et al.: "Establishment and Maintenance of Human Embryonic Stem Cell Lines on Human Feeder Cells Derived from Uterine Endometricum under Serum-Free Condition" Biology of Reproduction, Society for the Study of Reproduction, Campaign, IL, US vol. 72, Jan. 1, 2005 pp. 42-49 XP008083585.
Levenstein et al (Stem Cells 24: 568-574, 2006).
Cheon et al. (BioReprod DOI:10.1095/biolreprod.105.046870, Oct. 19, 2005).
Zhao Li et al.: "The islet beta cell-enriched MafA activator is a key regulator . . . " J. of Biological Chemistry, vol. 280 No. 12 Mar. 25, 2005 pp. 11887-11894 XP002560795.
Zhang et al.: MafA is a key regulator of glucose-stimulated insulin secretion Molecular & Cellular Biology, vol. 25, No. 12, Jun. 2005 pp. 4969-4976 XP002560796.
McLean et al, Stem Cells 25, 29-38 (2007).
Micallef et al. (Diabetes 54:301, 2005).
Miyamoto et al (Stem Cells 22: 433-440, 2004).
Richards et al, (Stem Cells 21: 546-556, 2003).
Reubinoff et al (Nature Biotechnology 18: 399-404 (2000).
Shamblott et al., Proc. Natl. Acad. Sci. USA 95:13726, 1998.
Kubo et al, Development 131, 1651-1662 (2004).
Shiraki et al. Genes Cells. Jun. 2005; 10(6): 503-16.
Skoudy et al. (Biochem. J. 379: 749, 2004).
Stojkovic et al (Stem Cells 2005 23: 306-314, 2005).
Thompson et al (Science Nov. 6, 1998: vol. 282. No. 5391, pp. 1145-1147).
Wang et al (Stem Cells 23: 1221-1227, 2005).
Xu et al (Stem Cells 22: 972-980, 2004).
Gershengorn et al Science 306: 2261-2264, 2004.
Seaberg et al Nature Biotechnology 22: 1115-1124, 2004.
Bonner Wier et al Proc Nat Acad Sci 97: 7999-8004, 2000.
Curr. Top. Dev. Biol. 38:133 ff., 1998.
Thomson et al Proc. Natl. Acad. Sci. U.S.A. 92:7844, 1995.
Lumelsky et al. (Science 292:1389, 2001).
Soria et al. (Diabetes 49:157, 2000).
Miyazaki et al. (Diabetes 53: 1030, 2004).
Kleinman, H.K., et al., Biochemistry 25:312 (1986).
Hadley, M.A., et al., J.Cell.Biol. 101:1511 (1985).
Tulachan et al (Developmental Biology, 305, 2007, pp. 508-521).
Lilja et al J. Biol. Chem., vol. 276, Issue 36, 34199-34205, Sep. 7, 2001.
Marzo et al Diabetalogia, vol. 47, No. 4, 686-694, Apr. 1, 2004.
Ubeda et al J. Biol. Chem., vol. 281,Issue 39, 28858-28864, Sep. 29, 2006.
Wei et al Nature Medicine 11, 1104-1108 (Oct. 1, 2005.
Edlund (Nature Reviews Genetics 3:524-632 (2002).
Vanderford N.L. et al.: "Multiple knases regulate mafA expression in the pancreatic beta cell line MIN6" Archives of Biochemistry & Biophysics, vol. 480, No. 2, Dec. 15, 2008 pp. 138-142 XP002560794.
Abeyta, et al., Jan. 28, 2004, Unique Gene Expression Signatures of Independently-Derived Human Embryonic Stem Cells Lines, Human Molecular Genetics, vol. 13, No. 6, pp. 601-608, Oxford University Press.
Abranches, et al., Apr. 15, 2007, Expansion of Mouse Embryonic Stem Cells on Microcarriers, Biotechnology Bioengineering, vol. 96, No. 6, pp. 1211-1221, Wiley InterScience.
Allegrucci, et al., Aug. 26, 2006, Differences between Human Embryonic Stem Cell Lines, Human Reproduction Update, Advance Access, pp. 1-18.
Amit, et al., 2000, Clonally Derived Human Embryonic Stem Cell Lines Maintain Pluripotency and Proliferative Potential for Prolonged Periods of Culture, Developmental Biology, vol. 227, pp. 271-278.
Amit, et al., 2004, Feeder Layer-and Serum-Free Culture of Human Embryonic Stem Cells, Biology of Reproduction, vol. 70, pp. 837-845.
Arai, et al., 2006, Purification of Recombinant Activin A Using the Second Follistatin Domain of Follistatin-Related Gene (FLRG), Protein Expression & Purification, vol. 49, pp. 78-82.
Armstrong, et al., 2006, The Role of P13K/AKT, MAPK/ERK and NFκβ Signalling in the Maintenance of Human Embryonic Stem Cell Pluripotency and Viability Highlighted by Transcriptional Profiling and Functional Analysis, Human Molecular Genetics, vol. 15, No. 11, pp. 1894-1913.
Author Not Specificed, 2001, A Randomized, Palcebo-Controlled, Clinical Trial of High-Dose Supplementation with Vitamins C and E, Beta Carotene, and Zinc for Age-Related Macular Degeneration and Vision Loss, Arch Ophthalmology, vol. 119, AREDS Report No. 8.
Baetge, 2008, Production of B-Cells from Human Embryonic Stem Cells, Diabetes, Obesity, Metabolism, vol. 10, Supplement 4, pp. 186-194.
Balsam, et al., Apr. 8, 2004, Haematopoeitic Stem Cells Adopt Mature Haeatopoietic Fates in Ischaemic Myocardium, Nature, ?, pp. 668-673, Nature Publishing Group.
Barclay, et al., 1997, The Leucocyte Antigen Facts Book, The Leucocyte Antigen Facts Book, 2[sup]edition, Textbook, Academic Press.
Beltrami, et al., Sep. 19, 2003, Adult Cardiac Stem Cells are Multipotent and Support Myocardial Regeneration, Cell, vol. 114, pp. 763-776, Cell Press.
Bigdeli, et al., 2008, Adaptation of Human Embryonic Stem Cells to Feeder-Free and Matrix-Free Culture Conditions Directly on Plastic Surfaces, Journal of Biotechnology, vol. 133, pp. 146-153.
Blin, et al., Apr. 2010, A Purified Population of Multipotent Cardiovascular Progenitors Derived from Primate Pluripotent Stem Cells Engrafts in Postmyocardial Infarcted Nonhumans Primates, The Journal of Clinical Investigation, vol. 120, No. 4, pp. 1125-1139.
Bocian-Sobkowska, et al., 1999, Polyhormonal Aspect of the Endocrine Cells of the Human Fetal Pancreas, Histochem Cell Biol, vol. 112, Issue 2, pp. 147-153.
Borowiak, et al., 2009, How to Make AB Cells, Current Opinion Cell Biology, vol. 21, Issue 6, pp. 727-732.
Braam, et al., May 2008, Improved Genetic Manipulation of Human Embryonic Stem Cells, Nature Methods, vol. 5, No. 5, pp. 389-392.
Brakenhoff et al., Jan. 7, 1994, Development of a Human Interleukin-6 Receptor Antagonist, Journal of Biological Chemistry, 269-1, 86-93.
Brevig, et al., 2005, The Recognition of Adsorbed and Denatured Proteins of Different Topographies by β2 Integrins and Effects on Leukocyte Adhesion and Activation, Biomaterials, vol. 26, pp. 3039-3053.
Brevini, et al., 2010, No Shortcuts to Pig Embryonic Stem Cells, Theriogenology, vol. 74, pp. 544-550.
Brown, et al., Apr. 14, 2010, Optimal Control of Blood Glucose: The Diabetic Patient or the Machine?, Science Translation Medicine, vol. 2 Issue 27, pp. 1-5.
Burkard et al, Jan. 18, 2007, Conditional Neuronal Nitric Oxide Synthase Overexpression Impairs Myocardial Contractility, Circulation Reseach, vol. 100, pp. e32-e44.
Buzzard et al., Apr. 1, 2004, Karyotype of human ES cells during extended culture, Nature, 22-4, 381-382, Nature Publishing Group.
Cai, et al., Nov. 12, 2009, Generation of Homogeneous PDX1+Pancreatic Progenitors from Human ES Cell-derived Endoderm Cells, Journal of Molecular Cell Biology, vol. 2, pp. 50-60.
Castaing, et al., 2001, Blood Glucose Normalization Upon Transplantation of Human Embryonic Pancreas into Beta-Cell-Deficient SCID Mice, Diabetologica, vol. 44, pp. 2066-2076.
Chambers, et al., May 30, 2003, Functional Expression Cloning of Nanog, a Pluripotency Sustaining Factor in Embryonic Stem Cells, Cell, vol. 113, pp. 643-655.

(56) References Cited

OTHER PUBLICATIONS

Chapple, et al., 2001, Unfolding Retinal Dystrophies: A Role for Molecular Chaperones?, Trends in Molecluar Medicine, vol. 7, No. 9, pp. 414-421.

Chen, et al., Apr. 11, 2009, A Small Molecule that Directs Differentiation of Human ESCs into the Pancreatic Lineage, Nature Chemical Biology, vol. 5, No. 4, pp. 258-265.

Chen, et al., Oct. 15, 2004, Differentiation of Rat Marrow Mesencymal Stem Cells in Pancreatic Islet Beta-Cells, World Journal of Gastroenterology, pp. 3016-3020.

Chen, et al., 2011, Chemically Defined Conditions for Human iPSC Derivation and Culture, Nature Methods, vol. 8, Issue 5, pp. 424-429.

Corbeil, et al., 2001, Rat Prominin, Like its Mouse and Human Orthologues, is a Pentaspan Membrane Glycoprotein, Biochemical and Biophysical Research Communications, vol. 285, No. 4, pp. 939-944.

Crane, et al., 1988, An Embryogenic Model to Explain Cytogenetic Inconsistencies Observed in Chorionic Villus Versus Fetal Tissue, Prenatal Diagnosis, vol. 8, pp. 119-129.

Cure, et al., Mar. 27, 2008, Improved Metabolic Control and Quality of Life in Seven Patients with Type 1 Diabetes Following Islet After Kidney Transplantation, Cell Therapy and Islet Transplantation, vol. 85, No. 6, pp. 801-812.

David M. Chacko, et al., 2000, Survival and Differentiation of Cultured Retinal Progenitors Transplanted in the Subretinal Space of the Rat, Biochemical and Biophysical Research Communications, vol. 268, pp. 842-846, Academic Press.

Denning, et al., 2006, Common Culture Conditions for Maintenance and Cardiomyocyte Differentiation of the Human Embryonic Stem Cell Lines, BG01 and HUES-7, Int. J. Del. Biol., vol. 50, pp. 27-37.

Donovan, et al., Nov. 2001, The End of the Beginning for Pluripotent Stem Cells, Nature, vol. 414, pp. 92-97.

Dorrell, et al., 2008, Editorial, Stem Cell Research, vol. 1, pp. 155-156.

Doyle, et al., 1995, Cell and Tissue Culture: Laboratory Procedures in Biotechnology, Cell and Tiossue Culture: Laboratory Procedures in Biotechnology, Textbook, Textbook, Wiley.

Draper, et al., 2002, Surface Antigens of Human Embryonic Stem Cells: Changes Upon Differentiation in Culture, Journal Anatomy, vol. 200, pp. 249-258, Anatomical Society of Great Britain and Ireland.

Draper, et al., 2004, Recurrent Gain of Chromosomes 17q and 12 in Cultured Human Embryonic Stem Cells, Nature Biotechnology, vol. 22, No. 1, pp. 53-54.

Dupont-Gillain, et al., 2000, Plasma-Oxidized Polystyrene: Wetting Properties and Surface Reconstruction, Langmuir, vol. 16, pp. 8194-8200.

Ellerstrom, et al., 2006, Derivation of a Xeno-Free Human Embryonic Stem Cell Line, Stem Cells, vol. 24, pp. 2170-2176.

Ellerstrom, et al., 2007, Facilitated Expansion of Human Embryonic Stem Cells by Single-Cell Enzymatic Dissociation, Stem Cells, vol. 25, No. 7, pp. 1690-1696.

Ellmers, et al., Jul. 24, 2008, Transforming Growth Factor-B Blockade Down-Regulates the Renin-Angiotensin System and Modifies Cardiac Remodling after Myoardial Infarction, Endocrinology, vol. 149—Issue 11, pp. 5828-5834, The Endocrine Society.

Enzmann, et al., Dec. 2003, Enhanced Induction of RPE Lineage Markers in Pluripootent Neural Stem Cells Engrafted into the Adult Rat Subretinal Space, Opthamology & Visual Science, vol. 44, No. 12, pp. 5417-5422, Association for Research in Vision and Ophthamology.

Eventov-Friedman, et al., Jul. 2006, Embryonic Pig Pancreatic Tissue Transplantation for the Treatment of Diabetes, PLoS Medicine, vol. 3, Issue 7, e215, pp. 1165-1177.

Ezashi, et al., Mar. 29, 2005, Low 02 Tensions and the Prevention of Differentiation of hES Cells, Proceedings of the National Academy of Sciences of USA, vol. 102, No. 13, pp. 4783-4788.

Fauza, 2004, Amniotic Fluid and Placental Stem Cells, Ballieres Best Practice and Research Clinical Obsterics and Gynaecology, vol. 18, No. 6, pp. 877-891.

Fidler et al., Jul. 15, 1986, Selective Immunomodulation by the Antineoplastic Agent Mitoxantrone, Journal of Immunology, 137-2, 727-732, American Society of Immunologists.

Fischer, et al., 2003, Residues in the C-Terminal Region of Activin A Determine Specificity for Follistatin and Type II Receptor Binding, Journal of Endocrinology, vol. 176, pp. 61-68, Society for Endocrinology.

Fok, et al., 2005, Shear-Controlled Single-Step Mouse Embryonic Stem Cell Expansion and Embryoid Body-Based Differentiation, Stem Cells, vol. 23, pp. 1333-1342.

Frandsen et al., Aug. 15, 2007, Activin B mediated induction of Pdx1 in human embryonic stemcell derived embryoid bodies, Biochemical and Biophysical Research Communications, 362, 568-574, Elsevier Inc.

Fung, et al., Jul. 15, 2007, The Effect of Medical Therapy and Islet Cell Transplantation on Diabetic Nephropathy: An Interim Report, Transplantation, vol. 84, No. 1, pp. 17-22.

Gaspar, et al., 2007, Inhibition of Transforming Growth Factor Signaling Reduces Pancreatic Adenocarcinoma Growth and Invasiveness, Molecular Pharmacology, vol. 72, Issue 1, pp. 152-161.

Giltaire, et al., 2009, The CYP26 Inhibitor R115866 Potentiates the Effects of All-Trans Retinoic Acid on Cultured Human Epidermal Keratinocytes, British Journal of Dermatology, vol. 160, pp. 505-513.

Ginis, et al., 2004, Differences Between Human and Mouse Embryonic Stem Cells, Developmental Biology, vol. 269, pp. 360-380.

Gosden, et al., 1983, Amniotic Fluid Cell Types and Culture, British Medical Bulletin, vol. 39, No. 4, pp. 348-354.

Graham, et al., 1977, Characteristics of a Human Cell Line Transformed by DNA from Human Adenovirus Type 5, Journal General Virology, vol. 36, pp. 59-72.

Guo, et al., May 2009, Stem Cells to Pancreatic B-Cells: New Sources for Diabetes Cell Therapy, Endocrine Reviews, vol. 30, No. 3, pp. 214-227, The Endocrine Society.

Hamann, et al., Mar. 11, 1997, Phenotypic and Functional Separation of Memory and and Effector Human CD8+T Cells, Journal of Experimental Medicine, 186-9, 1407-1418, Rockefeller University Press.

Harb, et al., 2008, The Rho-Rock-Myosin Signaling Axis Determines Cell-Cell Integrity of Self-Renewing Pluripotent Stem Cells, Plos One, vol. 3, Issue 8, Article e3001, XP002530386.

Haruta, et al., Mar. 2004, In Vitro and In Vivo Characterization of Pigment Epithelieal Cells Differentiated from Primate Embryonic Stem Cells, Investigative Ophthalmology & Visual Science, vol. 45, No. 3, pp. 1020-1025, Association for Research in Vision and Ophthalmology.

Hasegawa, et al., 2006, A Method for the Selection of Human Embryonic Stem Cell Sublines with High Replating Efficiency After Single-Cell Dissociation, Stem Cells, vol. 24, pp. 2649-2660.

Hashemi, et al., Dec. 11, 2007, A Placebo Controlled, Dose-Ranging, Safety Study of Allogenic Mesenchymal Stem Cells Injected by Endomyocardial Delivery after an Acute Myocardial Infarction, European Heart Journal, vol. 29, pp. 251-259.

Held, et al., 1984, The Effect of Oxygen Tension on Colony Formation and Cell Proliferation of Amniotic Fluid Cells In-Vitro, Prenatal Diagnosis, vol. 4, No. 3, pp. 171-180.

Henderson, et al., 2002, Preimplantation Human Embryos and Embryonic Stem Cells Show Comparable Expression of Stage-Specific Embryonic Antigens, Stem Cells, vol. 20, pp. 329-337.

Heng, et al., 2007, Mechanical dissociation of human embryonic stem cell colonies by manual scraping after collagenase treatment is much more detrimental to cellular viability than is trypsinization with gentle pipetting, Biotechnol. Appl. Biochem., 47, 33-37, Portland Press Ltd.

Herzenberg, et al., 1976, Fluorescence-activated Cell Sorting, Scientific American, 234, 108-117, Scientific American.

Hess, et al., Jul. 2003, Bone Marrow-Derived Stem Cells Initiate Pancreatic Regeneration, Nature Biotechnology, vol. 21, No. 7, pp. 763-770.

Hichem Frigui, et al., May 1, 1999, A Robust Competitive Clustering Algorithm With Applications in Computer Vision, IEEE, 21-5, 450-465, IEEE.

Ho, et al., 1991, Animal Cell Bioreactors, Animal Cell Bioreactors, Hardcover, 1-512, Butterworth-Heinemann.

(56) References Cited

OTHER PUBLICATIONS

Hoehn, et al., 1982, Morphological and Biochemical Heterogeneity of Amniotic Fluid Cells in Culture, Methods in Cell Biology, vol. 26, pp. 11-34, Academic Press, Inc.

Hussain, et al., 2004, Stem-Cell Therapy for Diabetes Mellitus, Lancet, vol. 364, pp. 203-205.

Ianus, et al., Mar. 2003, In Vivo Derivation of Glucose-Competent Pancreatic Endocrine Cells from Bone Marrow Without Evidence of Cell Fusion, The Journal of Clinical Investigation, vol. 111, No. 6, pp. 843-850.

Inami, et al., Jun. 24, 2010, Differentiation of Induced Pluripotent Stem Cells to Thymic Epithelial Cells by Phenotype, Immunology and Cell Biology, doi:10.1038/icb.2010.96, pp. 1-8.

Int' Anker, et al., Aug. 15, 2003, Amniotic Fluid as a Novel Source of Mesenchymal Stem Cells for Therapeutic Transplantation, Blood, vol. 102, No. 4, pp. 1548-1549.

Jafary, et al., 2008, Differential effect of activin on mouse embryonic stem cell differentiation in insulin-secreting cells under nestin-positive selection and spontaneous differentiation protocols, Cell Biology International, 32, 278-286, Elsevier.

Jeon, et al., 2009, Endocrine Cell Clustering During Human Pancreas Development, J Histochem Cytochem, vol. 57, Issue 9, pp. 811-824.

Jiang, et al., 2007, Generation of Insulin-Producing Islet-Like Clusters from Human Embryonic Stem Cells, Stem Cells, vol. 25, Issue 8, pp. 1940-1953.

Johansson, et al., Mar. 2007, Temporal Control of Neurogenin3 Activity in Pancreas Progenitors Reveals Competence Windows for the Generation of Different Endocrine Cell Types, Developmental Cell, vol. 12, pp. 457-465.

Kahan, Aug. 2003, Pancreatic Precursors and Differentiated Islet Cell Types from Murine Embryonic Stem Cells, Diabetes, vol. 52, pp. 2016-2042.

Kelly, et al., 2011, Cell-Surface Markers for the Isolation of Pancreatic Cell Types Derived from Human Embryonic Stem Cells, Nature Biotechnology, vol. 29, Issue 8, pp. 750-756.

Kicic, et al., Aug. 27, 2003, Differentiation of Marrow Stromal Cells into Photoreceptors in the Rat Eye, The Journal of Neuroscience, vol. 23, Issue 21, pp. 7742-7749.

Kingsley, 1994, The TGF-B Superfamily: New Members, New Receptors, and New Genetic Tests of Function in Different Organisms, Genes & Development, vol. 8, pp. 133-146, XP009011502, Cold Spring Harbor Laboratory Press.

Kinkel, et al., May 12, 2009, Cyp26 Enzymes Function in Endoderm to Regulate Pancreatic Field Size, PNAS, vol. 106, No. 19, pp. 7864-7869.

Klimanskaya, et al., May 2005, Human Embryonic Stem Cells Derived without Feeder Cells, Lancet, vol. 365, No. 9471, pp. 1636-1641.

Koblas, et al., 2008, Differentiation of CD133-Positive Pancreatic Cells Into Insulin-Producing Islet-Like Cell Clusters, Transplantation Proceedings, vol. 40, pp. 415-418.

Kohen, et al., Dec. 2009, Characterization of Matrigel Interfaces During Defined Human Embryonic Stem Cell Culture, Biointerphases, pp. 6979.

Koller, et al., Jul. 15, 1992, Effects of Synergistic Cytokine Combinations, Low Oxygen, and Irradiated Stroma on the Expansion of Human Cord Blood Progenitors, Blood, vol. 80, No. 2, pp. 403-411.

Koyangi et al., Sep. 7, 2007, Inhibitio nof the Rho/ROCK Pathway Reduces Apoptosis During Transplantatation of Embryonic Stem Cell-Derived Neural Precursors, Journal of Neuroscience Research, 86, 270-280, Wiley-Liss, Inc.

Krapcho et al., 1985, Synthesis and Antineoplastic Evaluations of 5,8-Bis[(aminoalkyl)amino]-1-azaanthracene-9,10-diones, Journal of Medical Chemistry, 28, 1124-1126, American Chemical Society.

Krawetz, et al., 2009, Human Embryonic Stem Cells: Caught Between a ROCK Inhibitor and a Hard Place, BioEssays: News and Reviews in Molecular Cellular and Developmental Biology, vol. 31, pp. 336-343.

Kron, et al., 1998, Expression of Human Activin C Protein in Insect Larvae Infected with a Recombinant Baculovirus, Journal of Virological Methods, vol. 72, pp. 9-14.

Kroon, et al., Apr. 2008, Pancreatic Endoderm Derived from Human Embryonic Stem Cells Generates Glucose-Responsive Insulin-Secreting Cells in vivo, Nature Biotechnology, vol. 26, No. 4, pp. 443452.

Ku et al., 2004, Committing Embryonic Stem Cells to Early Endocrine Pancreas In Vitro, Stem Cells, 22, 1205-1217, AlphaMed Press.

Lanza, et al., 2010, Characteristics and Characterization of Human Pluripotent Stem Cells, Stem Cell Anthology, 1st Edition, pp. 141, 142, 144 and 146.

Laplante, et al., 2004, RhoA/ROCK and Cdc42 Regulate Cell-Cell Contact and N-Cadherin Protein Level During Neurodetermination of P19 Embryonal Stem Cells, Journal of Neurobiology, vol. 60, No. 3, pp. 289-307.

Larsen, et al., 2007, Evaluation of B-Cell Mass and Function in the Gottingen Minipig, Diabetes, Obesity and Metabolism, vol. 9, Supplement 2, pp. 170-179, Blackwell Publishing Ltd.

Le Blanc, et al., 2003, Mesenchymal Stem Cells Inhibit and Stimulate Mixed Lymphocyte Cultures and Mitogenic Responses Independently of the Major Histocompatibility Complex, Scandinavian Journal of Immunology, vol. 57, pp. 11-20, Blackwell Publishing Ltd.

Lee, et al., Apr. 15, 2009, Human B-cell Precursors Mature into Functional Insulin-Producing Cells in an Immunoisolation Device: Implications for Diabetes Cell Thereapies, Transplantation, vol. 87, No. 7, pp. 983-991.

Li, et al., Jan. 9, 2009, Generation of Rat and Human Induced Pluripotent Stem Cells by Combining Genetic Reprogramming and Chemical Inhibitors, Cell Stem Cell, vol. 4, pp. 16-19.

Lim, et al., 2002, Proteome Analysis of Conditioned Medium from Mouse Embryonic Fibroblast Feeder Layers which Support the Growth of Human Embryonic Stem Cells, Proteomics, vol. 2, pp. 1187-1203.

Liu, et al., 2006, A Novel Chemical-Defined Medium with bFGF and N2B27 Supplements Supports Undifferentiated Growth in Human Embryonic Stem Cells, Biochemical and Biophysical Research Communications, vol. 346, pp. 131-139.

Loh, et al., 2011, Genomic Approaches to Deconstruct Puripotency, Annu Rev Genomics Hum Genet, vol. 12, pp. 165-185.

Ludwig, et al., Feb. 2006, Derivation of Human Embryonic Stem Cells in Defined Conditions, Nature Biotechnology, vol. 24 No. 2, pp. 185-187.

Lund, et al., 2001, Cell Transplantation as a Treatment for Retinal Disease, Progress in Retinal and Eye Research, vol. 20, No. 4, pp. 415-449, Elsevier Science Ltd.

Lund, et al., Aug. 2003, Retinal Transplantation: Progress and Problems in Clinical Application, Journal of Leukocyte Biology, vol. 74, pp. 151-160.

Lyttle, et al., 2008, Transcription Factor Expression in the Developing Human Fetal Endocrine Pancreas, Diabetologica, vol. 51, pp. 1169-1180, Spring-Verlag.

Maherali, et al., Jul. 2007, Directly Reprogrammed Fibroblasts Show Global Epigenetic Remodeling and Widespread Tissue Contribution, Cell Stem Cell, vol. 1, pp. 55-70, Elsevier, Inc.

Marshall, et al., 1980, Early Micro-and Macro-Angiopathy in the Streptozotocin, Research in Experimental Medicine, vol. 177, pp. 145-158, Springer-Verlag.

Marshall, et al., 2001, Isolation and Maintenance of Primate Embryonic Stem Cells, Methods in Molecular Biology, vol. 158, pp. 11-18.

Martin, et al., Jul. 14, 2005, Bioreactors for Tissue Mass Culture: Design, Characterization, and Recent Advances, Biomaterials, vol. 26, pp. 7481-7503.

McKiernan, et al., 2007, Directed Differentiation of Mouse Embryonic Stem Cells into Pancreatic-Like or Neuronal- and Glial-Like Phenotypes, Tissue Engineering, vol. 13, No. 10, pp. 2419-2430.

McLin, et al., 2007, Repression of WNT/(szligbeta)-6atenin Signaling in the Anterior Endoderm is Essential for Liver and Pancreas Development, Development, vol. 134, Issue 12, pp. 2207-2217.

Meijer, et al., Sep. 2004, Pharmacological Inhibitors of Glycogen Synthase Kinase 3, Trends in Pharmacological Sciences, vol. 25, No. 9, pp. 471-480.

(56) References Cited

OTHER PUBLICATIONS

Michael J. Borowitz, et al., Jun. 1, 1997, Prognostic Significance of Fluorescence Intensity of Surface Marker . . . , Blood, 89-11, 3960-3966, American Society of Hematology, Washington, D.C.

Miller, et al., 1987, The Pig as a Model for Human Nutrition, Annual Review of Nutrition, vol. 7, pp. 361-382, Annual Reviews Inc.

Milunsky, et al., 2011, Genetic Disorders and the Fetus: Diagnosis Prevention and Treatment, Pediatric and Developmental Pathology, vol. 14, pp. 84, Society for Pediatric Pathology.

Mitalipova, et al., 2005, Preserving the Genetic Integrity of Human Embyonic Stem Cells, Nature Biotechnology, vol. 23, No. 1, pp. 19-20.

Mitsui, et al., May 30, 2003, The Homeoprotein Nanog is Required for Maintenance of Pluripotency in Mouse Epiblast and ES Cells, Cell, vol. 113, pp. 631-642, Cell Press.

Moore, et al., 2002, The Corneal Epithelial Stem Cell, DNA and Cell Biology, vol. 21, No. 5/6, pp. 443-451.

Morrison, et al., Oct. 1, 2000, Culture in Reduced Levels of Oxygen Promotes Clonogenic Sympathoadrenal Differentiation by Isolated Neural Crest Stem Cells, Journal of Neuroscience, vol. 20, No. 19, pp. 7370-7376.

Movassat, et al., 2003, Keratinocyte Growth Factor and Beta-Cell Differentiation in Human Fetal Pancreatic Endocrine Precursor Cells, Diabetologia, vol. 46, pp. 822-829.

Munoz, et al., 2008, Conventional Pluripotency Markers are Unspecific for Bovine Embryonic-Derived Cell-Lines, Theriogenology, vol. 69, pp. 1159-1164.

Nakagawa, et al., Jan. 2008, Generation of Induced Pluripotent Stem Cells without Myc from Mouse and Human Fibroblasts, vol. 26, No. 1, pp. 101-106.

Nakamura, et al., Oct. 2003, Ocular Surface Reconstruction Using Cultivated Mucosal Epithelial Stem Cells, Cornea, vol. 22, Supplement 1, S75-S80.

Nicholas et al., 2007, A Method for Single-Cell Sorting and Expansion of Genetically modified Human Embryonic Stem Cells, Stem Cells and Development, 16, 109-117, Mary Ann Liebert, Inc.

Nostro, et al., 2011, Stage-Specific Signaling Through TGF Family Members and WNT Regulates Patterning and Pancreatic Specification of Human Pluripotent Stem Cells, Development, vol. 138, Issue 5, pp. 861-871.

Not Specified, Jul. 1, 1989, RecName: Full=Inhibin beta B Chain; AltName: Full=Activin beta-B chain; Flags; Precurso, Database UniProt [Online], EBI Accession No. Uniprot: P09529, Database Accession No. P09529.

Oh, et al., 2006, Human Embryonic Stem Cells: Technological Challenges Towards Therapy, Clinical and Experimental Pharmacology and Physiology, vol. 33, pp. 489-495.

Okita, et al., Jul. 19, 2007, Generation of Germline-Competent Induced Pluripotent Stem Cells, Nature, vol. 448, pp. 313-317.

Osborne, et al., 2003, Some Current Ideas on the Pathogenesis and the Role of Neuroprotection in Glaucomatous Optic Neuropathy, European Journal of Ophthalmology, vol. 13, Supplement 3, S19-S26, Wichtig Editore.

Ostrom, et al., Jul. 30, 2008, Retinoic Acid Promotes the Generation of Pancreatic Endocrine Progenitor Cells and Their Further Differentiation into B-Cells, PLOS One, vol. 3, No. 7, e2841, pp. 1-7.

Paling, et al., 2004, Regulation of Embryonic Stem Cell, Self-Renewal by Phosphoinositide 3-kinase-dependent Signaling, Journal of Biological Chemistry, vol. 279, No. 46, pp. 48063-48070.

Panchision, et al., 2007, Optimized Flow Cytometric Analysis of Central Nervous System Tissue Reveals Novel Functional Relationships Among Cells Expressing CD133, CD15, and CD24, Stem Cells, vol. 25, pp. 1560-1570.

Panepinto, et al., Aug. 1986, The Yucatan Miniature Pig: Characterization and Utilization in Biomedical Research, Laboratory Animal Science, vol. 36, No. 4, pp. 344-347, American Association for Laboratory Animal Science.

Pangas, et al., 2002, Production and Purification of Recombinant Human Inhibin and Activin, Journal of Endocrinology, vol. 172, pp. 199-210.

Pardo, et al., 2005, Corning CellBIND Surface: An Improved Surface for Enhanced Cell Attachment, Corning Technical Report, XP002530385, 8 page report.

Paris, et al., 2010, Equine Embryos and Embryonic Stem Cells: Defining Reliable Markers of Pluripotency, Theriogeneology, vol. 74, pp. 516-524.

Peerani, et al., 2007, Niche-Mediated Control of Human Embryonic Stem Cell Self-Renewal and Differentiation, The EMBO Journal, vol. 26, pp. 4744-4755.

Peter O. Krutzik, et al., May 30, 2005, Coordinate Analysis of Murine Immune Cell Surface Markers and Intracellular Phosphoproteins by Flow Cytometry, Journal of Immunology, 175, 2357-2365, American Association of Immunologists, Inc.

Phillips, et al., 2008, Attachment and Growth of Human Embryonic Stem Cells on Microcarriers, Journal of Biotechnology, vol. 138, pp. 24-32.

Pouton, et al., Aug. 2007, Embryonic Stem Cells as a Source of Models for Drug Discovery, Nature Reviews Drug Discovery, vol. 6, No. 8, pp. 1474-1776.

Prichard, et al., 2006, Adult Adipose Derived Stem Cell Attachment to Biomaterials, Biomaterials, vol. 28, No. 6, pp. 936-946.

Prowse, et al., 2005, A Proteome Analysis of Conditioned Media from Human Neonatal Fibroblasts Used in the Maintenance of Human Embryonic Stem Cells, Proteomics, vol. 5, pp. 978-989.

Prusa, et al., Oct. 4, 2003 —Expressing Cells in Human Amniotic Fluid: a New Source for Stem Cell Research?, Human Reproduction, vol. 18, No. 7, pp. 1489-1493.

Rajagopal, et al., Jan. 17, 2003, Insulin Staining of ES Cell Progeny from Insulin Uptake, Science, vol. 299, pp. 363.

Rao, Aug. 10, 2004, Conserved and Divergent Paths that Regulate Self-Renewal in Mouse and Human Embryonic Stem Cells, Developmental Biology, vol. 275, pp. 269-286, Elsevier, Inc.

Rebollar, et al., 2008, Proliferation of Aligned Mammalian Cells on Laser-Nanostructured Polystyrene, Biomaterials, vol. 29, pp. 1796-1806.

Reisner, 2007, Growing Organs for Transplantation form Embryonic Precursor Tissues, Immunol. Res., vol. 38, pp. 261-273.

Rezania, 2011, Production of Functional Glucagon-Secreting-Cells from Human Embryonic Stem Cells, Diabetes, vol. 60, Issue 1, pp. 239-247.

Ryan, et al., Apr. 2001, Clinical Outcomes and Insulin Secretion After Islet Transplantation with the Edmonton Protocol, Diabetes, vol. 50, pp. 710-719.

Sakaguchi, et al., 2002, Integration of Adultmesenchymal Stem Cells in the CNS, Society for Neuroscience Abstract Viewer and Itineray Planner, Program 237.18, XP002519394.

Sato, et al., 2006, Manipulation of Self-Renewal in Human Embryonic Stem Cells Through a Novel Pharmacological GSK-3 Inhibitor, Methods in Molecular Biology, vol. 331, pp. 115-128.

Sato, et al., Apr. 23, 2003, Molecular Signature of Human Embryonic Stem Cells and its Comparison with the Mouse, Developmental Biology, vol. 260, pp. 404-413.

Sato, et al., Jan. 2004, Maintenance of Pluripotency in Human and Mouse Embryonic Stem Cells Through Activation of Wnt Signaling by a Pharmacological GSK-3-specific Inhibitor, Nature Medicine, vol. 10, No. 1, pp. 55-63.

Savino et al., 1994, Generation of Interleukin-6 Receptor Antagonists by Molecular-Modeling Guided Mutagenesis of Residues Important for gp130 Activation, EMBO Journal, 13-6, 1357-1367.

Schraermeyer, et al., 2001, Subretinally Transplanted Embryonic Stem Cells Rescue Photoreceptor Cells From Degeneration in the RCS Rats, Cell Transplantation, vol. 10, pp. 673-680.

Schroeder, et al., 2005, Differentiation of Mouse Embryonic Stem Cells to Insulin-Producing Cells, Nature Protocols, vol. 1, No. 2, pp. 495-507.

Scullica, et al., 2001, Diagnosis and Classification of Macular Degenerations: an Approach Based on Retinal Function Testing, Documenta Ophthalmologica, vol. 102, pp. 237-250.

Segev, et al., Jan. 1, 2004, Differentiation of Human Embryonic Stem Cells into Insulin-Producing Clusters, Stem Cells, pp. 265-274.

(56) References Cited

OTHER PUBLICATIONS

Shapiro, et al., Jul. 27, 2000, Islet Transplantation in Seven Patients with Type 1 Diabetes Mellitus Using a Glucocorticoid-Free Immunosuppressive Regimen, The New England Journal of Medicine, vol. 343, No. 4, pp. 230-238, The Massachusetts Medical Society.
Shen, et al., 2001, The Effects of Surface Chemistry and Adsorbed Proteins on Monocyte/Macrophage Adhesion to Chemically Modified Polystyrene Surfaces, Journal of Biomedical Matter Research, vol. 57, pp. 336-345.
Sherwood, et al., 2009, Transcriptional Dynamics of Endodermal Organ Formation, Developmental Dynamics, vol. 238, Issue 1, pp. 29-42.
Shi et al., 2005, Inducing Embryonic Stem Cells to Differentiate into Pancreatic β Cells by a Novel Three-Step Approach with Activin A and All-Trans Retinoic Acid, Stem Cells, 23, 656-662, AlphaMed Press.
Shindler et al., Apr. 18, 2005, A synthetic nanofibrillar matrix promotes in vivo-like organization and morphogenesis for cells in culture, Biomaterials, 26, 5624-5631, Elsevier.
Shiraki, et al., 2008, Guided Differentiation of Embryonic Stem Cells into Pdx1-Expressing Regional-Specific Definitive Endoderm, Stem Cells, vol. 26, pp. 874-885.
Sidhu et al., 2006, Derivation of Three Clones from Human Embryonic Stem Cell Lines by FACS Sorting and Their Characterization, Stem Cells and Development, 15, 61-69, Mary Ann Liebert, Inc.
Simons, et al., 1997, Assembly of Protein Tertiary Structures from Fragments with Similar Local Sequences Using Simulated Annealing and Bayesian Scoring Functions, Journal of Molecular Biology, vol. 268, pp. 209-225.
Simons, et al., 1999, Improved Recognition of Native-Like Protein Structures Using a Combination of Sequence-Dependent and Sequence-Independent Features of Proteins, Proteins: Structure, Function, and Genetics, vol. 34, pp. 82-95, Wiley-Liss, Inc.
Smith et al., Mar. 2, 2001, Anti-Interleukin-6 Monocolnal Antibody Induces Regression of Human Prostate Cancer Xenografts in Nude Mice, The Prostate, 48, 47-53, Wiley-Liss, Inc.
Stadtfeld, et al., Mar. 2008, Defining Molecular Cornerstones During Fibroblast to iPS Cell Reprogramming in Mouse, Cell Stem Cell, vol. 2, pp. 230-240.
Stafford, et al., 2002, Retinoic Acid Signaling is Required for a Critical Early Step in Zebrafish Pancreatic Development, Current Biology, vol. 12, Issue 14, pp. 1215-1220.
Stephen D. De Rosa, Feb. 1, 2001, 11-color, 13-parameter flow cytometry: Identification of . . . , Nature, 7-2, 245-248, Nature Publishing Group.
Sugiyama, et al., Jan. 2, 2007, Conserved Markers of Fetal Pancreatic Epithelium Permit Prospective Isolation of Islet Progenitor Cells by FACS, PNAS, vol. 104, No. 1, pp. 175-180.
Sugiyama, et al., 2008, Fluorescence-Activated Cell Sorting Purification of Pancreatic Progenitor Cells, Diabetes, Obesity and Metabolism, vol. 10, Supplement 4, pp. 179-185.
Suh, et al., 1991, Characterization of His-X3-His Sites in a-Helices of Synthetic Metal-Binding Bovine Somatotropin, Protein Engineering, vol. 4, No. 3, pp. 301-305.
Takahashi, et al., 2003, Homogenous Seeding of Mesenchymal Stem Cells into Nonwoven Fabric for Tissue Engineering, Tissue Engineering, vol. 9, No. 5, pp. 931-938.
Takahashi, et al., 2007, Induction of Pluripotent Stem Cells from Adult Human Fibroblasts by Defined Factors, Cell, vol. 131, pp. 861-872.
Takehara, et al., 2008, Rho-Associate Kinase Inhibitor Y-27632 Promotes Survival of Cynomolgus Monkey Embryonic Stem Cells, Molecular Human Reproduction, vol. 14, No. 11, pp. 627-634.
Tang, et al., 2006, Reprogramming Liver-Stem WB Cells into Functional Insulin-Producing Cells by Persistent Expression of Pdx1-and Pdx1-VP16 Mediated by Lentiviral Vectors, Laboratory Investigation, vol. 86, pp. 83-93.
Tannock, et al., 1996, Chemotherapy with Mitoxantrone Plus Prednisone or Prednisone Alone for Symptomatic Hormone-Resistant Prostate Cancer: A Canadian Randomized Trial With Palliative End Points, Journal of Clinical Oncology, 14-6, 1756-1764, American Society of Clinical Oncology.
Teare, et al., 2000, Cellular Attachment to Ultraviolet Ozone Modified Polystyrene Surfaces, Langmuir, vol. 16, pp. 2818-2824.
Tomita, et al., 2002, Bone Marrow-Derived Stem Cells Can Differentiate into Retinal Cells in Injured Rat Retina, Stem Cells, vol. 20, pp. 279-283.
Tsai, et al., Apr. 22, 2004, Isolation of Human Multipotent Mesenchymal Stem Cells from Second-Trimester Amniotic Fluid Using a Novel Two-Stage Culture Protocol, Human Reproduction, vol. 19, No. 6, pp. 1450-1456.
Uludag, et al., 2000, Technology of Mammalian Cell Encapsulation, Advanced Drug Delivery Reviews, vol. 42, pp. 29-64.
Ungrin, et al., 2008, Reproducible, Ultra High-Throughput Formation of Multicellular Organization from Single Cell Suspension-Derived Human Embryonic Stem Cell Aggregates, Plos ONE, vol. 3, Issue 2, e1565, pp. 1-12.
Unknown, 2006, Preserve the Stability of Your Stem Cells, Stem Cells, XP002496166, Internet Citation.
Unknown, Feb. 26, 1992, MeSH Descriptor Data, National Library of Medicine—Medical Subject Headings, XP002553615.
Vacanti, et al., Jan. 1988, Selective Cell Transplantation Using Bioabsorbable Artificial Polymers as Matrices, Journal of Pediactric Surgery, 23-1, 3-9.
Valet, et al., Feb. 17, 2003, Pretherapeutic Identification of High-Risk Acute Myeloid Leukemia (AML) Patients from . . . , Clinical Cytometry, 53B, 4-10, Wiley-Liss, Inc.
Vallier, et al., 2005, Activin/Nodal and FGF Pathways Cooperate to Maintain Pluripotency of Human Embryonic Stem Cells, Journal of Cell Sciences, vol. 118, pp. 4495-4509.
Van Der Greef et al., Dec. 1, 2005, Rescuing drug discovery: in vivo systems pathology and systems pharmacology, Nature, 4-1, 961-967, Nature Reviews.
Van Der Windt, et al., 2008, The Chioce of Anatomical Site for Islet Transplantation, Cell Transplantation, vol. 17, pp. 1005-1014.
Van Kooten, et al., 2004, Plasma-Treated Polystyrene Surfaces: Model Surfaces for Studying Cell-Biomaterial Interactions, Biomaterials, vol. 25, pp. 1735-1747.
Van Wachem, et al., 1990, Method for the Fast Application of an Evenly Distributed Cell Layer on Porous Vascular Grafts, Biomaterials, vol. 11, pp. 602-606.
Vodicka, et al., 2005, The Miniature Pig as an Animal Model in Biomedical Research, Annals New York Academy of Sciences, vol. 1049, pp. 161-171.
Vunjak-Novakovic, et al., 1998, Dynamic Cell Seeding of Polymer Scaffolds for Cartilage Tissue Engineering, Biotechnology Program, vol. 14, Issue 2, pp. 193-202.
Wang et al., 1987, Relationship of Chemical Structurs of Anthraquinones with their Effects onthe Suppression of Immune Responses, International Journal of Immunopharmacology, 9-6, 733-739, International Society for Immunopharmacology.
Wang, et al., 2005, Noggin and bFGF Cooperate to Maintain the Pluripotency of Human Embryonic Stem Cells in the Absence of Feeder Layers, Biochemical and Biophysical Research Communications, vol. 33, No. 3, pp. 934-942.
Watanabe, et al., 2007, A Rock Inhibitor Permits Survival of Dissociated Human Embryonic Stem Cells, Nature Biotechnology, vol. 25, No. 6, pp. 681-686.
Wei, et al., 2003, Human Amnion-Isolated Cells Normalize Blood Glucose in Strepozotocin Induced Diabetic Mice, Cell Transplantation, vol. 12, No. 5, pp. 545-552.
Wells, et al., 2000, Early Mouse Endoderm is Patterned by Soluble Factors from Adjacent Germ Layers, Development, vol. 127, Issue 8, pp. 1563-1572.
Wernig, et al., Jan. 2008, c-Myc is Dispensable for Direct Reprogramming of Mouse Fibroblasts, Cell Stem Cell, vol. 2, pp. 10-12.
Wiles et al., 1999, Embryonic Stem Cell Development in a Chemically Defined Medium, Experimental Cell Research, 247, 241-248, Academic Press.

(56) References Cited

OTHER PUBLICATIONS

Wilson, et al., 2005, The HMG Box Transcription Factor Sox4 Contributes to the Development of the Endcrine Pancreas, Diabetes, vol. 54, Issue 12, pp. 3402-4309.
Xu, et al., 2001, Feeder-free Growth of Undifferentiated Human Embryonic Stem Cells, Nature Biotechnology, vol. 19, pp. 971-974.
Xu, et al., 2005, Basic FGF and Suppression of BMP Signalling Sustain Undifferentiated Proliferation of Human ES Cells, Nature Methods, vol. 2, Issue 3, pp. 185-189.
Yang et al., Feb. 27, 2001, Novel cell immobilization method utilizing centrifugal force to achieve high-density hepatocyte culture in porous scaffold, Journal of Biomed Materials Research, 55, 379-386, John Wiley & Sons, Inc.
Yang, et al., 2002, Survival of Pancreatic Islet Xenografts in NOD Mice with the Theracyte Device, Transplantation Proceedings, vol. 34, pp. 3349-3350.
Yasuda, et al., Apr. 4, 2009, Development of Cystic Embryoid Bodies with Visceral Yolk-Sac-Like Structures from Mouse Embryonic Stem Cells Using Low-Adherence 96-Well Plate, Journal of Bioscience and Bioengineering, vol. 107, No. 4, pp. 442-446.
Yoneda, et al., 2005, The Rho Kinases I and II Regulate Different Aspects of Myosin II Acitivity, The Journal of Cell Biology, vol. 170, No. 3, pp. 443-445.
Young, et al., 2003, Three-Dimensional Culture of Human Uterine Smooth Muscle Nyocytes on a Resorbably Scaffolding, Tissue Engineering, vol. 9, No. 3, pp. 451-459.
Yu, et al., Dec. 21, 2007, Induced Pluripotent Stem Cell Lines Derived from Human Somatic Cells, Science, vol. 318, pp. 1917-1920.
Yu, et al., Jun. 6, 2006, Isolation of a Novel Population of Multipotent Adult Stem Cells from Human Hair Follicles, American Journal of Pathology, vol. 168, No. 6, pp. 1879-1888.
Zhang, et al., 2004, Differentiation Potential of Bone Marrow Mesenchymal Stem Cells into Retina in Normal and Laser-Injured Rat Eye, Science in China Series, vol. 47, No. 3, pp. 241-250.
Zhang, Jie, 2003, The Differentiation of Bone Marrow Mesenchymal Stem Cells into Retina in Rat Eye and the Therapeutical Effect on Severe Injured Retina, A Doctoral Thesis of Chinese PLA Acadamey of Military Medical Sciences, 1-127, 1-127.
Zhang_et_al, 2009, Highly Efficient Differentiation of Human ES Cells and iPS Cells into Mature Pancreatic Insulin-Producing Cells, Cell Research, vol. 19, Issue 14, pp. 429-438.
Zhao, et al., Jul. 2009, Derivation and Characterization of Hepatic Progenitor Cells from Human Embryonic Stem Cells, PLoS ONE Hepatic Progenitors from hESCs, vol. 4, Issue 7, e6468 pp. 1-10.
Zorn, et al., 2009, Vertebrate Endoderm Development and Organ Formation, Annual Review Cell Development Biology, vol. 25, pp. 221-251.
Zubaty, et al., 2005, Transplantation of Mesenchymal Stem Cells into Rcs Rats for Retinal Repair, Investigative Ophthalmology and Visual Science, vol. 46, Supplement S, pp. 4160-B518.
Abeyta, et al., Unique Gene Expression Signatures of Independently-Derived Human Embryonic Stem Cells Lines, Human Molecular Genetics, Jan. 28, 2004, pp. 601-608, vol. 13, No. 6, Oxford University Press.
Abranches, et al., Expansion of Mouse Embryonic Stem Cells on Microcarriers, Biotechnology Bioengineering, Apr. 15, 2007, pp. 1211-1221, vol. 96, No. 6, Wiley InterScience.
Allegrucci, et al., Differences between Human Embryonic Stem Cell Lines, Human Reproduction Update, Aug. 26, 2006, pp. 1-18, Advance Access.
Amit, et al., Clonally Derived Human Embryonic Stem Cell Lines Maintain Pluripotency and Proliferative Potential for Prolonged Periods of Culture, Developmental Biology, 2000, pp. 271-278, vol. 227.
Amit, et al., Feeder Layer-and Serum-Free Culture of Human Embryonic Stem Cells, Biology of Reproduction, 2004, pp. 837-845, vol. 70.
Arai, et al., Purification of Recombinant Activin A Using the Second Follistatin Domain of Follistatin-Related Gene (FLRG), Protein Expression & Purification, 2006, pp. 78-82, vol. 49.

Armstrong, et al., The Role of P13K/AKT, MAPK/ERK and $NF_{\kappa\beta}$ Signalling in the Maintenance of Human Embryonic Stem Cell Pluripotency and Viability Highlighted by Transcriptional Profiling and Functional Analysis, Human Molecular Genetics, 2006, pp. 1894-1913, vol. 15, No. 11.
Baetge, Production of B-Cells from Human Embryonic Stem Cells, Diabetes, Obesity, Metabolism, 2008, pp. 186-194, vol. 10, Supplement 4.
Balsam, et al., Haematopoeitic Stem Cells Adopt Mature Haeatopoietic Fates in Ischaemic Myocardium, Nature, Apr. 8, 2004, pp. 668-673, ?, Nature Publishing Group.
Barclay, et al., The Leucocyte Antigen Facts Book, The Leucocyte Antigen Facts Book, 1997, Textbook, 2[sup] edition, Academic Press.
Beltrami, et al., Adult Cardiac Stem Cells are Multipotent and Support Myocardial Regeneration, Cell, Sep. 19, 2003, pp. 763-776, vol. 114, Cell Press.
Bigdeli, et al., Adaptation of Human Embryonic Stem Cells to Feeder-Free and Matrix-Free Culture Conditions Directly on Plastic Surfaces, Journal of Biotechnology, 2008, pp. 146-153, vol. 133.
Blin, et al., A Purified Population of Multipotent Cardiovascular Progenitors Derived from Primate Pluripotent Stem Cells Engrafts in Postmyocardial Infarcted Nonhumans Primates, The Journal of Clinical Investigation, Apr. 2010, pp. 1125-1139, vol. 120, No. 4.
Bocian-Sobkowska, et al., Polyhormonal Aspect of the Endocrine Cells of the Human Fetal Pancreas, Histochem Cell Biol, 1999, pp. 147-153, vol. 112, Issue 2.
Borowiak, et al., How to Make AB Cells, Current Opinion Cell Biology, 2009, pp. 727-732, vol. 21, Issue 6.
Borowitz, et al., Prognostic Significance of Fluorescence Intensity of Surface Marker . . ., Blood, Jun. 1, 1997, 3960-3966, 89-11, American Society of Hematology, Washington, D.C., US.
Braam, et al., Improved Genetic Manipulation of Human Embryonic Stem Cells, Nature Methods, May-2008, pp. 389-392, vol. 5, No. 5.
Brakenhoff et al., Development of a Human Interleukin-6 Receptor Antagonist, Journal of Biological Chemistry, Jan. 7, 1994, 86-93, 269-1, US.
Brevig, et al., The Recognition of Adsorbed and Denatured Proteins of Different Topographies by β2 Integrins and Effects on Leukocyte Adhesion and Activation, Biomaterials, 2005, pp. 3039-3053, vol. 26.
Brevini, et al., No Shortcuts to Pig Embryonic Stem Cells, Theriogenology, 2010, pp. 544-550, vol. 74.
Brown, et al., Optimal Control of Blood Glucose: The Diabetic Patient or the Machine?, Science Translation Medicine, Apr. 14, 2010, pp. 1-5, vol. 2 Issue 27.
Burkard et al, Conditional Neuronal Nitric Oxide Synthase Overexpression Impairs Myocardial Contractility, Circulation Reseach, Jan. 18, 2007, pp. e32-e44, vol. 100.
Buzzard et al., Karyotype of human ES cells during extended culture, Nature Biotechnology, Apr. 1, 2004, 381-382, 22-4, Nature Publishing Group.
Cai, et al., Generation of Homogeneous PDX1+Pancreatic Progenitors from Human ES Cell-derived Endoderm Cells, Journal of Molecular Cell Biology, Nov. 12, 2009, pp. 50-60, vol. 2.
Castaing, et al., Blood Glucose Normalization Upon Transplantation of Human Embryonic Pancreas into Beta Cell-Deficient SCID Mice, Diabetologica, 2001, pp. 2066-2076, vol. 44.
Chambers, et al., Functional Expression Cloning of Nanog, a Pluripotency Sustaining Factor in Embryonic Stem Cells, Cell, May 30, 2003, pp. 643-655, vol. 113.
Chapple, et al., Unfolding Retinal Dystrophies: A Role for Molecular Chaperones?, Trends in Molecluar Medicine, 2001, pp. 414-421, vol. 7, No. 9.
Chen, et al., A Small Molecule that Directs Differentiation of Human ESCs into the Pancreatic Lineage, Nature Chemical Biology, Apr. 11, 2009, pp. 258-265, vol. 5, No. 4.
Chen, et al., Chemically Defined Conditions for Human iPSC Derivation and Culture, Nature Methods, 2011, pp. 424-429, vol. 8, Issue 5.
Chen, et al., Differentiation of Rat Marrow Mesencymal Stem Cells in Pancreatic Islet Beta-Cells, World Journal of Gastroenterology, Oct. 15, 2004, 3016-3020, 10.

(56) References Cited

OTHER PUBLICATIONS

Chung, et al., Human Embryonic Stem Cell Lines Generated without Embryo Destruction, Cell Stem Cell, 2008, pp. 113-117, vol. 2.
Corbeil, et al., Rat Prominin, Like its Mouse and Human Orthologues, is a Pentaspan Membrane Glycoprotein, Biochemical and Biophysical Research Communications, 2001, pp. 939-944, vol. 285, No. 4.
Crane, et al., An Embryogenic Model to Explain Cytogenetic Inconsistencies Observed in Chorionic Villus Versus Fetal Tissue, Prenatal Diagnosis, 1988, pp. 119-129, vol. 8.
Cure, et al., Improved Metabolic Control and Quality of Life in Seven Patients with Type 1 Diabetes Following Islet After Kidney Transplantation, Cell Therapy and Islet Transplantation, Mar. 27, 2008, pp. 801-812, vol. 85, No. 6.
David M. Chacko, et al., Survival and Differentiation of Cultured Retinal Progenitors Transplanted in the Subretinal Space of the Rat, Biochemical and Biophysical Research Communications, 2000, pp. 842-846, vol. 268, Academic Press.
De Rosa, 11-color, 13-parameter flow cytometry: Identification of . . ., Nature, Feb. 1, 2001, 245-248, 7-2, Nature Publishing Group, US.
Denning, et al., Common Culture Conditions for Maintenance and Cardiomyocyte Differentiation of the Human Embryonic Stem Cell Lines, BG01 and HUES-7, Int. J. Del. Biol., 2006, pp. 27-37, vol. 50.
Deramaudt, et al., The PDX1 Homeodomain Transcription Factor Negatively Regulates the Pancreatic Ductal Cell-specific Keratin 19 Promoter*, Journal of Biological Chemistry, 2006, pp. 38385-38395, vol. 281, No. 50.
Donovan, et al., The End of the Beginning for Pluripotent Stem Cells, Nature, Nov. 2001, pp. 92-97, vol. 414.
Dorrell, et al., Editorial, Stem Cell Research, 2008, pp. 155-156, vol. 1.
Doyle, et al., Cell and Tissue Culture: Laboratory Procedures in Biotechnology, Cell and Tiossue Culture: Laboratory Procedures in Biotechnology, 1995, Textbook, Textbook, Wiley.
Draper, et al., Recurrent Gain of Chromosomes 17q and 12 in Cultured Human Embryonic Stem Cells, Nature Biotechnology, 2004, pp. 53-54, vol. 22, No. 1.
Draper, et al., Surface Antigens of Human Embryonic Stem Cells: Changes Upon Differentiation in Culture, Journal Anatomy, 2002, pp. 249-258, vol. 200, Anatomical Society of Great Britain and Ireland.
Dupont-Gillain, et al., Plasma-Oxidized Polystyrene: Wetting Properties and Surface Reconstruction, Langmuir, 2000, pp. 8194-8200, vol. 16.
Ellerstrom, et al., Derivation of a Xeno-Free Human Embryonic Stem Cell Line, Stem Cells, 2006, pp. 2170-2176, vol. 24.
Ellerstrom, et al., Facilitated Expansion of Human Embryonic Stem Cells by Single-Cell Enzymatic Dissociation, Stem Cells, 2007, pp. 1690-1696, vol. 25, No. 7.
Ellmers, et al., Transforming Growth Factor-B Blockade Down-Regulates the Renin-Angiotensin System and Modifies Cardiac Remodling after Myoardial Infarction, Endocrinology, Jul. 24, 2008, pp. 5828-5834, vol. 149-Issue 11, The Endocrine Society.
Enzmann, et al., Enhanced Induction of RPE Lineage Markers in Pluripootent Neural Stem Cells Engrafted into the Adult Rat Subretinal Space, Ophthamology & Visual Science, Dec. 2003, pp. 5417-5422, vol. 44, No. 12, Association for Research in Vision and Ophthamology.
Eventov-Friedman, et al., Embryonic Pig Pancreatic Tissue Transplantation for the Treatment of Diabetes, PLoS Medicine, Jul. 2006, e215, pp. 1165-1177, vol. 3, Issue 7.
Ezashi, et al., Low 02 Tensions and the Prevention of Differentiation of hES Cells, Proceedings of the National Academy of Sciences of USA, Mar. 29, 2005, pp. 4783-4788, vol. 102, No. 13.
Fauza, Amniotic Fluid and Placental Stem Cells, Ballieres Best Practice and Research Clinical Obsterics and Gynaecology, 2004, pp. 877-891, vol. 18, No. 6.
Fidler et al., Selective Immunomodulation by the Antineoplastic Agent Mitoxantrone, Journal of Immunology, Jul. 15, 1986, 727-732, 137-2, American Society of Immunologists, US.
Fischer, et al., Residues in the C-Terminal Region of Activin A Determine Specificity for Follistatin and Type II Receptor Binding, Journal of Endocrinology, 2003, pp. 61-68, vol. 176, Society for Endocrinology.
Fok, et al., Shear-Controlled Single-Step Mouse Embryonic Stem Cell Expansion and Embryoid Body-Based Differentiation, Stem Cells, 2005, pp. 1333-1342, vol. 23.
Frandsen et al., Activin B mediated induction of Pdx1 in human embryonic stemcell derived embryoid bodies, Biochemical and Biophysical Research Communications, Aug. 15, 2007, 568-574, 362, Elsevier Inc.
Fung, et al., The Effect of Medical Therapy and Islet Cell Transplantation on Diabetic Nephropathy: An Interim Report, Transplantation, Jul. 15, 2007, pp. 17-22, vol. 84, No. 1.
Gaspar, et al., Inhibition of Transforming Growth Factor Signaling Reduces Pancreatic Adenocarcinoma Growth and Invasiveness, Molecular Pharmacology, 2007, pp. 152-161, vol. 72, Issue 1.
Giltaire, et al., The CYP26 Inhibitor R115866 Potentiates the Effects of All-Trans Retinoic Acid on Cultured Human Epidermal Keratinocytes, British Journal of Dermatology, 2009, pp. 505-513, vol. 160.
Ginis, et al., Differences Between Human and Mouse Embryonic Stem Cells, Developmental Biology, 2004, pp. 360-380, vol. 269.
Gosden, et al., Amniotic Fluid Cell Types and Culture, British Medical Bulletin, 1983, pp. 348-354, vol. 39, No. 4.
Graham, et al., Characteristics of a Human Cell Line Transformed by DNA from Human Adenovirus Type 5, Journal General Virology, 1977, pp. 59-72, vol. 36.
Guo, et al., Stem Cells to Pancreatic B-Cells: New Sources for Diabetes Cell Therapy, Endocrine Reviews, May 2009, pp. 214-227, vol. 30, No. 3, The Endocrine Society.
Hamann, et al., Phenotypic and Functional Separation of Memory and and Effector Human CD8+ T Cells, Journal of Experimental Medicine, Mar. 11, 1997, 1407-1418, 186-9, Rockefeller University Press, US.
Harb, et al., The Rho-Rock-Myosin Signaling Axis Determines Cell-Cell Integrity of Self-Renewing Pluripotent Stem Cells, Plos One, 2008, Article e3001, XP002530386, vol. 3, Issue 8.
Haruta, et al., In Vitro and In Vivo Characterization of Pigment Epithelieal Cells Differentiated from Primate Embryonic Stem Cells, Investigative Ophthalmology & Visual Science, Mar. 2004, pp. 1020-1025, vol. 45, No. 3, Association for Research in Vision and Ophthalmology.
Hasegawa, et al., A Method for the Selection of Human Embryonic Stem Cell Sublines with High Replating Efficiency After Single-Cell Dissociation, Stem Cells, 2006, pp. 2649-2660, vol. 24.
Hashemi, et al., A Placebo Controlled, Dose-Ranging, Safety Study of Allogenic Mesenchymal Stem Cells Injected by Endomyocardial Delivery after an Acute Myocardial Infarction, European Heart Journal, Dec. 11, 2007, pp. 251-259, vol. 29.
Held, et al., The Effect of Oxygen Tension on Colony Formation and Cell Proliferation of Amniotic Fluid Cells In-Vitro, Prenatal Diagnosis, 1984, pp. 171-180, vol. 4, No. 3.
Henderson, et al., Preimplantation Human Embryos and Embryonic Stem Cells Show Comparable Expression of Stage-Specific Embryonic Antigens, Stem Cells, 2002, pp. 329-337, vol. 20.
Heng, et al., Mechanical dissociation of human embryonic stem cell colonies by manual scraping after collagenase treatment is much more detrimental to cellular viability than is trypsinization with gentle pipetting, Biotechnol. Appl. Biochem., 2007, 33-37, 47, Portland Press Ltd., GB.
Herzenberg, et al., Fluorescence-activated Cell Sorting, Scientific American, 1976, 108-117, 234, Scientific American, US.
Hess, et al., Bone Marrow-Derived Stem Cells Initiate Pancreatic Regeneration, Nature Biotechnology, Jul. 2003, pp. 763-770, vol. 21, No. 7.
Ho, et al., Animal Cell Bioreactors, Animal Cell Bioreactors, 1991, 1-512, Hardcover, Butterworth-Heinemann.
Hoehn, et al., Morphological and Biochemical Heterogeneity of Amniotic Fluid Cells in Culture, Methods in Cell Biology, 1982, pp. 11-34, vol. 26, Academic Press, Inc.
Hussain, et al., Stem-Cell Therapy for Diabetes Mellitus, Lancet, 2004, pp. 203-205, vol. 364.

(56) References Cited

OTHER PUBLICATIONS

Ianus, et al., In Vivo Derivation of Glucose-Competent Pancreatic Endocrine Cells from Bone Marrow Without Evidence of Cell Fusion, The Journal of Clinical Investigation, Mar. 2003, pp. 843-850, vol. 111, No. 6.

Inami, et al., Differentiation of Induced Pluripotent Stem Cells to Thymic Epithelial Cells by Phenotype, Immunology and Cell Biology, Jun. 24, 2010, pp. 1-8, doi:10.1038/icb.2010.96.

Int' Anker, et al., Amniotic Fluid as a Novel Source of Mesenchymal Stem Cells for Therapeutic Transplantation, Blood, Aug. 15, 2003, pp. 1548-1549, vol. 102, No. 4.

Itkin-Ansari, et al., Cell-Based Therapies for Diabetes: Progress Towards a Transplantable Human B Cell Line, Annals of the New York Academy of Sciences, 2003, pp. 138-147, vol. 1005, No. 1.

Jafary, et al., Differential effect of activin on mouse embryonic stem cell differentiation in insulin-secreting cells under nestin-positive selection and spontaneous differentiation protocols, Cell Biology International, 2008, 278-286, 32, Elsevier.

Jeon, et al., Endocrine Cell Clustering During Human Pancreas Development, J Histochem Cytochem, 2009, pp. 811-824, vol. 57, Issue 9.

Jiang, et al., Generation of Insulin-Producing Islet-Like Clusters from Human Embryonic Stem Cells, Stem Cells, 2007, pp. 1940-1953, vol. 25, Issue 8.

Johansson, et al., Temporal Control of Neurogenin3 Activity in Pancreas Progenitors Reveals Competence Windows for the Generation of Different Endocrine Cell Types, Developmental Cell, Mar. 2007, pp. 457-465, vol. 12.

Kahan, Pancreatic Precursors and Differentiated Islet Cell Types from Murine Embryonic Stem Cells, Diabetes, Aug. 2003, pp. 2016-2042, vol. 52.

Kelly, et al., Cell-Surface Markers for the Isolation of Pancreatic Cell Types Derived from Human Embryonic Stem Cells, Nature Biotechnology, 2011, pp. 750-756, vol. 29, Issue 8.

Kicic, et al., Differentiation of Marrow Stromal Cells into Photoreceptors in the Rat Eye, The Journal of Neuroscience, Aug. 27, 2003, pp. 7742-7749, vol. 23, Issue 21.

Kingsley, The TGF-B Superfamily: New Members, New Receptors, and New Genetic Tests of Function in Different Organisms, Genes & Development, 1994, pp. 133-146, XP009011502, vol. 8, Cold Spring Harbor Laboratory Press.

Kinkel, et al., Cyp26 Enzymes Function in Endoderm to Regulate Pancreatic Field Size, PNAS, May 12, 2009, pp. 7864-7869, vol. 106, No. 19.

Klimanskaya, et al., Human Embryonic Stem Cells Derived without Feeder Cells, Lancet, May 2005, pp. 1636-1641, vol. 365, No. 9471.

Koblas, et al., Differentiation of CD133-Positive Pancreatic Cells Into Insulin-Producing Islet-Like Cell Clusters, Transplantation Proceedings, 2008, pp. 415-418, vol. 40.

Kohen, et al., Characterization of Matrigel Interfaces During Defined Human Embryonic Stem Cell Culture, Characterization of Matrigel Interfaces During Defined Human Embryonic Stem Cell Culture, Sep. 3, 2010, pp. 6979, vol. 4.

Koller, et al., Effects of Synergistic Cytokine Combinations, Low Oxygen, and Irradiated Stroma on the Expansion of Human Cord Blood Progenitors, Blood, Jul. 15, 1992, pp. 403-411, vol. 80, No. 2.

Koyangi et al., Inhibitio not the Rho/ROCK Pathway Reduces Apoptosis During Transplantatation of Embryonic Stem Cell-Derived Neural Precursors, Journal of Neuroscien Research, Sep. 7, 2007, 270-280, 86, Wiley-Liss, Inc.

Krapcho et al., Synthesis and Antineoplastic Evaluations of 5,8-Bis[(aminoalkyl)amino]-1-azaanthracene-9,10-diones, Journal of Medical Chemistry, 1985, 1124-1126, 28, American Chemical Society.

Krawetz, et al., Human Embryonic Stem Cells: Caught Between a ROCK Inhibitor and a Hard Place, BioEssays: News and Reviews in Molecular Cellular and Developmental Biology, 2009, pp. 336-343, vol. 31.

Kron, et al., Expression of Human Activin C Protein in Insect Larvae Infected with a Recombinant Baculovirus, Journal of Virological Methods, 1998, pp. 9-14, vol. 72.

Kroon, et al., Pancreatic Endoderm Derived from Human Embryonic Stem Cells Generates Glucose-Responsive Insulin-Secreting Cells in vivo, Nature Biotechnology, Apr. 2008, pp. 443-452, vol. 26, No. 4.

Ku et al., Committing Embryonic Stem Cells to Early Endocrine Pancreas In Vitro, Stem Cells, 2004, 1205-1217, 22, AlphaMed Press.

Lanza, et al., Characteristics and Characterization of Human Pluripotent Stem Cells, Stem Cell Anthology, 2010, pp. 141, 142, 144 and 146, 1st Edition.

Laplante, et al., RhoA/ROCK and Cdc42 Regulate Cell-Cell Contact and N-Cadherin Protein Level During Neurodetermination of P19 Embryonal Stem Cells, Journal of Neurobiology, 2004, pp. 289-307, vol. 60, No. 3.

Larsen, et al., Evaluation of B-Cell Mass and Function in the Gottingen Minipig, Diabetes, Obesity and Metabolism, 2007, pp. 170-179, vol. 9, Supplement 2, Blackwell Publishing Ltd.

Le Blanc, et al., Mesenchymal Stem Cells Inhibit and Stimulate Mixed Lymphocyte Cultures and Mitogenic Responses Independently of the Major Histocompatibility Complex, Scandinavian Journal of Immunology, 2003, pp. 11-20, vol. 57, Blackwell Publishing Ltd.

Lee, et al., Human B-cell Precursors Mature into Functional Insulin-Producing Cells in an Immunoisolation Device: Implications for Diabetes Cell Thereapies, Transplantation, Apr. 15, 2009, pp. 983-991, vol. 87, No. 7.

Li, et al., Generation of Rat and Human Induced Pluripotent Stem Cells by Combining Genetic Reprogramming and Chemical Inhibitors, Cell Stem Cell, Jan. 9, 2009, pp. 16-19, vol. 4.

Lim, et al., Proteome Analysis of Conditioned Medium from Mouse Embryonic Fibroblast Feeder Layers which Support the Growth of Human Embryonic Stem Cells, Proteomics, 2002, pp. 1187-1203, vol. 2.

Liu, et al., A Novel Chemical-Defined Medium with bFGF and N2B27 Supplements Supports Undifferentiated Growth in Human Embryonic Stem Cells, Biochemical and Biophysical Research Communications, 2006, pp. 131-139, vol. 346.

Loh, et al., Genomic Approaches to Deconstruct Puripotency, Annu Rev Genomics Hum Genet, 2011, pp. 165-185, vol. 12.

Ludwig, et al., Derivation of Human Embryonic Stem Cells in Defined Conditions, Nature Biotechnology, Feb. 2006, pp. 185-187, vol. 24 No. 2.

Lund, et al., Cell Transplantation as a Treatment for Retinal Disease, Progress in Retinal and Eye Research, 2001, pp. 415-449, vol. 20, No. 4, Elsevier Science Ltd.

Lund, et al., Retinal Transplantation: Progress and Problems in Clinical Application, Journal of Leukocyte Biology, Aug. 2003, pp. 151-160, vol. 74.

Lyttle, et al., Transcription Factor Expression in the Developing Human Fetal Endocrine Pancreas, Diabetologica, 2008, pp. 1169-1180, vol. 51, Spring-Verlag.

Maherali, et al., Directly Reprogrammed Fibroblasts Show Global Epigenetic Remodeling and Widespread Tissue Contribution, Cell Stem Cell, Jul. 2007, pp. 55-70, vol. 1, Elsevier, Inc.

Marshall, et al., Early Micro-and Macro-Angiopathy in the Streptozotocin, Research in Experimental Medicine, 1980, pp. 145-158, vol. 177, Springer-Verlag.

Marshall, et al., Isolation and Maintenance of Primate Embryonic Stem Cells, Methods in Molecular Biology, 2001, pp. 11-18, vol. 158.

Martin, et al., Bioreactors for Tissue Mass Culture: Design, Characterization, and Recent Advances, Biomaterials, Jul. 14, 2005, pp. 7481-7503, vol. 26.

McKiernan, et al., Directed Differentiation of Mouse Embryonic Stem Cells into Pancreatic-Like or Neuronal-and Glial-Like Phenotypes, Tissue Engineering, 2007, pp. 2419-2430, vol. 13, No. 10.

McLin et al., Repression of WNT(szligbeta)-6atenin Signaling in the Anterior Endoderm is Essential for Liver and Pancreas Development, Development, 2007, pp. 2207-2217, vol. 134, Issue 12.

Meijer, et al., Pharmacological Inhibitors of Glycogen Synthase Kinase 3, Trends in Pharmacological Sciences, Sep. 2004, pp. 471-480, vol. 25, No. 9.

(56) References Cited

OTHER PUBLICATIONS

Miller, et al., The Pig as a Model for Human Nutrition, Annual Review of Nutrition, 1987, pp. 361-382, vol. 7, Annual Reviews Inc.
Milunsky, et al., Genetic Disorders and the Fetus: Diagnosis Prevention and Treatment, Pediatric and Developmental Pathology, 2011, pp. 84, vol. 14, Society for Pediatric Pathology.
Mitalipova, et al., Preserving the Genetic Integrity of Human Embyonic Stem Cells, Nature Biotechnology, 2005, pp. 19-20, vol. 23, No. 1.
Mitsui, et al., The Homeoprotein Nanog is Required for Maintenance of Pluripotency in Mouse Epiblast and ES Cells, Cell, May 30, 2003, pp. 631-642, vol. 113, Cell Press.
Moore, et al., The Corneal Epithelial Stem Cell, DNA and Cell Biology, 2002, pp. 443-451, vol. 21, No. 5/6.
Morrison, et al., Culture in Reduced Levels of Oxygen Promotes Clonogenic Sympathoadrenal Differentiation by Isolated Neural Crest Stem Cells, Journal of Neuroscience, Oct. 1, 2000, pp. 7370-7376, vol. 20, No. 19.
Movassat, et al., Keratinocyte Growth Factor and Beta-Cell Differentiation in Human Fetal Pancreatic Endocrine Precursor Cells, Diabetologia, 2003, pp. 822-829, vol. 46.
Munoz, et al., Conventional Pluripotency Markers are Unspecific for Bovine Embryonic-Derived Cell-Lines, Theriogenology, 2008, pp. 1159-1164, vol. 69.
Nakagawa, et al., Generation of Induced Pluripotent Stem Cells without Myc from Mouse and Human Fibroblasts, Generation of Induced Pluripotent Stem Cells without Myc from Mouse and Human Fibroblasts, Jan. 2008, pp. 101-106, vol. 26, No. 1.
Nakamura, et al., Ocular Surface Reconstruction Using Cultivated Mucosal Epithelial Stem Cells, Cornea, Oct. 2003, S75-S80, vol. 22, Supplement 1.
Nicholas et al., A Method for Single-Cell Sorting and Expansion of Genetically modified Human Embryonic Stem Cells, Stem Cells and Development, 2007, 109-117, 16, Mary Ann Liebert, Inc.
Nostro, et al., Stage-Specific Signaling Through TGF Family Members and Wnt Regulates Patterning and Pancreatic Specification of Human Pluripotent Stem Cells, Development, 2011, pp. 861-871, vol. 138, Issue 5.
Oh, et al., Human Embryonic Stem Cells: Technological Challenges Towards Therapy, Clinical and Experimental Pharmacology and Physiology, 2006, pp. 489-495, vol. 33.
Okita, et al., Generation of Germline-Competent Induced Pluripotent Stem Cells, Nature, Jul. 19, 2007, pp. 313-317, vol. 448.
Osborne, et al., Some Current Ideas on the Pathogenesis and the Role of Neuroprotection in Glaucomatous Optic Neuropathy, European Journal of Ophthalmology, 2003, S19-S26, vol. 13, Supplement 3, Wichtig Editore.
Ostrom, et al., Retinoic Acid Promotes the Generation of Pancreatic Endocrine Progenitor Cells and Their Further Differentiation into B-Cells, PLOS One, Jul. 30, 2008, e2841, pp. 1-7, vol. 3, No. 7.
Paling, et al., Regulation of Embryonic Stem Cell, Self-Renewal by Phosphoinositide 3-kinase-dependent Signaling, Journal of Biological Chemistry, 2004, pp. 48063-48070, vol. 279, No. 46.
Panchision, et al., Optimized Flow Cytometric Analysis of Central Nervous System Tissue Reveals Novel Functional Relationships Among Cells Expressing CD133, CD15, and CD24, Stem Cells, 2007, pp. 1560-1570, vol. 25.
Panepinto, et al., The Yucatan Miniature Pig: Characterization and Utilization in Biomedical Research, Laboratory Animal Science, Aug. 1986, pp. 344-347, vol. 36, No. 4, American Association for Laboratory Animal Science.
Pangas, et al., Production and Purification of Recombinant Human Inhibin and Activin, Journal of Endocrinology, 2002, pp. 199-210, vol. 172.
Pardo, et al., Corning CellBIND Surface: An Improved Surface for Enhanced Cell Attachment, Corning Technical Report, 2005, 8 page report, XP002530385.
Paris, et al., Equine Embryos and Embryonic Stem Cells: Defining Reliable Markers of Pluripotency, Theriogeneology, 2010, pp. 516-524, vol. 74.
Peerani, et al., Niche-Mediated Control of Human Embryonic Stem Cell Self-Renewal and Differentiation, The EMBO Journal, 2007, pp. 4744-4755, vol. 26.
Phillips, et al., Attachment and Growth of Human Embryonic Stem Cells on Microcarriers, Journal of Biotechnology, 2008, pp. 24-32, vol. 138.
Pouton, et al., Embryonic Stem Cells as a Source of Models for Drug Discovery, Nature Reviews Drug Discovery, Aug. 2007, pp. 1474-1776, vol. 6, No. 8.
Prichard, et al., Adult Adipose Derived Stem Cell Attachment to Biomaterials, Biomaterials, 2006, pp. 936-946, vol. 28, No. 6.
Prowse, et al., A Proteome Analysis of Conditioned Media from Human Neonatal Fibroblasts Used in the Maintenance of Human Embryonic Stem Cells, Proteomics, 2005, pp. 978-989, vol. 5.
Prusa, et al., Oct. 4—Expressing Cells in Human Amniotic Fluid: a New Source for Stem Cell Research?, Human Reproduction, 2003, pp. 1489-1493, vol. 18, No. 7.
Rajagopal, et al., Insulin Staining of ES Cell Progeny from Insulin Uptake, Science, Jan. 17, 2003, pp. 363, vol. 2.
Rao, Conserved and Divergent Paths that Regulate Self-Renewal in Mouse and Human Embryonic Stem Cells, Developmental Biology, Aug. 10, 2004, pp. 269-286, vol. 275, Elsevier, Inc.
Rebollar, et al., Proliferation of Aligned Mammalian Cells on Laser-Nanostructured Polystyrene, Biomaterials, 2008, pp. 1796-1806, vol. 29.
Reisner, Growing Organs for Transplantation form Embryonic Precursor Tissues, Immunol. Res., 2007, pp. 261-273, vol. 38.
Rezania, Production of Functional Glucagon-Secreting-Cells from Human Embryonic Stem Cells, Diabetes, 2011, pp. 239-247, vol. 60, Issue 1.
Ryan, et al., Clinical Outcomes and Insulin Secretion After Islet Transplantation with the Edmonton Protocol, Diabetes, Apr. 2001, pp. 710-719, vol. 50.
Sakaguchi, et al., Integration of Adultmesenchymal Stem Cells in the CNS, Society for Neuroscience Abstract Viewer and Itineray Planner, 2002, XP002519394, Program 237.18.
Sato, et al., Maintenance of Pluripotency in Human and Mouse Embryonic Stem Cells Through Activation of Wnt Signaling by a Pharmacological GSK-3-specific Inhibitor, Nature Medicine, Jan. 2004, pp. 55-63, vol. 10, No. 1.
Sato, et al., Manipulation of Self-Renewal in Human Embryonic Stem Cells Through a Novel Pharmacological GSK-3 Inhibitor, Methods in Molecular Biology, 2006, pp. 115-128, vol. 331.
Sato, et al., Molecular Signature of Human Embryonic Stem Cells and its Comparison with the Mouse, Developmental Biology, Apr. 23, 2003, pp. 404-413, vol. 260.
Savino et al., Generation of Interleukin-6 Receptor Antagonists by Molecular-Modeling Guided Mutagenesis of Residues Important for gp130 Activation, EMBO Journal, 1994, 1357-1367, 13-6, IT.
Schnier, et al., G1 Arrest and Down-Regulation of Cyclin E/cyclin-dependent Kinase 2 by the Protein Kinase Inhibitor Staurosporine are Dependent on the Retinoblastoma Protein in the Bladder Carcinoma Cell Line 5637, Proceedings of the National Academy of Sciences, 1996, pp. 5941-5946, vol. 93.
Schraermeyer, et al., Subretinally Transplanted Embryonic Stem Cells Rescue Photoreceptor Cells From Degeneration in the RCS Rats, Cell Transplantation, 2001, pp. 673-680, vol. 10.
Schroeder, et al., Differentiation of Mouse Embryonic Stem Cells to Insulin-Producing Cells, Nature Protocols, 2005, pp. 495-507, vol. 1, No. 2.
Scullica, et al., Diagnosis and Classification of Macular Degenerations: an Approach Based on Retinal Function Testing, Documenta Ophthalmologica, 2001, pp. 237-250, vol. 102.
Segev, et al., Differentiation of Human Embryonic Stem Cells into Insulin-Producing Clusters, Stem Cells, Jan. 1, 2004, pp. 265-274.
Shapiro, et al., Islet Transplantation in Seven Patients with Type 1 Diabetes Mellitus Using a Glucocorticoid-Free Immunosuppressive Regimen, The New England Journal of Medicine, Jul. 27, 2000, pp. 230-238, vol. 343, No. 4, The Massachusetts Medical Society.
Shen, et al., The Effects of Surface Chemistry and Adsorbed Proteins on Monocyte/Macrophage Adhesion to Chemically Modified Polystyrene Surfaces, Journal of Biomedical Matter Research, 2001, pp. 336-345, vol. 57.

(56) References Cited

OTHER PUBLICATIONS

Sherwood, et al., Transcriptional Dynamics of Endodermal Organ Formation, Developmental Dynamics, 2009, pp. 29-42, vol. 238, Issue 1.

Shi et al., Inducing Embryonic Stem Cells to Differentiate into Pancreatic β Cells by a Novel Three-Step Approach with Activin a and All-Trans Retinoic Acid, Stem Cells, 2005, 656-662, 23, AlphaMed Press.

Shindler et al., A synthetic nanofibrillar matrix promotes in vivo-like organization and morphogenesis for cells in culture, Biomaterials, Apr. 18, 2005, 5624-5631, 26, Elsevier.

Shiraki, et al., Guided Differentiation of Embryonic Stem Cells into Pdx1-Expressing Regional-Specific Definitive Endoderm, Stem Cells, 2008, pp. 874-885, vol. 26.

Sidhu et al., Derivation of Three Clones from Human Embryonic Stem Cell Lines by Facs Sorting and Their Characterization, Stem Cells and Development, 2006, 61-69, 15, Mary Ann Liebert, Inc.

Simons, et al., Assembly of Protein Tertiary Structures from Fragments with Similar Local Sequences Using Simulated Annealing and Bayesian Scoring Functions, Journal of Molecular Biology, 1997, pp. 209-225, vol. 268.

Simons, et al., Improved Recognition of Native-Like Protein Structures Using a Combination of Sequence-Dependent and Sequence-Independent Features of Proteins, Proteins: Structure, Function, and Genetics, 1999, pp. 82-95, vol. 34, Wiley-Liss, Inc.

Smith et al., Anti-Interleukin-6 Monocolnal Antibody Induces Regression of Human Prostate Cancer Xenografts in Nude Mice, The Prostate, Mar. 2, 2001, 47-53, 48, Wiley-Liss, Inc.

Stadtfeld, et al., Defining Molecular Cornerstones During Fibroblast to iPS Cell Reprogramming in Mouse, Cell Stem Cell, Mar. 2008, pp. 230-240, vol. 2.

Stafford, et al., Retinoic Acid Signaling is Required for a Critical Early Step in Zebrafish Pancreatic Development, Current Biology, 2002, pp. 1215-1220, vol. 12, Issue 14.

Sugiyama, et al., Conserved Markers of Fetal Pancreatic Epithelium Permit Prospective Isolation of Islet Progenitor Cells by FACS, PNAS, Jan. 2, 2007, pp. 175-180, vol. 104, No. 1.

Sugiyama, et al., Fluorescence-Activated Cell Sorting Purification of Pancreatic Progenitor Cells, Diabetes, Obesity and Metabolism, 2008, pp. 179-185, vol. 10, Supplement 4.

Suh, et al., Characterization of His-X3-His Sites in a-Helices of Synthetic Metal-Binding Bovine Somatotropin, Protein Engineering, 1991, pp. 301-305, vol. 4, No. 3.

Takahashi, et al., Homogenous Seeding of Mesenchymal Stem Cells into Nonwoven Fabric for Tissue Engineering, Tissue Engineering, 2003, pp. 931-938, vol. 9, No. 5.

Takahashi, et al., Induction of Pluripotent Stem Cells from Adult Human Fibroblasts by Defined Factors, Cell, 2007, pp. 861-872, vol. 131.

Takehara, et al., Rho-Associate Kinase Inhibitor Y-27632 Promotes Survival of Cynomolgus Monkey Embryonic Stem Cells, Molecular Human Reproduction, 2008, pp. 627-634, vol. 14, No. 11.

Tang, et al., Reprogramming Liver-Stem WB Cells into Functional Insulin-Producing Cells by Persistent Expression of Pdx1-and Pdx1-VP16 Mediated by Lentiviral Vectors, Laboratory Investigation, 2006, pp. 83-93, vol. 86.

Tannock, et al., Chemotherapy with Mitoxantrone Plus Prednisone or Prednisone Alone for Symptomatic Hormone-Resistant Prostate Cancer: A Canadian Randomized Trial With Palliative End Points, Journal of Clinical Oncology, 1996, 1756-1764, 14-6, American Society of Clinical Oncology, US.

Teare, et al., Cellular Attachment to Ultraviolet Ozone Modified Polystyrene Surfaces, Langmuir, 2000, pp. 2818-2824, vol. 16.

Tomita, et al., Bone Marrow-Derived Stem Cells Can Differentiate into Retinal Cells in Injured Rat Retina, Stem Cells, 2002, pp. 279-283, vol. 20.

Tsai, et al., Isolation of Human Multipotent Mesenchymal Stem Cells from Second-Trimester Amniotic Fluid Using a Novel Two-Stage Culture Protocol, Human Reproduction, Apr. 22, 2004, pp. 1450-1456, vol. 19, No. 6.

Uludag, et al., Technology of Mammalian Cell Encapsulation, Advanced Drug Delivery Reviews, 2000, pp. 29-64, vol. 42.

Ungrin, et al., Reproducible, Ultra High-Throughput Formation of Multicellular Organization from Single Cell Suspension-Derived Human Embryonic Stem Cell Aggregates, Plos ONE, 2008, e1565, pp. 1-12, vol. 3, Issue 2.

Vacanti, et al., Selective Cell Transplantation Using Bioabsorbable Artificial Polymers as Matrices, Journal of Pediatric Surgery, Jan. 1988, 3-9, 23-1.

Valet, et al., Pretherapeutic Identification of High-Risk Acute Myeloid Leukemia (AML) Patients from . . ., Clinical Cytometry, Feb. 17, 2003, 4-10, 53B, Wiley-Liss, Inc., US.

Vallier, et al., Activin/Nodal and FGF Pathways Cooperate to Maintain Pluripotency of Human Embryonic Stem Cells, Journal of Cell Sciences, 2005, pp. 4495-4509, vol. 118.

Van Der Greef et al., Rescuing drug discovery: in vivo systems pathology and systems pharmacology, Nature, Dec. 1, 2005, 961-967, 4-1, Nature Reviews, US.

Van Der Windt, et al., The Chioce of Anatomical Site for Islet Transplantation, Cell Transplantation, 2008, pp. 1005-1014, vol. 17.

Van Kooten, et al., Plasma-Treated Polystyrene Surfaces: Model Surfaces for Studying Cell-Biomaterial Interactions, Biomaterials, 2004, pp. 1735-1747, vol. 25.

Van Wachem, et al., 1990, Method for the Fast Application of an Evenly Distributed Cell Layer on Porous Vascular Grafts, Biomaterials, 1990, pp. 602-606, vol. 11.

Vodicka, et al., The Miniature Pig as an Animal Model in Biomedical Research, Annals New York Academy of Sciences, 2005, pp. 161-171, vol. 1049.

Vunjak-Novakovic, et al., Dynamic Cell Seeding of Polymer Scaffolds for Cartilage Tissue Engineering, Biotechnology Program, 1998, pp. 193-202, vol. 14, Issue 2.

Wang et al., Derivation and Growing Human Embryonic Stem Cells on Feeders Derived from Themselves, Stem Cells, 2005, 1221-1227, 23, AlphaMed Press.

Wang et al., Relationship of Chemical Structurs of Anthraquinones with their Effects onthe Suppression of Immune Responses, International Journal of Immunopharmacology, 1987, 733-739, 9-6, International Society for Immunopharmacology, GB.

Wang, et al., Noggin and bFGF Cooperate to Maintain the Pluripotency of Human Embryonic Stem Cells in the Absence of Feeder Layers, Biochemical and Biophysical Research Communications, 2005, pp. 934-942, vol. 33, No. 3.

Watanabe, et al., A Rock Inhibitor Permits Survival of Dissociated Human Embryonic Stem Cells, Nature Biotechnology, 2007, pp. 681-686, vol. 25, No. 6.

Wei, et al., Human Amnion-Isolated Cells Normalize Blood Glucose in Strepozotocin Induced Diabetic Mice, Cell Transplantation, 2003, pp. 545-552, vol. 12, No. 5.

Wells, et al., Early Mouse Endoderm is Patterned by Soluble Factors from Adjacent Germ Layers, Development, pp. 1563-1572, vol. 127, Issue 8.

Wernig, et al., c-Myc is Dispensable for Direct Reprogramming of Mouse Fibroblasts, Cell Stem Cell, Jan. 2008, pp. 10-12, vol. 2.

Wiles et al., Embryonic Stem Cell Development in a Chemically Defined Medium, Experimental Cell Research, 1999, 241-248, 247, Academic Press.

Wilson, et al., The HMG Box Transcription Factor Sox4 Contributes to the Development of the Endcrine Pancreas, Diabetes, 2005, pp. 3402-4309, vol. 54, Issue 12.

Xu, et al., Basic FGF and Suppression of BMP Signalling Sustain Undifferentiated Proliferation of Human ES Cells, Nature Methods, 2005, pp. 185-189, vol. 2, Issue 3.

Xu, et al., Feeder-free Growth of Undifferentiated Human Embryonic Stem Cells, Nature Biotechnology, 2001, pp. 971-974, vol. 19.

Yang et al., Novel cell immobilization method utilizing centrifugal force to achieve high-density hepatocyte culture in porous scaffold, Journal of Biomed Materials Research, Feb. 27, 2001, 379-386, 55, John Wiley & Sons, Inc.

(56) References Cited

OTHER PUBLICATIONS

Yang, et al., Survival of Pancreatic Islet Xenografts in NOD Mice with the Theracyte Device, Transplantation Proceedings, 2002, pp. 3349-3350, vol. 34.

Yasuda, et al., Development of Cystic Embryoid Bodies with Visceral Yolk-Sac-Like Structures from Mouse Embryonic Stem Cells Using Low-Adherence 96-Well Plate, Journal of Bioscience and Bioengineering, Apr. 4, 2009, pp. 442-44, vol. 107, No. 4.

Yoneda, et al., The Rho Kinases I and II Regulate Different Aspects of Myosin II Acitivity, The Journal of Cell Biology, 2005, pp. 443-445, vol. 170, No. 3.

Young, et al., Three-Dimensional Culture of Human Uterine Smooth Muscle Nyocytes on a Resorbably Scaffolding, Tissue Engineering, 2003, pp. 451-459, vol. 9, No. 3.

Yu, et al., Induced Pluripotent Stem Cell Lines Derived from Human Somatic Cells, Science, Dec. 21, 2007, pp. 1917-1920, vol. 318.

Yu, et al., Isolation of a Novel Population of Multipotent Adult Stem Cells from Human Hair Follicles, American Journal of Pathology, Jun. 6, 2006, pp. 1879-1888, vol. 168, No. 6.

Zhang, et al., Differentiation Potential of Bone Marrow Mesenchymal Stem Cells into Retina in Normal and Laser-Injured Rat Eye, Science in China Series, 2004, pp. 241-250, vol. 47, No. 3.

Zhang, Jie, The Differentiation of Bone Marrow Mesenchymal Stem Cells into Retina in Rat Eye and the Therapeutical Effect on Severe Injured Retina, A Doctoral Thesis of Chinese PLA Acadamey of Military Medical Sciences, 2003, 1-127, 1-127.

Zhang_et_al, Highly Efficient Differentiation of Human ES Cells and iPS Cells into Mature Pancreatic Insulin-Producing Cells, Cell Research, 2009, pp. 429-438, vol. 19, Issue 14.

Zhao, et al., Derivation and Characterization of Hepatic Progenitor Cells from Human Embryonic Stem Cells, PLoS ONE Hepatic Progenitors from hESCs, Jul. 2009, e6468 pp. 1-10, vol. 4, Issue 7.

Zorn, et al., Vertebrate Endoderm Development and Organ Formation, Annual Review Cell Development Biology, 2009, pp. 221-251, vol. 25.

Zubaty, et al., Transplantation of Mesenchymal Stem Cells into RCS Rats for Retinal Repair, Investigative Ophthalmology and Visual Science, 2005, pp. 4160-B518, vol. 46, Supplement S.

* cited by examiner

Insulin/Glucagon

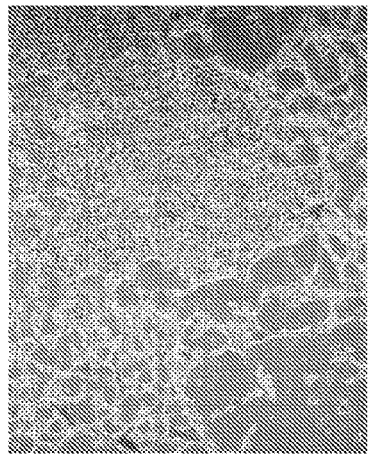
FIG. 2C
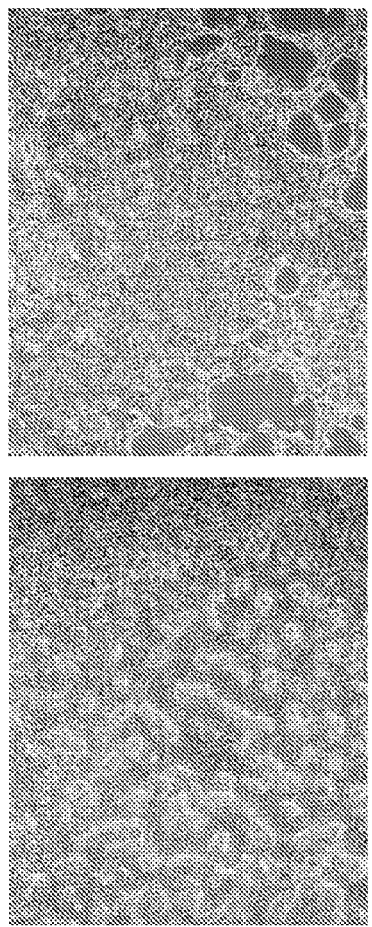
FIG. 2B
FIG. 2A
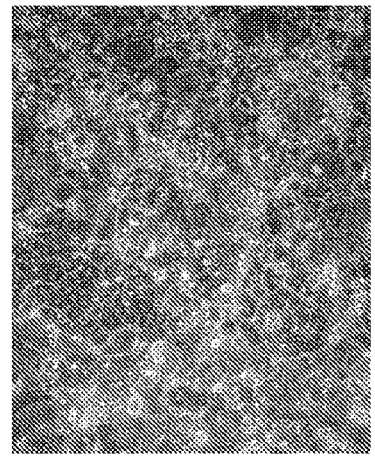
FIG. 2F
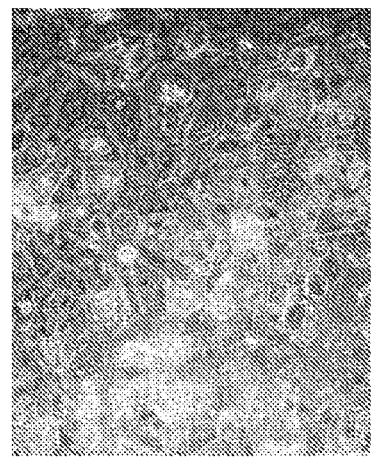
FIG. 2E
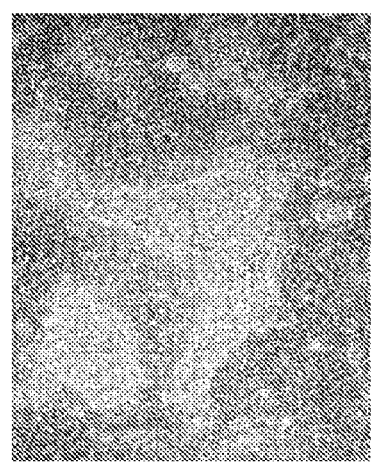
FIG. 2D Albumin

CDX2

HNF4a

ISL1

ZIC1

KRT19

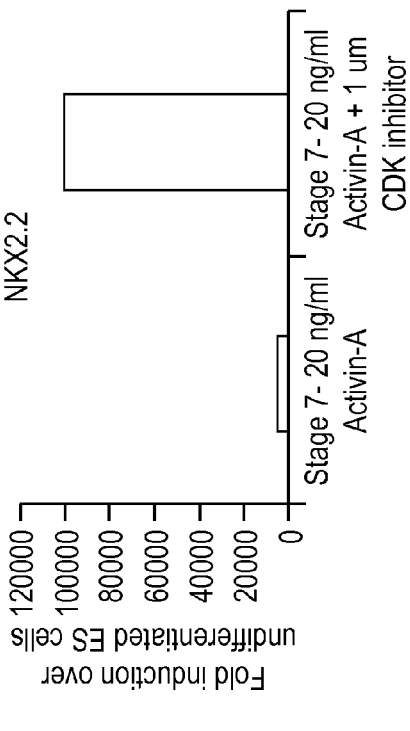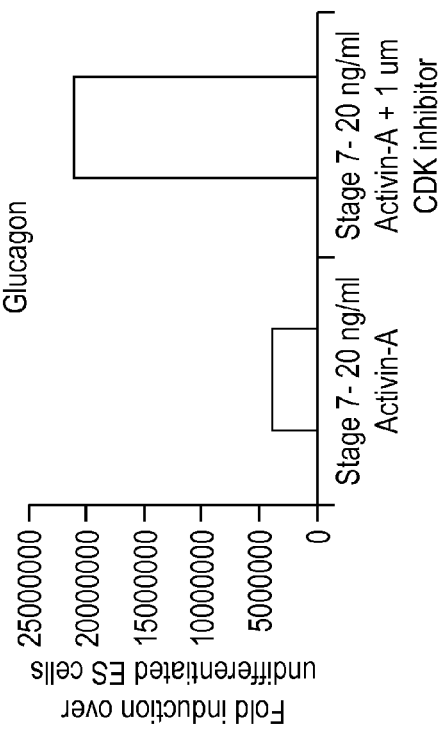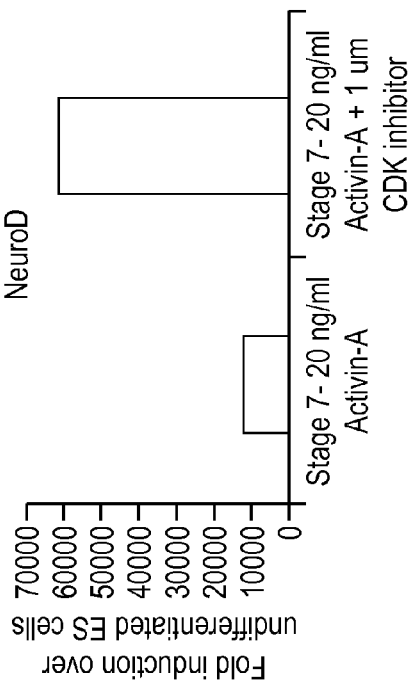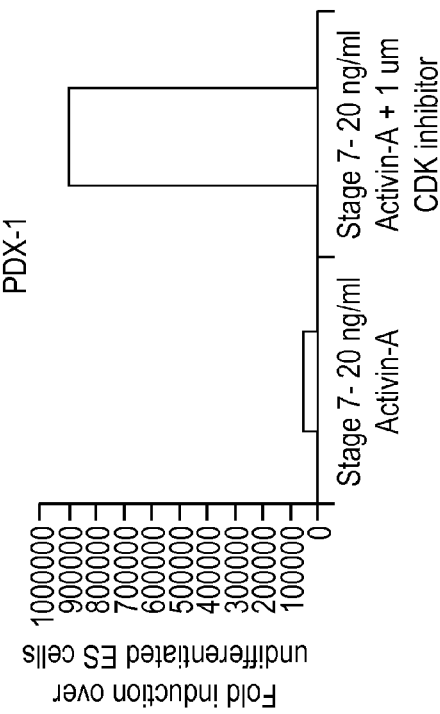

Control

+ CDK inhibitor

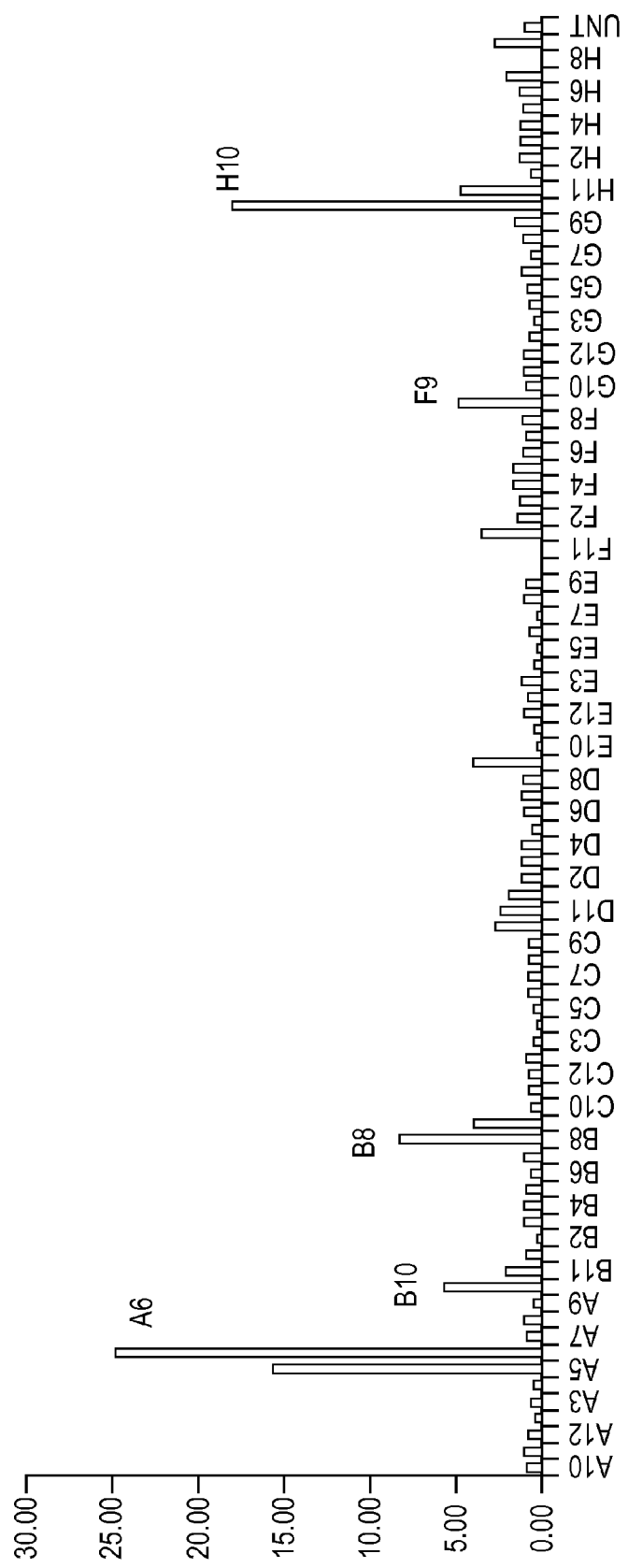

Insulin

Glucagon

Somatostatin

MAFA

DIFFERENTIATION OF HUMAN PLURIPOTENT STEM CELLS

The present invention claims priority to application Ser. No. 61/110,287, filed Oct. 31, 2008; incorporated herein by reference in its entirety.

FIELD OF THE INVENTION

The present invention provides methods to promote the differentiation of pluripotent stem cells. In particular, the present invention provides a method to increase the expression of MAFA in cells expressing markers characteristic of the pancreatic endocrine lineage.

BACKGROUND

Advances in cell-replacement therapy for Type I diabetes mellitus and a shortage of transplantable islets of Langerhans have focused interest on developing sources of insulin-producing cells, or β cells, appropriate for engraftment. One approach is the generation of functional β cells from pluripotent stem cells, such as, for example, embryonic stem cells.

In vertebrate embryonic development, a pluripotent cell gives rise to a group of cells comprising three germ layers (ectoderm, mesoderm, and endoderm) in a process known as gastrulation. Tissues such as, for example, thyroid, thymus, pancreas, gut, and liver, will develop from the endoderm, via an intermediate stage. The intermediate stage in this process is the formation of definitive endoderm. Definitive endoderm cells express a number of markers, such as, HNF-3 beta, GATA4, MIXL1 CXCR4 and SOX17.

Formation of the pancreas arises from the differentiation of definitive endoderm into pancreatic endoderm. Cells of the pancreatic endoderm express the pancreatic-duodenal homeobox gene, PDX1. In the absence of PDX1, the pancreas fails to develop beyond the formation of ventral and dorsal buds. Thus, PDX1 expression marks a critical step in pancreatic organogenesis. The mature pancreas contains, among other cell types, exocrine tissue and endocrine tissue. Exocrine and endocrine tissues arise from the differentiation of pancreatic endoderm.

Cells bearing the features of islet cells have reportedly been derived from embryonic cells of the mouse. For example, Lumelsky et al. (Science 292:1389, 2001; incorporated herein by reference in its entirety) report differentiation of mouse embryonic stem cells to insulin-secreting structures similar to pancreatic islets. Soria et al. (Diabetes 49:157, 2000; incorporated herein by reference in its entirety) report that insulin-secreting cells derived from mouse embryonic stem cells normalize glycemia in streptozotocin-induced diabetic mice.

In one example, Hori et al. (PNAS 99: 16105, 2002; incorporated herein by reference in its entirety) disclose that treatment of mouse embryonic stem cells with inhibitors of phosphoinositide 3-kinase (LY294002) produced cells that resembled β cells.

In another example, Blyszczuk et al. (PNAS 100:998, 2003; incorporated herein by reference in its entirety) reports the generation of insulin-producing cells from mouse embryonic stem cells constitutively expressing Pax4.

Micallef et al. reports that retinoic acid can regulate the commitment of embryonic stem cells to form Pdx1 positive pancreatic endoderm. Retinoic acid is most effective at inducing Pdx1 expression when added to cultures at day 4 of embryonic stem cell differentiation during a period corresponding to the end of gastrulation in the embryo (Diabetes 54:301, 2005; incorporated herein by reference in its entirety).

Miyazaki et al. reports a mouse embryonic stem cell line over-expressing Pdx1. Their results show that exogenous Pdx1 expression clearly enhanced the expression of insulin, somatostatin, glucokinase, neurogenin3, P48, Pax6, and HNF6 genes in the resulting differentiated cells (Diabetes 53: 1030, 2004; incorporated herein by reference in its entirety).

Skoudy et al. reports that activin A (a member of the TGF-β superfamily) upregulates the expression of exocrine pancreatic genes (p48 and amylase) and endocrine genes (Pdx1, insulin, and glucagon) in mouse embryonic stem cells. The maximal effect was observed using 1 nM activin A. They also observed that the expression level of insulin and Pdx1 mRNA was not affected by retinoic acid; however, 3 nM FGF7 treatment resulted in an increased level of the transcript for Pdx1 (Biochem. J. 379: 749, 2004; incorporated herein by reference in its entirety).

Shiraki et al. studied the effects of growth factors that specifically enhance differentiation of embryonic stem cells into Pdx1 positive cells. They observed that TGF-β2 reproducibly yielded a higher proportion of Pdx1 positive cells (Genes Cells. 2005 June; 10(6): 503-16; incorporated herein by reference in its entirety).

Gordon et al. demonstrated the induction of brachyury+/HNF-3beta+ endoderm cells from mouse embryonic stem cells in the absence of serum and in the presence of activin along with an inhibitor of Wnt signaling (US 2006/0003446A1; incorporated herein by reference in its entirety).

Gordon et al. (PNAS, Vol 103, page 16806, 2006; incorporated herein by reference in its entirety) states "Wnt and TGF-beta/nodal/activin signaling simultaneously were required for the generation of the anterior primitive streak".

However, the mouse model of embryonic stem cell development may not exactly mimic the developmental program in higher mammals, such as, for example, humans.

Thomson et al. isolated embryonic stem cells from human blastocysts (Science 282:114, 1998; incorporated herein by reference in its entirety). Concurrently, Gearhart and coworkers derived human embryonic germ (hEG) cell lines from fetal gonadal tissue (Shamblott et al., Proc. Natl. Acad. Sci. USA 95:13726, 1998; incorporated herein by reference in its entirety). Unlike mouse embryonic stem cells, which can be prevented from differentiating simply by culturing with Leukemia Inhibitory Factor (LIF), human embryonic stem cells must be maintained under very special conditions (U.S. Pat. No. 6,200,806; WO 99/20741; WO 01/51616; incorporated herein by reference in their entirety).

D'Amour et al., describes the production of enriched cultures of human embryonic stem cell-derived definitive endoderm in the presence of a high concentration of activin and low serum (Nature Biotechnology 2005; incorporated herein by reference in its entirety). Transplanting these cells under the kidney capsule of mice resulted in differentiation into more mature cells with characteristics of some endodermal organs. Human embryonic stem cell-derived definitive endoderm cells can be further differentiated into Pdx1 positive cells after addition of FGF-10 (US 2005/0266554A1; incorporated herein by reference in its entirety).

D'Amour et al. (Nature Biotechnology—24, 1392-1401 (2006); incorporated herein by reference in its entirety) states: "We have developed a differentiation process that converts human embryonic stem (hES) cells to endocrine cells capable of synthesizing the pancreatic hormones insulin, glucagon, somatostatin, pancreatic polypeptide and ghrelin. This process mimics in vivo pancreatic organogenesis by directing cells through stages resembling definitive endoderm, gut-tube endoderm, pancreatic endoderm and endocrine precursor en route to cells that express endocrine hormones".

In another example, Fisk et al. reports a system for producing pancreatic islet cells from human embryonic stem cells (US2006/0040387A1; incorporated herein by reference in its entirety). In this case, the differentiation pathway was divided into three stages. Human embryonic stem cells were first differentiated to endoderm using a combination of sodium butyrate and activin A. The cells were then cultured with TGF-β antagonists such as Noggin in combination with EGF or betacellulin to generate Pdx1 positive cells. The terminal differentiation was induced by nicotinamide.

In one example, Benvenistry et al. states: "We conclude that over-expression of Pdx1 enhanced expression of pancreatic enriched genes, induction of insulin expression may require additional signals that are only present in vivo" (Benvenistry et al, Stem Cells 2006; 24:1923-1930; incorporated herein by reference in its entirety).

Cyclins have been implicated in beta cell function. For example, Lilja et al report that Cdk5 is present in the insulin-secreting pancreatic β-cell (J. Biol. Chem., Vol. 276, Issue 36, 34199-34205, Sep. 7, 2001; incorporated herein by reference in its entirety). Lilja et al states "Cdk5 is present in β-cells and acts as a positive regulator of insulin exocytosis."

In another example, Marzo et al states "Cdk4 knockin mice have significantly increased beta cell mass and are physiologically functional, indicating that Cdk4 is a potential target for pancreatic beta cell mass regeneration in Type 1 diabetes" (Diabetalogia, Vol. 47, Number 4, 686-694, Apr. 1, 2004; incorporated herein by reference in its entirety).

In another example, Ubeda et al report that inhibition of cyclin-dependant kinase 5 activity protects pancreatic beta cells from glucotoxicity (J. Biol. Chem., Vol. 281, Issue 39, 28858-28864, Sep. 29, 2006; incorporated herein by reference in its entirety).

In another example, Wei et al report Cdk5-dependent regulation of glucose-stimulated insulin secretion (Nature Medicine 11, 1104-1108 (1 Oct. 2005); incorporated herein by reference in its entirety).

In another example, Vanderford et al state "MafA is a basic leucine zipper transcription factor expressed within the beta cells of the pancreas and is required to maintain normal glucose homeostasis as it is involved in various aspects of beta cell biology. MafA protein levels are known to increase in response to high glucose through mechanisms that have yet to be fully characterized. We investigated whether discrete intracellular signaling events control mafA expression. We found that the general kinase inhibitor staurosporine induces mafA expression without altering the stability of the protein. Inhibition of the MAP-kinase JNK mimics the effects of staurosporine on the expression of mafA. Calmodulin kinase and calcium signaling are also important in stimulating mafA expression by high glucose. However, staurosporine, JNK, and calmodulin kinase have different effects on the induction of insulin expression. These data reveal that MafA levels are tightly controlled by the coordinated action of multiple kinase pathways." (Archives of Biochemistry and Biophysics (2008), doi: 10.1016/j.abb.2008.10.001; incorporated herein by reference in its entirety).

Therefore, there still remains a significant need to develop methods for differentiating pluripotent stem cells into pancreatic endocrine cells, pancreatic hormone expressing cells, or pancreatic hormone secreting cells. The present invention provides methods to increase the expression of MAFA in cells expressing markers characteristic of the pancreatic endocrine lineage.

SUMMARY

In one embodiment, the present invention provides a method for increasing the expression of MAFA in cells expressing markers characteristic of the pancreatic endocrine lineage comprising the steps of culturing the cells expressing markers characteristic of the pancreatic endocrine lineage in medium comprising a sufficient amount of a cyclin-dependant kinase inhibitor to cause an increase in expression of MAFA.

BRIEF DESCRIPTION OF THE DRAWINGS

FIG. 2A) shows a 4× micrograph of cells treated according to the methods described in Example 1, at day 4 of the stage 6 treatment. B) shows a 4× micrograph of cells treated with 0.5 µM of the compound PubChemID#5330812 at day 4 of treatment. C) shows a 4× micrograph of cells treated with 1 µM of the compound PubChemID#5330812 at day 4 of treatment. D) shows a 20× micrograph of cells treated according to the methods described in Example 1, at day 6 of the stage 6 treatment. E) shows a 20× micrograph of cells treated with 0.5 µM of the compound PubChemID#5330812 at day 6 of treatment. F) shows a 20× micrograph of cells treated with 1 µM of the compound PubChemID#5330812 at day 6 of treatment.

FIG. 9 shows the effect of compounds from the EMD Calbiochem kinase inhibitor library I on the expression of MAFA in cells expressing markers characteristic of the pancreatic endocrine lineage, as determined by real-time PCR.

DETAILED DESCRIPTION

Figure 1A:
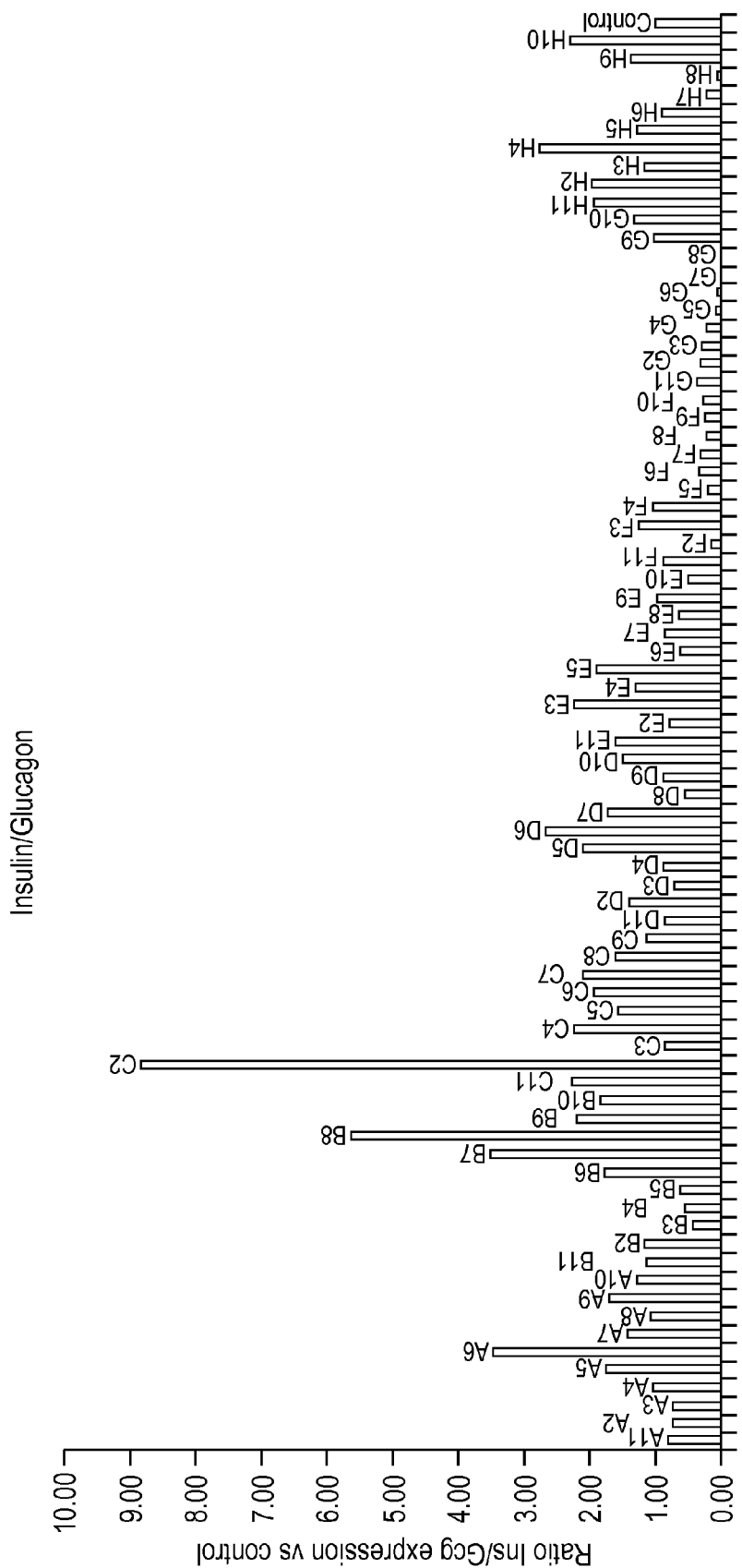
FIG. 1, panel a shows the effect of compounds from the EMD Calbiochem kinase inhibitor library on the ratio of insulin to glucagon expression in cells expressing markers characteristic of the pancreatic endocrine lineage, as determined by real-time PCR. The alphanumeric label corresponds to the compound identity as shown in Table 1. Panel b shows the effect of compounds from the EMD Calbiochem kinase inhibitor library on the ratio of MAFA to ARX4 expression in cells expressing markers characteristic of the pancreatic endocrine lineage, as determined by real-time PCR. The alphanumeric label corresponds to the compound identity as shown in Table 1.

For clarity of disclosure, and not by way of limitation, the detailed description of the invention is divided into the following subsections that describe or illustrate certain features, embodiments or applications of the present invention.

DEFINITIONS

Stem cells are undifferentiated cells defined by their ability at the single cell level to both self-renew and differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Stem cells are classified by their developmental potential as: (1) totipotent, meaning able to give rise to all embryonic and extra embryonic cell types; (2) pluripotent, meaning able to give rise to all embryonic cell types; (3) multipotent, meaning able to give rise to a subset of cell lineages but all within a particular tissue, organ, or physiological system (for example, hematopoietic stem cells (HSC) can produce progeny that include HSC (self-renewal), blood cell restricted oligopotent progenitors, and all cell types and elements (e.g., platelets) that are normal components of the blood); (4) oligopotent, meaning able to give rise to a more restricted subset of cell lineages than multipotent stem cells; and (5) unipotent, meaning able to give rise to a single cell lineage (e.g., spermatogenic stem cells).

Differentiation is the process by which an unspecialized ("uncommitted") or less specialized cell acquires the features of a specialized cell such as, for example, a nerve cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

"β-cell lineage" refers to cells with positive gene expression for the transcription factor PDX-1 and at least one of the following transcription factors: NGN3, NKX2.2. NKX6.1, NEUROD, ISL1, HNF3 beta, MAFA, PAX4, or PAX6. Cells expressing markers characteristic of the β cell lineage include β cells.

"Cells expressing markers characteristic of the definitive endoderm lineage", as used herein, refers to cells expressing at least one of the following markers: SOX17, GATA4, HNF3 beta, GSC, CER1, Nodal, FGF8, Brachyury, Mix-like homeobox protein, FGF4 CD48, eomesodermin (EOMES), DKK4, FGF17, GATA6, CXCR4, C-Kit, CD99, or OTX2. Cells expressing markers characteristic of the definitive endoderm lineage include primitive streak precursor cells, primitive streak cells, mesendoderm cells and definitive endoderm cells.

"Cells expressing markers characteristic of the pancreatic endoderm lineage", as used herein, refers to cells expressing at least one of the following markers: PDX1, HNF1 beta, PTF1 alpha, HNF-, or HB9. Cells expressing markers characteristic of the pancreatic endoderm lineage include pancreatic endoderm cells, primitive gut tube cells, and posterior foregut cells.

"Cells expressing markers characteristic of the pancreatic endocrine lineage", as used herein, refers to cells expressing at least one of the following markers: NGN3, NEUROD, ISL1, PDX1, NKX6.1, PAX4, NGN3, or PTF1 alpha. Cells expressing markers characteristic of the pancreatic endocrine lineage include pancreatic endocrine cells, pancreatic hormone expressing cells, and pancreatic hormone secreting cells, and cells of the n-cell lineage.

"Definitive endoderm", as used herein, refers to cells which bear the characteristics of cells arising from the epiblast during gastrulation and which form the gastrointestinal tract and its derivatives. Definitive endoderm cells express the following markers: HNF3 beta, GATA4, SOX17, Cerberus, OTX2, goosecoid, C-Kit, CD99, or MIXL1.

"Extraembryonic endoderm", as used herein, refers to a population of cells expressing at least one of the following markers: SOX7, AFP, or SPARC.

"Markers", as used herein, are nucleic acid or polypeptide molecules that are differentially expressed in a cell of interest. In this context, differential expression means an increased level for a positive marker and a decreased level for a negative marker. The detectable level of the marker nucleic acid or polypeptide is sufficiently higher or lower in the cells of interest compared to other cells, such that the cell of interest can be identified and distinguished from other cells using any of a variety of methods known in the art.

"Mesendoderm cell", as used herein, refers to a cell expressing at least one of the following markers: CD48, eomesodermin (EOMES), SOX17, DKK4, HNF3 beta, GSC, FGF17, or GATA6.

"Pancreatic endocrine cell", or "pancreatic hormone expressing cell", as used herein, refers to a cell capable of expressing at least one of the following hormones: insulin, glucagon, somatostatin, or pancreatic polypeptide.

"Pancreatic endoderm cell", as used herein, refers to a cell capable of expressing at least one of the following markers: NGN3, NEUROD, ISL1. PDX1. PAX4, or NKX2.2.

"Pancreatic hormone producing cell", as used herein, refers to a cell capable of producing at least one of the following hormones: insulin, glucagon, somatostatin, or pancreatic polypeptide.

"Pancreatic hormone secreting cell" as used herein, refers to a cell capable of secreting at least one of the following hormones: insulin, glucagon, somatostatin, and pancreatic polypeptide.

"Posterior foregut cell", as used herein, refers to a cell capable of secreting at least one of the following markers: PDX1, HNF1, PTF1 alpha, HNF6, HB9, or PROX1.

"Pre-primitive streak cell", as used herein, refers to a cell expressing at least one of the following markers: Nodal, or FGF8.

"Primitive gut tube cell", as used herein, refers to a cell capable of secreting at least one of the following markers: HNF1, or HNF4A.

"Primitive streak cell", as used herein, refers to a cell expressing at least one of the following markers: Brachyury, Mix-like homeobox protein, or FGF4.

Isolation, Expansion and Culture of Pluripotent Stem Cells

Characterization of Pluripotent Stem Cells

Pluripotent stem cells may express one or more of the stage-specific embryonic antigens (SSEA) 3 and 4, and markers detectable using antibodies designated Tra-1-60 and Tra-1-81 (Thomson et al., Science 282:1145, 1998; incorporated herein by reference in its entirety). Differentiation of pluripotent stem cells in vitro results in the loss of SSEA-4, Tra-1-60, and Tra-1-81 expression (if present) and increased expression of SSEA-1. Undifferentiated pluripotent stem cells typically have alkaline phosphatase activity, which can be detected by fixing the cells with 4% paraformaldehyde, and then developing with Vector Red as a substrate, as described by the manufacturer (Vector Laboratories, Burlingame Calif.) Undifferentiated pluripotent stem cells also typically express Oct-4 and TERT, as detected by RT-PCR.

Another desirable phenotype of propagated pluripotent stem cells is a potential to differentiate into cells of all three germinal layers: endoderm, mesoderm, and ectoderm tissues. Pluripotency of pluripotent stem cells can be confirmed, for example, by injecting cells into severe combined immunodeficient (SCID) mice, fixing the teratomas that form using 4% paraformaldehyde, and then examining them histologically for evidence of cell types from the three germ layers. Alternatively, pluripotency may be determined by the creation of embryoid bodies and assessing the embryoid bodies for the presence of markers associated with the three germinal layers.

Propagated pluripotent stem cell lines may be karyotyped using a standard G-banding technique and compared to published karyotypes of the corresponding primate species. It is desirable to obtain cells that have a "normal karyotype," which means that the cells are euploid, wherein all human chromosomes are present and not noticeably altered.

Sources of Pluripotent Stem Cells

The types of pluripotent stem cells that may be used include established lines of pluripotent cells derived from tissue formed after gestation, including pre-embryonic tissue (such as, for example, a blastocyst), embryonic tissue, or fetal tissue taken any time during gestation, typically but not necessarily before approximately 10-12 weeks gestation. Non-limiting examples are established lines of human embryonic stem cells or human embryonic germ cells, such as, for example the human embryonic stem cell lines H1, H7, and H9 (WiCell). Also contemplated is use of the compositions of this disclosure during the initial establishment or stabilization of such cells, in which case the source cells would be primary pluripotent cells taken directly from the source tissues. Also suitable are cells taken from a pluripotent stem cell population already cultured in the absence of feeder cells. Also suitable are mutant human embryonic stem cell lines, such as, for example, BG01v (BresaGen, Athens, Ga.).

In one embodiment, human embryonic stem cells are prepared as described by Thomson et al. (U.S. Pat. No. 5,843,780; Science 282:1145, 1998; Curr. Top. Dev. Biol. 38:133 ff., 1998; Proc. Natl. Acad. Sci. U.S.A. 92:7844, 1995; incorporated herein by reference in their entirety).

Culture of Pluripotent Stem Cells

In one embodiment, pluripotent stem cells are typically cultured on a layer of feeder cells that support the pluripotent stem cells in various ways. Alternatively, pluripotent stem cells are cultured in a culture system that is essentially free of feeder cells, but nonetheless supports proliferation of pluripotent stem cells without undergoing substantial differentiation. The growth of pluripotent stem cells in feeder-free culture without differentiation is supported using a medium conditioned by culturing previously with another cell type. Alternatively, the growth of pluripotent stem cells in feeder-free culture without differentiation is supported using a chemically defined medium.

For example, Reubinoff et al (Nature Biotechnology 18: 399-404 (2000); incorporated herein by reference in its entirety) and Thompson et al (Science 6 Nov. 1998: Vol. 282. no. 5391, pp. 1145-1147; incorporated herein by reference in its entirety) disclose the culture of pluripotent stem cell lines from human blastocysts using a mouse embryonic fibroblast feeder cell layer.

Richards et al, (Stem Cells 21: 546-556, 2003; incorporated herein by reference in its entirety) evaluated a panel of 11 different human adult, fetal and neonatal feeder cell layers for their ability to support human pluripotent stem cell culture. Richards et al, states: "human embryonic stem cell lines cultured on adult skin fibroblast feeders retain human embryonic stem cell morphology and remain pluripotent".

US20020072117, incorporated herein by reference in its entirety, discloses cell lines that produce media that support the growth of primate pluripotent stem cells in feeder-free culture. The cell lines employed are mesenchymal and fibroblast-like cell lines obtained from embryonic tissue or differentiated from embryonic stem cells. US20020072117 also discloses the use of the cell lines as a primary feeder cell layer.

In another example, Wang et al (Stem Cells 23: 1221-1227, 2005; incorporated herein by reference in its entirety) discloses methods for the long-term growth of human pluripotent stem cells on feeder cell layers derived from human embryonic stem cells.

In another example, Stojkovic et al (Stem Cells 2005 23: 306-314, 2005; incorporated herein by reference in its entirety) disclose a feeder cell system derived from the spontaneous differentiation of human embryonic stem cells.

In a further example, Miyamoto et al (Stem Cells 22: 433-440, 2004; incorporated herein by reference in its entirety) disclose a source of feeder cells obtained from human placenta.

Amit et al (Biol. Reprod 68: 2150-2156, 2003; incorporated herein by reference in its entirety) discloses a feeder cell layer derived from human foreskin.

In another example, Inzunza et al (Stem Cells 23: 544-549, 2005; incorporated herein by reference in its entirety) disclose a feeder cell layer from human postnatal foreskin fibroblasts.

U.S. Pat. No. 6,642,048, incorporated herein by reference in its entirety, discloses media that support the growth of primate pluripotent stem (pPS) cells in feeder-free culture, and cell lines useful for production of such media. U.S. Pat. No. 6,642,048 states: "This invention includes mesenchymal and fibroblast-like cell lines obtained from embryonic tissue or differentiated from embryonic stem cells. Methods for deriving such cell lines, processing media, and growing stem cells using the conditioned media are described and illustrated in this disclosure."

In another example, WO2005014799, incorporated herein by reference in its entirety, discloses conditioned medium for the maintenance, proliferation and differentiation of mammalian cells. WO2005014799 states: "The culture medium produced in accordance with the present invention is conditioned by the cell secretion activity of murine cells, in particular, those differentiated and immortalized transgenic hepatocytes, named MMH (Met Murine Hepatocyte)."

In another example, Xu et al (Stem Cells 22: 972-980, 2004; incorporated herein by reference in its entirety) discloses conditioned medium obtained from human embryonic stem cell derivatives that have been genetically modified to over express human telomerase reverse transcriptase.

In another example, US200700.10011, incorporated herein by reference in its entirety, discloses a chemically defined culture medium for the maintenance of pluripotent stem cells.

An alternative culture system employs serum-free medium supplemented with growth factors capable of promoting the proliferation of embryonic stem cells. For example, Cheon et al (BioReprod DOI:10.1095/biolreprod.105.046870, Oct. 19, 2005; incorporated herein by reference in its entirety) disclose a feeder-free, serum-free culture system in which embryonic stem cells are maintained in unconditioned serum replacement (SR) medium supplemented with different growth factors capable of triggering embryonic stem cell self-renewal.

In another example, Levenstein et al (Stem Cells 24: 568-574, 2006; incorporated herein by reference in its entirety) disclose methods for the long-term culture of human embryonic stem cells in the absence of fibroblasts or conditioned medium, using media supplemented with bFGF.

In another example, US20050148070, incorporated herein by reference in its entirety, discloses a method of culturing human embryonic stem cells in defined media without serum and without fibroblast feeder cells, the method comprising: culturing the stem cells in a culture medium containing albumin, amino acids, vitamins, minerals, at least one transferrin or transferrin substitute, at least one insulin or insulin substitute, the culture medium essentially free of mammalian fetal serum and containing at least about 100 ng/ml of a fibroblast growth factor capable of activating a fibroblast growth factor signaling receptor, wherein the growth factor is supplied from a source other than just a fibroblast feeder layer, the medium supported the proliferation of stem cells in an undifferentiated state without feeder cells or conditioned medium.

In another example, US20050233446, incorporated herein by reference in its entirety, discloses a defined media useful in culturing stem cells, including undifferentiated primate primordial stem cells. In solution, the media is substantially isotonic as compared to the stem cells being cultured. In a given culture, the particular medium comprises a base medium and an amount of each of bFGF, insulin, and ascorbic acid necessary to support substantially undifferentiated growth of the primordial stem cells.

In another example, U.S. Pat. No. 6,800,480, incorporated herein by reference in its entirety, states "In one embodiment, a cell culture medium for growing primate-derived primordial stem cells in a substantially undifferentiated state is provided which includes a low osmotic pressure, low endotoxin basic medium that is effective to support the growth of primate-derived primordial stem cells. The basic medium is combined with a nutrient serum effective to support the growth of primate-derived primordial stem cells and a substrate selected from the group consisting of feeder cells and an extracellular matrix component derived from feeder cells. The medium further includes non-essential amino acids, an anti-oxidant, and a first growth factor selected from the group consisting of nucleosides and a pyruvate salt."

In another example, US20050244962, incorporated herein by reference in its entirety, states: "In one aspect the invention provides a method of culturing primate embryonic stem cells. One cultures the stem cells in a culture essentially free of mammalian fetal serum (preferably also essentially free of any animal serum) and in the presence of fibroblast growth factor that is supplied from a source other than just a fibroblast feeder layer. In a preferred form, the fibroblast feeder layer, previously required to sustain a stem cell culture, is rendered unnecessary by the addition of sufficient fibroblast growth factor."

In a further example, WO2005065354, incorporated herein by reference in its entirety, discloses a defined, isotonic culture medium that is essentially feeder-free and serum-free, comprising: a. a basal medium; b. an amount of bFGF sufficient to support growth of substantially undifferentiated mammalian stem cells; c. an amount of insulin sufficient to support growth of substantially undifferentiated mammalian stem cells; and d. an amount of ascorbic acid sufficient to support growth of substantially undifferentiated mammalian stem cells.

In another example, WO2005086845, incorporated herein by reference in its entirety, discloses a method for maintenance of an undifferentiated stem cell, said method comprising exposing a stem cell to a member of the transforming growth factor-beta (TGF-β) family of proteins, a member of the fibroblast growth factor (FGF) family of proteins, or nicotinamide (NIC) in an amount sufficient to maintain the cell in an undifferentiated state for a sufficient amount of time to achieve a desired result.

The pluripotent stem cells may be plated onto a suitable culture substrate. In one embodiment, the suitable culture substrate is an extracellular matrix component, such as, for example, those derived from basement membrane or that may form part of adhesion molecule receptor-ligand couplings. In one embodiment, a the suitable culture substrate is MATRIGEL® (Becton Dickenson). MATRIGEL® is a soluble preparation from Engelbreth-Holm Swarm tumor cells that gels at room temperature to form a reconstituted basement membrane.

Other extracellular matrix components and component mixtures are suitable as an alternative. Depending on the cell type being proliferated, this may include laminin, fibronectin, proteoglycan, entactin, heparan sulfate, and the like, alone or in various combinations.

The pluripotent stem cells may be plated onto the substrate in a suitable distribution and in the presence of a medium that promotes cell survival, propagation, and retention of the desirable characteristics. All these characteristics benefit from careful attention to the seeding distribution and can readily be determined by one of skill in the art.

Suitable culture media may be made from the following components, such as, for example, Dulbecco's modified Eagle's medium (DMEM), Gibco #11965-092; Knockout Dulbecco's modified Eagle's medium (KO DMEM), Gibco #10829-018; Ham's F12/50% DMEM basal medium; 200 mM L-glutamine, Gibco #15039-027; non-essential amino acid solution, Gibco 11140-050; β-mercaptoethanol, Sigma #M7522; human recombinant basic fibroblast growth factor (bFGF), Gibco #13256-029.

Formation of Pancreatic Hormone Producing Cells from Pluripotent Stem Cells

In one embodiment, the present invention provides a method for producing pancreatic hormone producing cells from pluripotent stem cells, comprising the steps of:
a. Culturing pluripotent stem cells,
b. Differentiating the pluripotent stem cells into cells expressing markers characteristic of the definitive endoderm lineage,
c. Differentiating the cells expressing markers characteristic of the definitive endoderm lineage into cells expressing markers characteristic of the pancreatic endoderm lineage, and
d. Differentiating the cells expressing markers characteristic of the pancreatic endoderm lineage into cells expressing markers characteristic of the pancreatic endocrine lineage.

Pluripotent stem cells suitable for use in the present invention include, for example, the human embryonic stem cell line H9 (NIH code: WA09), the human embryonic stem cell line H1 (NIH code: WA01), the human embryonic stem cell line 1-17 (NIH code: WA07), and the human embryonic stem cell line SA002 (Cellartis, Sweden). Also suitable for use in the present invention are cells that express at least one of the following markers characteristic of pluripotent cells: ABCG2, cripto, CD9, FOXD3, Connexin43, Connexin45, OCT4, SOX2, NANOG, hTERT, UTF1, ZFP42, SSEA3, SSEA4, Tra1-60, or Tra1-81.

Markers characteristic of the definitive endoderm lineage are selected from the group consisting of SOX17, GATA4, HNF3 beta, GSC, CER1, NODAL, FGF8, Brachyury, Mix-like homeobox protein, FGF4 CD48, eomesodermin (EOMES), DKK4, FGF17, GATA6, CXCR4, C-Kit, CD99, and OTX2. Suitable for use in the present invention is a cell that expresses at least one of the markers characteristic of the definitive endoderm lineage. In one aspect of the present invention, a cell expressing markers characteristic of the definitive endoderm lineage is a primitive streak precursor cell. In an alternate aspect, a cell expressing markers characteristic of the definitive endoderm lineage is a mesendoderm cell. In an alternate aspect, a cell expressing markers characteristic of the definitive endoderm lineage is a definitive endoderm cell.

Markers characteristic of the pancreatic endoderm lineage are selected from the group consisting of PDX1, HNF1 beta, PTF1 alpha, HNF6, HB9 and PROX1. Suitable for use in the present invention is a cell that expresses at least one of the markers characteristic of the pancreatic endoderm lineage. In one aspect of the present invention, a cell expressing markers characteristic of the pancreatic endoderm lineage is a pancreatic endoderm cell.

Markers characteristic of the pancreatic endocrine lineage are selected from the group consisting of NGN3, NEUROD, ISL1, PDX1, NKX6.1, PAX4, NGN3, and PTF1 alpha. In one embodiment, a pancreatic endocrine cell is capable of expressing at least one of the following hormones: insulin, glucagon, somatostatin, and pancreatic polypeptide. Suitable for use in the present invention is a cell that expresses at least one of the markers characteristic of the pancreatic endocrine lineage. In one aspect of the present invention, a cell expressing markers characteristic of the pancreatic endocrine lineage is a pancreatic endocrine cell. The pancreatic endocrine cell may be a pancreatic hormone expressing cell. Alternatively, the pancreatic endocrine cell may be a pancreatic hormone secreting cell.

In one aspect of the present invention, the pancreatic endocrine cell is a cell expressing markers characteristic of the β cell lineage. A cell expressing markers characteristic of the β cell lineage expresses Pdx1 and at least one of the following transcription factors: NGN3, NKX2.2, NKX6.1, NEUROD, ISL1, HNF3 beta, MAFA, PAX4, or PAX6. In one aspect of the present invention, a cell expressing markers characteristic of the β cell lineage is a β cell.

Formation of Cells Expressing Markers Characteristic of the Definitive Endoderm Lineage Pluripotent stem cells may be differentiated into cells expressing markers characteristic of the definitive endoderm lineage by any method in the art or by any method proposed in this invention.

For example, pluripotent stem cells may be differentiated into cells expressing markers characteristic of the definitive endoderm lineage according to the methods disclosed in D'Amour et al, Nature Biotechnology 23, 1534-1541 (2005); incorporated herein by reference in its entirety.

For example, pluripotent stem cells may be differentiated into cells expressing markers characteristic of the definitive endoderm lineage according to the methods disclosed in Shinozaki et al, Development 131, 1651-1662 (2004); incorporated herein by reference in its entirety.

For example, pluripotent stem cells may be differentiated into cells expressing markers characteristic of the definitive endoderm lineage according to the methods disclosed in McLean et al, Stem Cells 25, 29-38 (2007); incorporated herein by reference in its entirety.

For example, pluripotent stem cells may be differentiated into cells expressing markers characteristic of the definitive endoderm lineage according to the methods disclosed in D'Amour et al, Nature Biotechnology 24, 1392-1401 (2006); incorporated herein by reference in its entirety.

For example, pluripotent stem cells may be differentiated into cells expressing markers characteristic of the definitive endoderm lineage by culturing the pluripotent stem cells in medium containing activin A in the absence of serum, then culturing the cells with activin A and serum, and then culturing the cells with activin A and serum of a different concentration. An example of this method is disclosed in Nature Biotechnology 23, 1534-1541 (2005); incorporated herein by reference in its entirety.

For example, pluripotent stem cells may be differentiated into cells expressing markers characteristic of the definitive endoderm lineage by culturing the pluripotent stem cells in medium containing activin A in the absence of serum, then culturing the cells with activin A with serum of another concentration. An example of this method is disclosed in D' Amour et al, Nature Biotechnology, 2005; incorporated herein by reference in its entirety.

For example, pluripotent stem cells may be differentiated into cells expressing markers characteristic of the definitive endoderm lineage by culturing the pluripotent stem cells in medium containing activin A and a Wnt ligand in the absence of serum, then removing the Wnt ligand and culturing the cells with activin A with serum. An example of this method is disclosed in Nature Biotechnology 24, 1392-1401 (2006); incorporated herein by reference in its entirety.

For example, pluripotent stem cells may be differentiated into cells expressing markers characteristic of the definitive endoderm lineage by treating the pluripotent stem cells according to the methods disclosed in U.S. patent application Ser. No. 11/736,908, assigned to LifeScan, Inc., incorporated herein by reference in its entirety.

For example, pluripotent stem cells may be differentiated into cells expressing markers characteristic of the definitive endoderm lineage by treating the pluripotent stem cells according to the methods disclosed in U.S. patent application Ser. No. 11/779,311, assigned to LifeScan, Inc., incorporated herein by reference in its entirety.

For example, pluripotent stem cells may be differentiated into cells expressing markers characteristic of the definitive endoderm lineage by treating the pluripotent stem cells according to the methods disclosed in U.S. patent application Ser. No. 60/990,529; incorporated herein by reference in its entirety.

For example, pluripotent stem cells may be differentiated into cells expressing markers characteristic of the definitive endoderm lineage by treating the pluripotent stem cells according to the methods disclosed in U.S. patent application Ser. No. 61/076,889, incorporated herein by reference in its entirety.

For example, pluripotent stem cells may be differentiated into cells expressing markers characteristic of the definitive endoderm lineage by treating the pluripotent stem cells according to the methods disclosed in U.S. patent application Ser. No. 61/076,900, incorporated herein by reference in its entirety.

For example, pluripotent stem cells may be differentiated into cells expressing markers characteristic of the definitive endoderm lineage by treating the pluripotent stem cells according to the methods disclosed in U.S. patent application Ser. No. 61/076,908, incorporated herein by reference in its entirety.

For example, pluripotent stem cells may be differentiated into cells expressing markers characteristic of the definitive endoderm lineage by treating the pluripotent stem cells according to the methods disclosed in U.S. patent application Ser. No. 61/076,915, incorporated herein by reference in its entirety.

Differentiation of Cells Expressing Markers Characteristic of the Definitive Endoderm Lineage Formation of cells expressing markers characteristic of the definitive endoderm lineage may be determined by testing for the presence of the markers before and after following a particular protocol. Pluripotent stem cells typically do not express such markers. Thus, differentiation of pluripotent cells is detected when cells begin to express them.

The efficiency of differentiation may be determined by exposing a treated cell population to an agent (such as an antibody) that specifically recognizes a protein marker expressed by cells expressing markers characteristic of the definitive endoderm lineage.

Methods for assessing expression of protein and nucleic acid markers in cultured or isolated cells are standard in the art. These include quantitative reverse transcriptase polymerase chain reaction (RT-PCR), Northern blots, in situ hybridization (see, e.g., Current Protocols in Molecular Biology (Ausubel et al., eds. 2001 supplement); incorporated herein by reference in its entirety) and immunoassays such as immunohistochemical analysis of sectioned material, Western blotting, and for markers that are accessible in intact cells, flow cytometry analysis (FACS) (see, e.g., Harlow and Lane, Using Antibodies: A Laboratory Manual, New York: Cold Spring Harbor Laboratory Press (1998); incorporated herein by reference in its entirety).

Characteristics of pluripotent stem cells are well known to those skilled in the art, and additional characteristics of pluripotent stem cells continue to be identified. Pluripotent stem cell markers include, for example, the expression of one or more of the following: ABCG2, cripto, FOXD3, Connexin43, Connexin45, OCT4, SOX2, NANOG, hTERT, UTF1, ZFP42, SSEA3, SSEA4, Tra1-60, or Tra1-81.

After treating pluripotent stem cells with the methods of the present invention, the differentiated cells may be purified by exposing a treated cell population to an agent (such as an antibody) that specifically recognizes a protein marker, such as CXCR4, expressed by cells expressing markers characteristic of the definitive endoderm lineage.

Formation of Cells Expressing Markers Characteristic of the Pancreatic Endoderm Lineage Cells expressing markers characteristic of the definitive endoderm lineage may be differentiated into cells expressing markers characteristic of the pancreatic endoderm lineage by any method in the art or by any method proposed in this invention.

For example, cells expressing markers characteristic of the definitive endoderm lineage may be differentiated into cells expressing markers characteristic of the pancreatic endoderm lineage according to the methods disclosed in D'Amour et al, Nature Biotechnology 24, 1392-1401 (2006); incorporated herein by reference in its entirety.

For example, cells expressing markers characteristic of the definitive endoderm lineage are further differentiated into cells expressing markers characteristic of the pancreatic endoderm lineage, by treating the cells expressing markers characteristic of the definitive endoderm lineage with a fibroblast growth factor and the hedgehog signaling pathway inhibitor KAAD-cyclopamine, then removing the medium containing the fibroblast growth factor and KAAD-cyclopamine and subsequently culturing the cells in medium containing retinoic acid, a fibroblast growth factor and KAAD-cyclopamine. An example of this method is disclosed in Nature Biotechnology 24, 1392-1401 (2006); incorporated herein by reference in its entirety.

In one aspect of the present invention, cells expressing markers characteristic of the definitive endoderm lineage are further differentiated into cells expressing markers characteristic of the pancreatic endoderm lineage, by treating the cells expressing markers characteristic of the definitive endoderm lineage with retinoic acid and at least one fibroblast growth factor for a period of time, according to the methods disclosed in U.S. patent application Ser. No. 11/736,908, assigned to LifeScan, Inc., incorporated herein by reference in its entirety.

In one aspect of the present invention, cells expressing markers characteristic of the definitive endoderm lineage are further differentiated into cells expressing markers characteristic of the pancreatic endoderm lineage, by treating the cells expressing markers characteristic of the definitive endoderm lineage with retinoic acid and at least one fibroblast growth factor for a period of time, according to the methods disclosed in U.S. patent application Ser. No. 11/779,311, assigned to LifeScan, Inc., incorporated herein by reference in its entirety.

In one aspect of the present invention, cells expressing markers characteristic of the definitive endoderm lineage are further differentiated into cells expressing markers characteristic of the pancreatic endoderm lineage, by treating the cells expressing markers characteristic of the definitive endoderm lineage according to the methods disclosed in U.S. patent application Ser. No. 60/990,529, incorporated herein by reference in its entirety.

Detection of Cells Expressing Markers Characteristic of the Pancreatic Endoderm Lineage Markers characteristic of the pancreatic endoderm lineage are well known to those skilled in the art, and additional markers characteristic of the pancreatic endoderm lineage continue to be identified. These markers can be used to confirm that the cells treated in accordance with the present invention have differentiated to acquire the properties characteristic of the pancreatic endoderm lineage. Pancreatic endoderm lineage specific markers include the expression of one or more transcription factors such as, for example, HLXB9, PTF1 alpha, PDX1, NNF6, or HNF1 beta.

The efficiency of differentiation may be determined by exposing a treated cell population to an agent (such as an antibody) that specifically recognizes a protein marker expressed by cells expressing markers characteristic of the pancreatic endoderm lineage.

Methods for assessing expression of protein and nucleic acid markers in cultured or isolated cells are standard in the art. These include quantitative reverse transcriptase polymerase chain reaction (RT-PCR), Northern blots, in situ hybridization (see, e.g., Current Protocols in Molecular Biology (Ausubel et al., eds. 2001 supplement)), incorporated herein by reference in its entirety, and immunoassays such as immunohistochemical analysis of sectioned material, Western blotting, and for markers that are accessible in intact cells, flow cytometry analysis (FACS) (see, e.g., Harlow and Lane, Using Antibodies: A Laboratory Manual. New York: Cold Spring Harbor Laboratory Press (1998); incorporated herein by reference in its entirety).

Formation of Cells Expressing Markers Characteristic of the Pancreatic Endocrine Lineage Cells expressing markers characteristic of the pancreatic endoderm lineage may be differentiated into cells expressing markers characteristic of the pancreatic endocrine lineage by any method in the art or by any method disclosed in this invention.

For example, cells expressing markers characteristic of the pancreatic endoderm lineage may be differentiated into cells expressing markers characteristic of the pancreatic endocrine lineage according to the methods disclosed in D'Amour et al, Nature Biotechnology 24, 1392-1401 (2006); incorporated herein by reference in its entirety.

For example, cells expressing markers characteristic of the pancreatic endoderm lineage are further differentiated into cells expressing markers characteristic of the pancreatic endocrine lineage, by culturing the cells expressing markers characteristic of the pancreatic endoderm lineage in medium containing DAPT and exendin 4, then removing the medium containing DAPT and exendin 4 and subsequently culturing the cells in medium containing exendin 1, IGF-1 and HGF. An example of this method is disclosed in Nature Biotechnology 24, 1392-1401 (2006), incorporated herein by reference in its entirety.

For example, cells expressing markers characteristic of the pancreatic endoderm lineage are further differentiated into cells expressing markers characteristic of the pancreatic endocrine lineage, by culturing the cells expressing markers characteristic of the pancreatic endoderm lineage in medium containing exendin 4, then removing the medium containing exendin 4 and subsequently culturing the cells in medium containing exendin 1, IGF-1 and HGF. An example of this method is disclosed in D'Amour et al, Nature Biotechnology, 2006, incorporated herein by reference in its entirety.

For example, cells expressing markers characteristic of the pancreatic endoderm lineage are further differentiated into cells expressing markers characteristic of the pancreatic endocrine lineage, by culturing the cells expressing markers characteristic of the pancreatic endoderm lineage in medium containing DAPT and exendin 4. An example of this method is disclosed in D'Amour et al, Nature Biotechnology, 2006, incorporated herein by reference in its entirety.

For example, cells expressing markers characteristic of the pancreatic endoderm lineage are further differentiated into cells expressing markers characteristic of the pancreatic endocrine lineage, by culturing the cells expressing markers characteristic of the pancreatic endoderm lineage in medium containing exendin 4. An example of this method is disclosed in D'Amour et al, Nature Biotechnology, 2006, incorporated herein by reference in its entirety.

In one aspect of the present invention, cells expressing markers characteristic of the pancreatic endoderm lineage are further differentiated into cells expressing markers characteristic of the pancreatic endocrine lineage, by treating the cells expressing markers characteristic of the pancreatic endoderm lineage with a factor that inhibits the Notch signaling pathway, according to the methods disclosed in U.S. patent application Ser. No. 11/736,908, assigned to LifeScan, Inc., incorporated herein by reference in its entirety.

In one aspect of the present invention, cells expressing markers characteristic of the pancreatic endoderm lineage are further differentiated into cells expressing markers characteristic of the pancreatic endocrine lineage, by treating the cells expressing markers characteristic of the pancreatic endoderm lineage with a factor that inhibits the Notch signaling pathway, according to the methods disclosed in U.S. patent application Ser. No. 11/779,311, assigned to LifeScan, Inc. incorporated herein by reference in its entirety.

In one aspect of the present invention, cells expressing markers characteristic of the pancreatic endoderm lineage are further differentiated into cells expressing markers characteristic of the pancreatic endocrine lineage, by treating the cells expressing markers characteristic of the pancreatic endoderm lineage with a factor that inhibits the Notch signaling pathway, according to the methods disclosed in U.S. patent application Ser. No. 60/953,178, assigned to LifeScan, Inc., incorporated herein by reference in its entirety.

In one aspect of the present invention, cells expressing markers characteristic of the pancreatic endoderm lineage are further differentiated into cells expressing markers characteristic of the pancreatic endocrine lineage, by treating the cells expressing markers characteristic of the pancreatic endoderm lineage according to the methods disclosed in U.S. patent application Ser. No. 60/990,529; incorporated herein by reference in its entirety.

In one aspect of the present invention, the present invention provides a method for increasing the expression of markers associated with the pancreatic endocrine lineage comprising treating cells expressing markers characteristic of the pancreatic endocrine lineage with medium comprising a sufficient amount of a TGF-β receptor agonist to cause an increase in expression of markers associated with the pancreatic endocrine lineage according to the methods disclosed in U.S. patent application Ser. No. 61/110,278; incorporated herein by reference in its entirety.

Detection of Cells Expressing Markers Characteristic of the Pancreatic Endocrine Lineage Markers characteristic of cells of the pancreatic endocrine lineage are well known to those skilled in the art, and additional markers characteristic of the pancreatic endocrine lineage continue to be identified. These markers can be used to confirm that the cells treated in accordance with the present invention have differentiated to acquire the properties characteristic of the pancreatic endocrine lineage. Pancreatic endocrine lineage specific markers include the expression of one or more transcription factors such as, for example, NGN3, NEUROD, or ISL1.

Markers characteristic of cells of the β cell lineage are well known to those skilled in the art, and additional markers characteristic of the β cell lineage continue to be identified. These markers can be used to confirm that the cells treated in accordance with the present invention have differentiated to acquire the properties characteristic of the β-cell lineage. β cell lineage specific characteristics include the expression of one or more transcription factors such as, for example, PDX1, NKX2.2, NKX6.1, ISL1, PAX6, PAX4, NEUROD, HNF1 beta, HNF6, HNF3 beta, or MAFA, among others. These transcription factors are well established in the art for identification of endocrine cells. See, e.g., Edlund (Nature Reviews Genetics 3: 524-632 (2002); incorporated herein by reference in its entirety).

The efficiency of differentiation may be determined by exposing a treated cell population to an agent (such as an antibody) that specifically recognizes a protein marker expressed by cells expressing markers characteristic of the pancreatic endocrine lineage. Alternatively, the efficiency of differentiation may be determined by exposing a treated cell population to an agent (such as an antibody) that specifically recognizes a protein marker expressed by cells expressing markers characteristic of the β cell lineage.

Methods for assessing expression of protein and nucleic acid markers in cultured or isolated cells are standard in the art. These include quantitative reverse transcriptase polymerase chain reaction (RT-PCR), Northern blots, in situ hybridization (see, e.g., Current Protocols in Molecular Biology (Ausubel et al., eds. 2001 supplement); incorporated herein by reference in its entirety) and immunoassays such as immunohistochemical analysis of sectioned material, Western blotting, and for markers that are accessible in intact cells, flow cytometry analysis (FACS) (see, e.g., Harlow and Lane, Using Antibodies: A Laboratory Manual. New York: Cold Spring Harbor Laboratory Press (1998); incorporated herein by reference in its entirety).

In one aspect of the present invention, the efficiency of differentiation is determined by measuring the percentage of insulin positive cells in a given cell culture following treatment. In one embodiment, the methods of the present invention produce about 100% insulin positive cells in a given culture. In an alternate embodiment, the methods of the present invention produce about 90% insulin positive cells in a given culture. In an alternate embodiment, the methods of the present invention produce about 80% insulin positive cells in a given culture. In an alternate embodiment, the methods of the present invention produce about 70% insulin positive cells in a given culture. In an alternate embodiment, the methods of the present invention produce about 60% insulin positive cells in a given culture. In an alternate embodiment, the methods of the present invention produce about 50% insulin positive cells in a given culture. In an alternate embodiment, the methods of the present invention produce about 40% insulin positive cells in a given culture. In an alternate embodiment, the methods of the present invention produce about 30% insulin positive cells in a given culture. In an alternate embodiment, the methods of the present invention produce about 20% insulin positive cells in a given culture. In an alternate embodiment, the methods of the present invention produce about 10% insulin positive cells in a given culture. In an alternate embodiment, the methods of the present invention produce about 5% insulin positive cells in a given culture.

In one aspect of the present invention, the efficiency of differentiation is determined by measuring glucose-stimulated insulin secretion, as detected by measuring the amount of C-peptide released by the cells. In one embodiment, cells produced by the methods of the present invention produce about 1000 ng C-peptide/pg DNA. In an alternate embodiment, cells produced by the methods of the present invention produce about 900 ng C-peptide/pg DNA. In an alternate embodiment, cells produced by the methods of the present invention produce about 800 ng C-peptide/pg DNA. In an alternate embodiment, cells produced by the methods of the present invention produce about 700 ng C-peptide/pg DNA. In an alternate embodiment, cells produced by the methods of the present invention produce about 600 ng C-peptide/pg DNA. In an alternate embodiment, cells produced by the methods of the present invention produce about 500 ng C-peptide/pg DNA. In an alternate embodiment, cells produced by the methods of the present invention produce about 400 ng C-peptide/pg DNA. In an alternate embodiment, cells produced by the methods of the present invention produce about 500 ng C-peptide/pg DNA. In an alternate embodiment, cells produced by the methods of the present invention produce about 400 ng C-peptide/pg DNA. In an alternate embodiment, cells produced by the methods of the present invention produce about 300 ng C-peptide/pg DNA. In an alternate embodiment, cells produced by the methods of the present invention produce about 200 ng C-peptide/pg DNA. In an alternate embodiment, cells produced by the methods of the present invention produce about 100 ng C-peptide/pg DNA. In an alternate embodiment, cells produced by the methods of the present invention produce about 90 ng C-peptide/pg DNA. In an alternate embodiment, cells produced by the methods of the present invention produce about 80 ng C-peptide/pg DNA. In an alternate embodiment, cells produced by the methods of the present invention produce about 70 ng C-peptide/pg DNA. In an alternate embodiment, cells produced by the methods of the present invention produce about 60 ng C-peptide/pg DNA. In an alternate embodiment, cells produced by the methods of the present invention produce about 50 ng C-peptide/pg DNA. In an alternate embodiment, cells produced by the methods of the present invention produce about 40 ng C-peptide/pg DNA. In an alternate embodiment, cells produced by the methods of the present invention produce about 30 ng C-peptide/pg DNA. In an alternate embodiment, cells produced by the methods of the present invention produce about 20 ng C-peptide/pg DNA. In an alternate embodiment, cells produced by the methods of the present invention produce about 10 ng C-peptide/pg DNA.

Increasing Expression of MAFA in Cells Expressing Markers Characteristic of the Pancreatic Endocrine Lineage In one embodiment, the present invention provides a method for increasing the expression of MAFA in cells expressing markers characteristic of the pancreatic endocrine lineage comprising the steps of culturing the cells expressing markers characteristic of the pancreatic endocrine lineage in medium comprising a sufficient amount of a cyclin-dependant kinase inhibitor to cause an increase in expression of MAFA.

The cyclin dependant kinase inhibitor may inhibit cyclin dependant kinase 1. Alternatively, the cyclin dependant kinase inhibitor may inhibit cyclin dependant kinase 2. Alternatively, the cyclin dependant kinase inhibitor may inhibit cyclin dependant kinase 4. Alternatively, the cyclin dependant kinase inhibitor may inhibit cyclin dependant kinase 5. Alternatively, the cyclin dependant kinase inhibitor may inhibit cyclin dependant kinase 9. Alternatively, the cyclin dependant kinase inhibitor may inhibit multiple isoforms of cyclin dependant kinase, in any combination thereof.

The cyclin dependant kinase inhibitor may be a protein. Alternatively, the cyclin dependant kinase inhibitor may be a peptide. Alternatively, the cyclin dependant kinase inhibitor may be a small molecule. In one embodiment, the small molecule cyclin dependant kinase inhibitor is selected from the group consisting of 7-n-Butyl-6-(4-hydroxyphenyl)[5H]pyrrolo[2,3-b]pyrazine, 9-Nitro-7,12-dihydroindolo[3,2-d][1]benzazepin-6(5H)-one, 3-(6-oxo-9-nitro-5,6,7,12-tetrahydroindolo[3,2-d][1]benzazepin-2-yl)propionitrile, (2R)-2-((6-((3-Amino-5-chlorophenyl)amino)-9-(1-methylethyl)-9H-purin-2-yl)amino)-3-methyl-1-butanol, Arcyriaflavin A, [6-Benzylamino-2-(3-hydroxypropylamino)-9-isopropylpurine, Butyrolactone 1, (Z)-1-(3-Ethyl-5-methoxy-2,3-dihydrobenzothiazol-2-ylidene)propan-2-one, 2-(3-Hydroxypropylamino)-6-(o-hydroxybenzylamino)-9-isopropylpurine, Dichlorophenyl)-1,5-dihydro-6-((4-(2-hydroxyethoxy)phenyl)methyl)-3-(1-methylethyl)-4H-pyrazolo[3,4-d]pyrimidin-4-one, Cdk/Cyclin Inhibitory Peptide III. 3-(2-Chloro-3-indolylmethylene)-1,3-dihydroindol-2-one, Ethyl-(6-hydroxy-4-phenylbenzo[4,5]furo[2,3-b])pyridine-3-carboxylate, RO-3306, N-(cis-2-Aminocyclohexyl)-N-(3-chlorophenyl)-9-ethyl-9H-purine-2,6-diamine, 6-Cyclohexylmethoxy-2-(4'-sulfamoylanilino)purine, 5-Amino-3-((4-(aminosulfonyl)phenyl)amino)-N-(2,6-difluorophenyl)-1H-1,2,4-triazole-1-carbothioamide, 3-Amino-1H-pyrazolo[3,4-b]quinoxaline, Cdk2 Inhibitor I, Cdk2 Inhibitor II, 2(bis-(Hydroxyethyl)amino)-6-(4-methoxybenzylamino)-9-isopropylpurine, 4-(6-Cyclohexylmethoxy-9H-purin-2-ylamino)-N,N-diethylbenzamide, N4-(6-Aminopyrimidin-4-yl)-sulfanilamide, (4-(2-Amino-4-methylthiazol-5-yl)pyrimidin-2-yl)-(3-nitrophenyl)amine, 2-Bromo-12,13-dihydro-5H-indolo[2,3-a]pyrrolo[3,4-c]carbazole-5,7(6H)-dione, 1,4-Dimethoxyacridine-9(10H)-thione, 5-(N-(4-Methylphenyl)amino)-2-methyl-4,7-dioxobenzothiazole. 4-(3,5-Diamino-1Hpyrazol-4-ylazo)-phenol, 2-(2-Hydroxyethylamino)-6-(3-chloroanilino)-9-isopropylpurine, Fascaplysin, Indirubin-3'-monoxime, Indirubin-3'-monoxime, 5-Iodo-, Indirubin-3'-monoxime-5-sulphonic Acid, Isogranulatimide, 2-(2-Hydroxyethylamino)-6-benzylamino-9-methylpurine, 6-(2-Hydroxybenzylamino)-2-((1R)-(hydroxymethyl)propyl)amino)-9-isopropylpurine, 5-Bromo-3-(2-(4-Fluorophenyl)-2-oxoethylidine)-1,3-dihydroindol-2-one, N6,N6-Dimethyladenine, 2-((1R-Isopropyl-2-hydroxyethylamino)-6-(3-chloroanilino)-9-isopropyl-purine, rapamycin, 2-(R)-(1-Ethyl-2-hydroxyethylamino)-6-benzylamino-9-isopropylpurine, Scytonemin, 3-[1-(3H-Imidazol-4-yl)-meth-(Z)-ylidene]-5-methoxy-1,3-dihydroindol-2-one, and 4-(3'-Hydroxyphenyl)amino-6,7-dimethoxyquinazoline.

In one embodiment, the cyclin dependant kinase inhibitor is ethyl-(6-hydroxy-4-phenylbenzo[4,5]furo[2,3-b])pyridine-3-carboxylate. In one embodiment, ethyl-(6-hydroxy-4-phenylbenzo[4,5]furo[2,3-b])pyridine-3-carboxylate is added to cells expressing markers characteristic of the endocrine lineage at a concentration from about 0.1 µM to about 10 µM for about one to seven days.

In one embodiment, cells expressing markers characteristic of the endocrine lineage are treated with ethyl-(6-hydroxy-4-phenylbenzo[4,5]furo[2,3-b])pyridine-3-carboxylate for about one to about seven days.

The present invention is further illustrated, but not limited by, the following examples.

EXAMPLES

Example 1

Differentiation of Human Embryonic Stem Cells of the Cell Line H1 to Pancreatic Endocrine Cells in the Absence of Fetal Bovine Serum Cells of the human embryonic stem cells line H1 at passage 52 were cultured on MATRIGEL®-coated dishes (1:30 dilution) and exposed to the following differentiation protocol, in order to differentiate the cells to cells expressing markers characteristic of the pancreatic endocrine lineage.

a. RPMI medium supplemented with 2% BSA (Catalog#152401, MP Biomedical, Ohio), and 100 ng/ml activin A (R&D Systems, MN) plus 20 ng/ml WNT-3a (Catalog#1324-WN-002, R&D Systems, MN) plus 8 ng/ml of bFGF (Catalog#100-18B, PeproTech, NJ), for one day followed by treatment with RPM, media supplemented with 2% BSA and 100 ng/ml activin A plus 8 ng/ml of bFGF for an additional two days (Stage 1), then b. DMEM/F12+2% BSA+50 ng/ml FGF7+0.25 µM Cyclopamine-KAAD (#239804, Calbiochem, CA) for two days (Stage 2), then c. DMEM/F12+1% B27 (Invitrogen, CA)+50 ng/ml FGF7+0.25 µM Cyclopamine-KAAD+2 µM Retinoic acid (RA) (Sigma, Mo.)+100 ng/ml of Noggin (R & D Systems, MN) for four days (Stage 3), then d. DMEM/F12+1% B27 (Invitrogen, CA)+100 ng/ml Noggin+1 µM DAPT (a gamma-secretase inhibitor) (Catalog#565784, Calbiochem, CA)+1 µM ALK5 inhibitor II (Catalog#616452, Calbiochem. Ca)+100 ng/ml of Netrin-4 (R&D Systems, MN) for three days (Stage 4), then e. DMEM/F12+1% B27 (Invitrogen, CA)+1 µM ALK5 inhibitor II (Calbiochem, Ca) for seven days (Stage 5).

Medium was changed daily. At each stage the cell number was calculated using a hemocytometer and RNA was collected for PCR analysis. All samples were collected in triplicate.

Example 2

Screening of the Effects of Compounds from the EMD Kinase Inhibitor Library II on Cells that have been Treated According to the Differentiation Protocol Outlined in Example 1

Cells of the human embryonic stem cell line H1 at passage 44 were seeded onto MATRIGEL™ coated 24-well dishes (1:30 dilution), and differentiated according to the methods described in Example 1 up to stage 5. Following this, the cells were treated for four days in DMEM/F12+1% B27 containing a compound from an EMD Calbiochem compound library (Catalog#539745, Calbiochem, San Diego, Calif.) at a final concentration of 1 µM. Wells containing vehicle were included as a control. Throughout the protocol media was changed daily. All samples were treated in duplicate. At the completion of this treatment RNA was collected for PCR analysis. Samples were analyzed by real-time PCR for expression of insulin, glucagon, MAFA, and Arx4. Results are expressed as a ratio insulin/glucagon (FIG. 1, panel a), or MAFA versus ARX4 (FIG. 1, panel b) of the treated samples relative to the untreated control, as measured by real-time PCR. The corresponding PubChem Compound ID# for each well # is listed in Table 1.

Figure 1B:
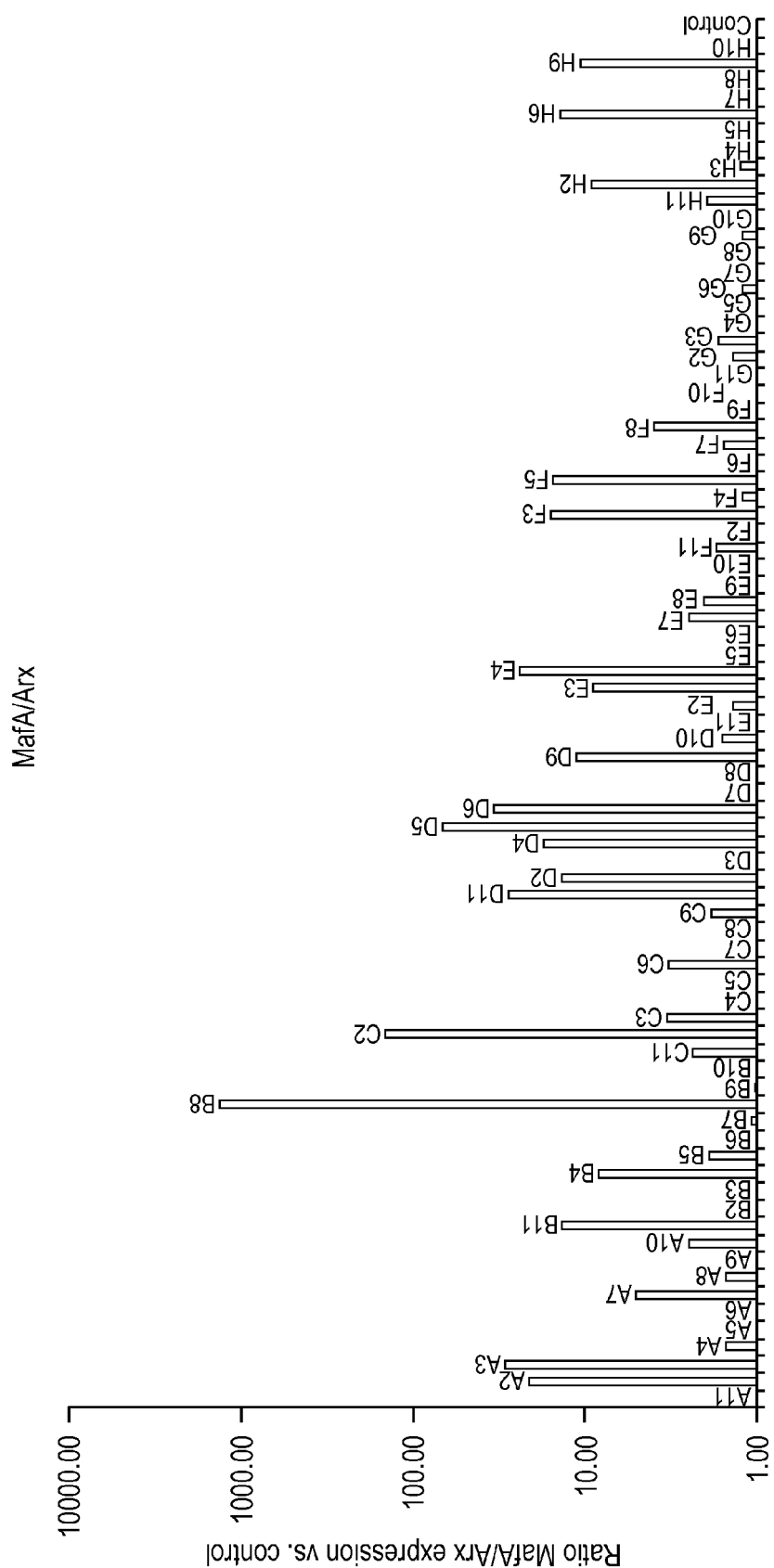
Figure 3A:
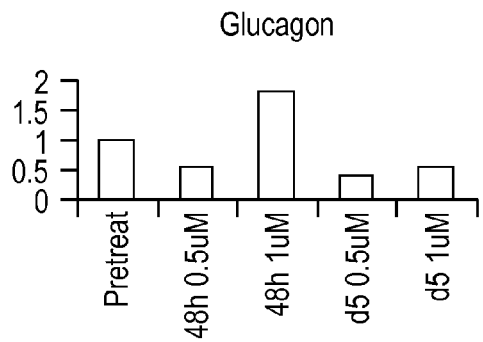
FIG. 3 shows the expression of the 23 genes indicated, in cells expressing markers characteristic of the pancreatic endocrine lineage following a five-day treatment of 0.5 µM (dark bars) or 1.0 µM (light bars) of the compound PubChem ID#5330812. Expression levels were determined at day 0, day 2 and day 5.
Figure 3B:
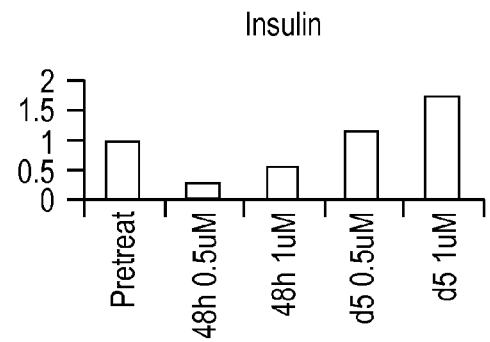
Figure 3C:
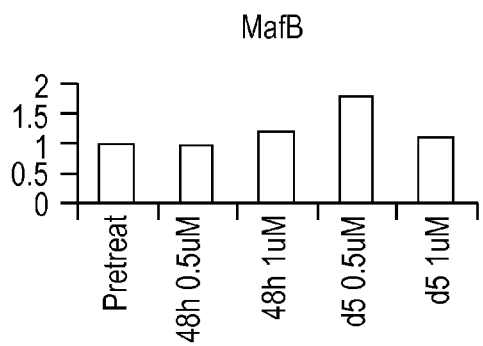
Figure 3D:
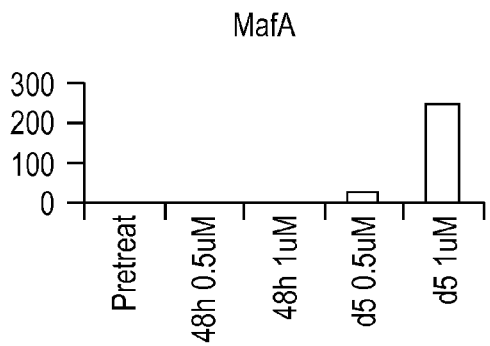
Figure 3E:
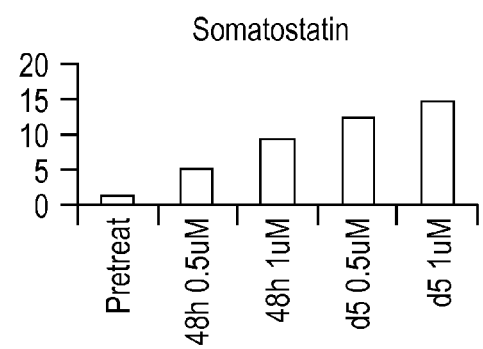
Figure 3F:
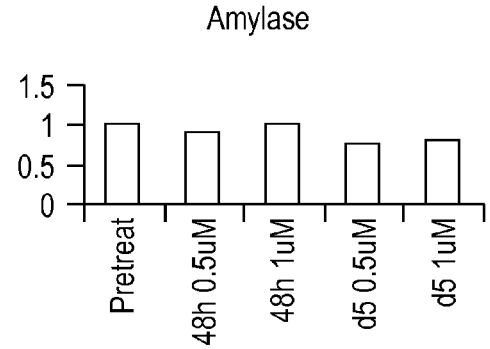
Figure 3G:
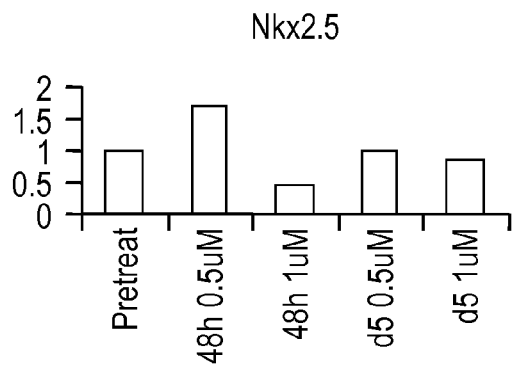
Figure 3H:
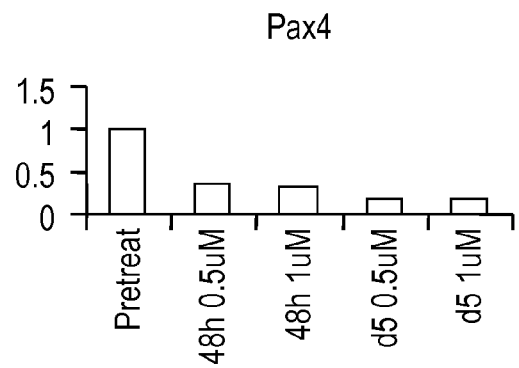
Figure 3I:
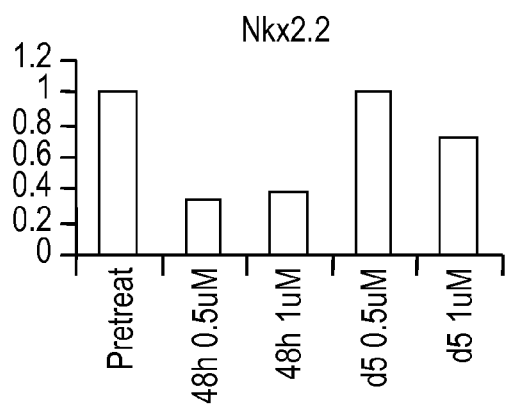
Figure 3J:
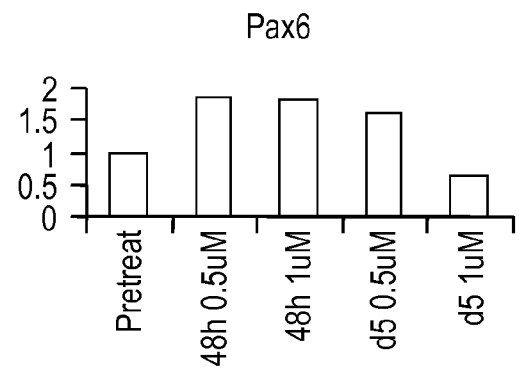
Figure 3K:
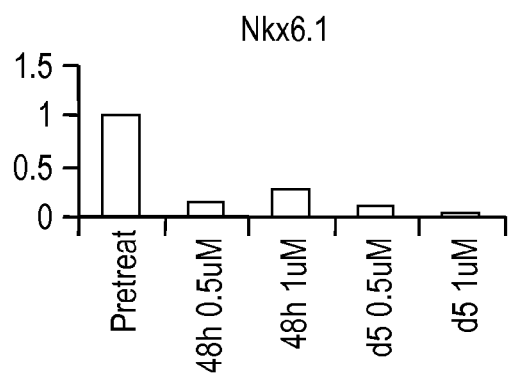
Figure 3L:
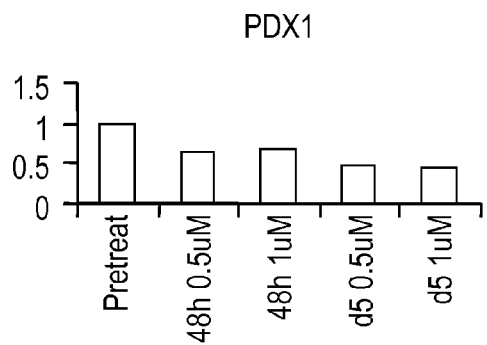
Figure 3M:
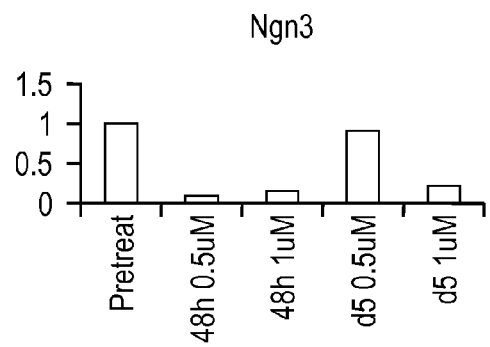
Figure 3N:
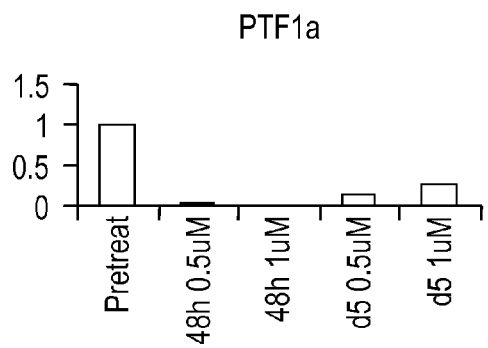
Figure 3O:
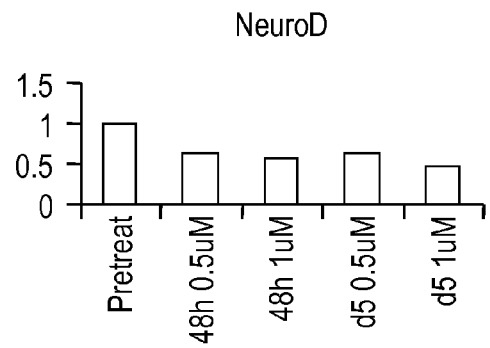
Figure 3P:
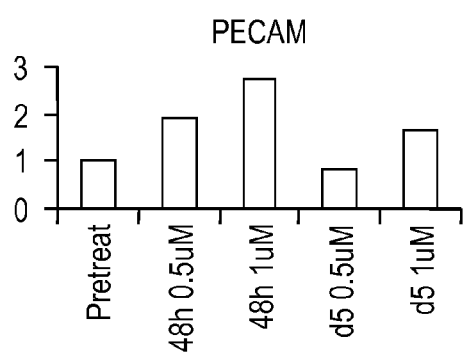
Figure 3Q:
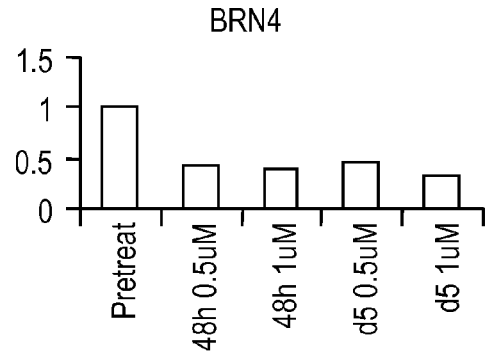
Figure 3R:
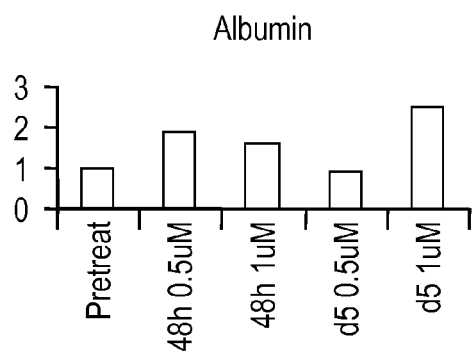
Figure 3S:
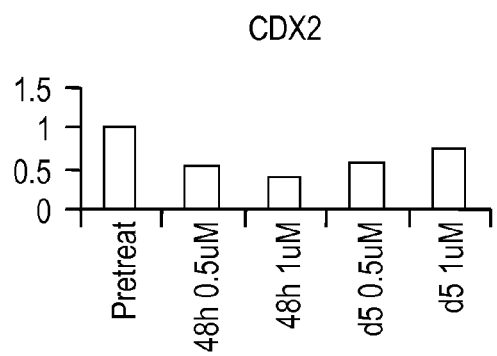
Figure 3T:
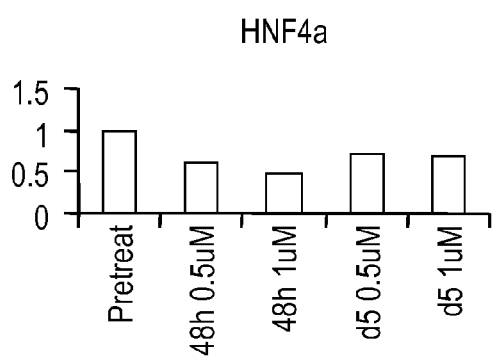
Figure 3U:
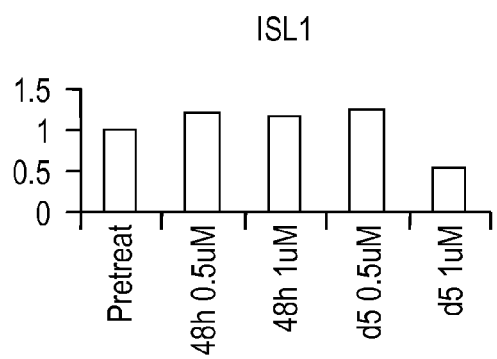
Figure 3V:
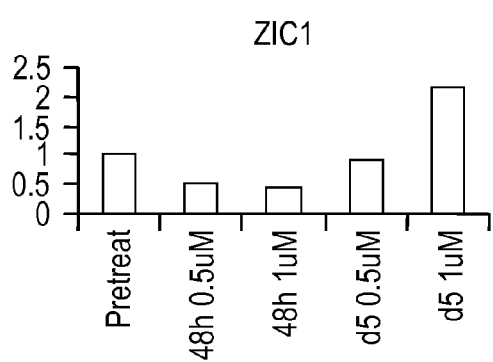
Figure 3W:
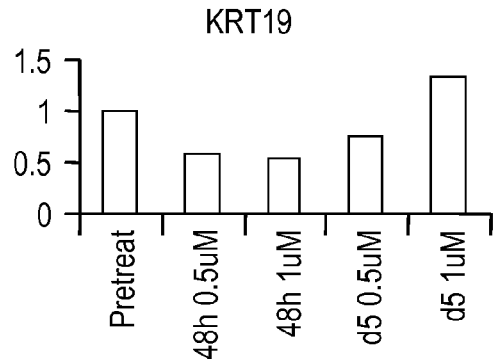
Figure 4A:
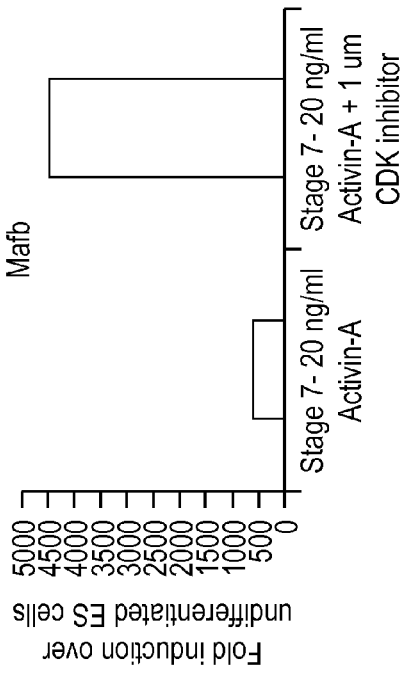
FIG. 4 shows the effect of CDK inhibitor III treatment on the expression of markers characteristic of the pancreatic endocrine lineage in cells treated with Stage 7 of the differentiation protocol described in Example 4.
Figure 4B:
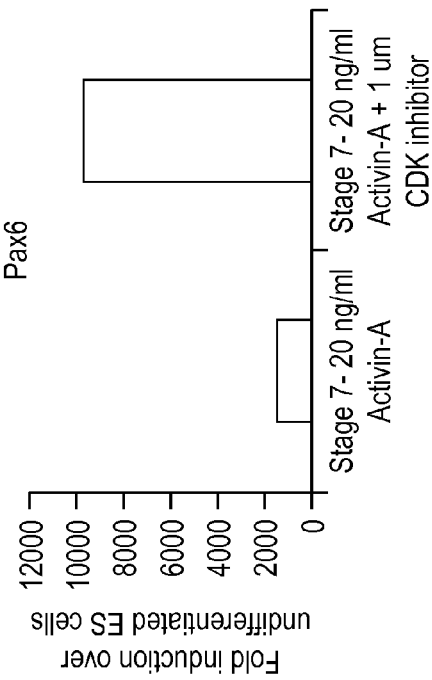
Figure 4C:
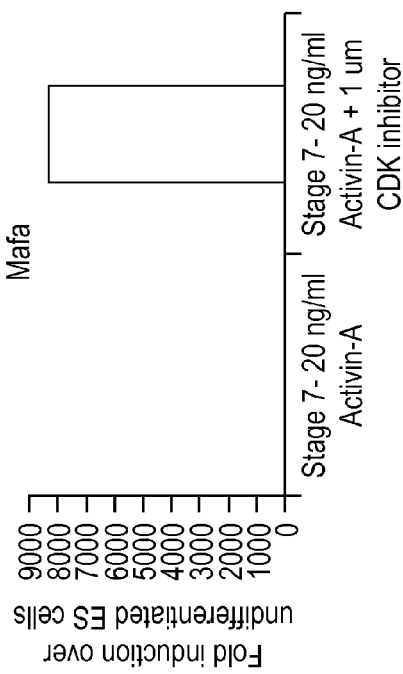
Figure 4D:
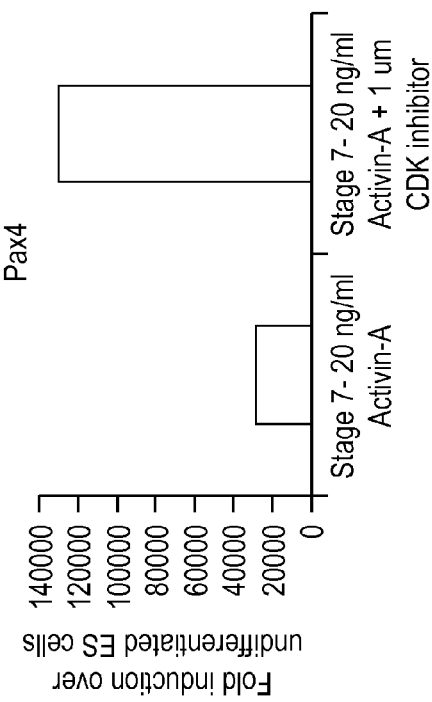
Figure 4I:
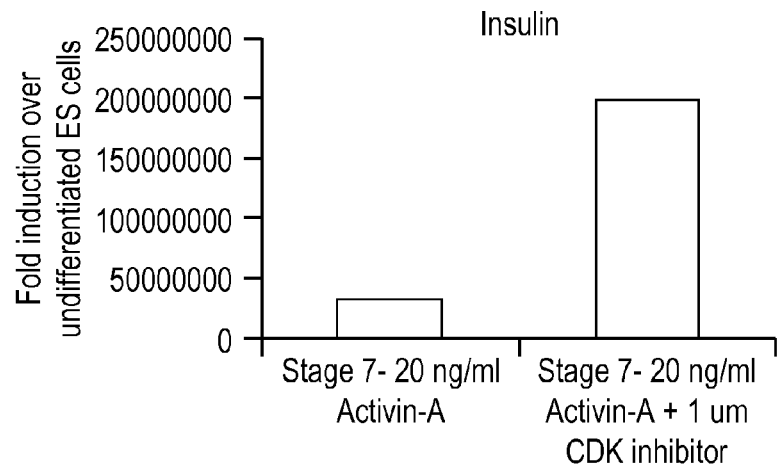

Treatment of cells expressing markers characteristic of the pancreatic endocrine lineage with compounds A6, B7, B8, or C2 at a 1 µM concentration resulted in an insulin/glucagon expression ratio of approximately 3.0 or higher (see FIG. 1, panel a).

We next examined the effect of these compounds on the ratio of MAFA/ARX4, and we observed that treatment of cells expressing markers characteristic of the pancreatic endocrine lineage with several of the compounds resulted in a much greater change in the ratio of MAFA to ARX4 than other compounds tested in the library: Cells treated with compound C2 showed a ratio of MAFA/ARX4 of approximately 1000. Treatment of cells expressing markers characteristic of the pancreatic endocrine lineage with compound C2 resulted in a MAFA/ARX4 ratio of approximately 100. (See FIG. 1, panel b).

Example 3

The Effects of Cyclin Dependant Kinase Inhibitor Treatment on Insulin and MAFA Expression in Cells that have been Treated According to the Differentiation Protocol Outlined in Example 1

Several of the compounds that increased the ratio of insulin to glucagon expression, or MAFA to ARX4 expression in Example 2 were cyclin dependant kinase inhibitors. One such compound was PubChem Compound ID#5330797 (5-Amino-3-((4-(aminosulfonyl)phenyl)amino)-N-(2,6-difluorophenyl)-1H-1,2,4-triazole-1-carbothioamide) (Catalogue #217714; Calbiochem, San Diego, Calif.). To confirm these observations, cells of the human embryonic stem cell line H1 at passage 42 were cultured in 10 cm² MATRIGEL®-coated dishes and treated according to the methods described in Example 1 up to stage 5. After stage 5, the cells were treated with DMEM/F12 containing 1% B27 containing 1 µM PubChem Compound ID#5330797 for six days. Medium was changed every other day. Samples of cells were taken for real-time PCR prior to treatment with the compound, and at days two and five of compound treatment.

Characteristic micrographs of the cells at day 4 or day 6 of compound treatment versus untreated controls are shown in FIG. 2. Untreated cells are highly packed (FIG. 3, panels a and d) and it is difficult to distinguish individual cells. However, after treatment with 0.5 µM or 1 µM of PubChem Compound ID#5330797 for six days, individual nuclei became visible (FIG. 2, panels e and f) as compared to the untreated control (FIG. 2, panel d), indicating that there was differentiation occurring in the cell population. This was also accompanied by some cell death, which can be seen by gaps in the layer of cells as shown in FIG. 2, panels b and c.

Treatment of cells with PubChem Compound ID#5330797 resulted in the increase in expression of insulin, glucagon, MAFA, MAFB and somatostatin, albeit to differing degrees. The relative induction of gene expression per treatment as compared to day 0 (pretreatment) cultures is shown in FIG. 3, panels a-v. Cells expressing markers characteristic of the pancreatic endocrine lineage that were treated with 1 µM PubChem Compound ID#5330797 resulted in an approximately 1.5 fold increase in glucagon expression at 48 hrs of treatment. This expression declined to below pretreatment levels after 5 days of treatment. No increase in glucagon expression was observed with treatment of 0.5 µM PubChem Compound ID#5330797. (See FIG. 3, panel a).

Cells expressing markers characteristic of the pancreatic endocrine lineage that were treated with 1 µM PubChem Compound ID#5330797 for five days resulted in an approximately 1.5 fold increase in insulin expression. (See FIG. 3, panel b).

Cells expressing markers characteristic of the pancreatic endocrine lineage that were treated with 1 µM PubChem Compound ID#5330797 for five days resulted in an approximately 200 fold increase in MAFA expression. (See FIG. 3, panel d).

Cells expressing markers characteristic of the pancreatic endocrine lineage that were treated with 0.5 µM PubChem Compound ID#5330797 for five days resulted in an approximately 1.5 fold increase in MAFB expression. (See FIG. 3, panel c). A dose-dependent increase in the expression of somatostatin was observed (FIG. 3, panel e).

No change in the expression of amylase was observed in cells expressing markers characteristic of the pancreatic endocrine lineage that were treated with PubChem Compound ID#5330797 for five days. (See FIG. 3, panel f). However, decreases in the level of expression of PAX4 (FIG. 3, panel h), NKX6.1 (FIG. 3, panel k), PDX1 (FIG. 3, panel l), NEUROD (FIG. 3, panel o), and BRN4 (FIG. 3, panel q) was observed.

Example 4

Cyclin Dependant Kinase Inhibitor Treatment Increased the Expression of MAFA in Islet-Like Clusters Cells of the human embryonic stem cell line H1 at passage 52 were cultured on MATRIGEL® coated dishes (1:30 dilution) and differentiated according to the methods described in Example 1. An additional stage (Stage 6) was added, in order to further mature the cells expressing markers characteristic of the pancreatic endocrine lineage. Stage 6 in this example consisted of a seven day treatment in DMEM/F12+1% B27 (Invitrogen, CA). The medium was changed daily.

After stage 6, the cells were treated for 5 mins at room temperature with 1× accutase (Sigma, Mo.). The accutase was removed, and DMEM/12+1% B27 was added to the cells. The attached cells were removed using a cell scarper and gently resuspended and passed through a 40 µm cell strainer. The cells retained on the strainer were removed by rinsing in basal media and cultured in suspension on Ultra-Low culture plates (Catalogue#3471, Corning, Ma). The cells were then treated as follows: The cells were cultured in DMEM/F12+1% B27, containing 20 ng/ml of activin A (AA), 1 µm of CDK inhibitor III (Catalog#217714, Calbiochem, Ca) for 10 days (Stage 7). Cells treated with vehicle were included as controls. Samples were collected at days 7 through 10 for PCR analysis and dithizone staining. The cells cultured in suspension according to the methods outlined in this example assumed a morphology similar to pancreatic islet clusters. Treatment with CDK inhibitor III did not appear to affect the morphology of the islet like clusters.

FIG. 4, panels a-i shows the effect of CDK inhibitor III treatment on gene expression profile of the cell clusters. Treatment with of CDK inhibitor III increased the expression of markers associated with the pancreatic endocrine lineage and in particular increased the expression of the pro-insulin transcription factor, MAFA.

Figure 5A:
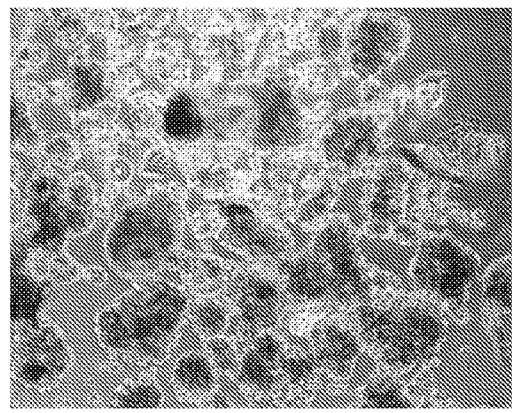
FIG. 5 shows the effect of CDK inhibitor III treatment on the dithazone staining of islet-like clusters.
Figure 5B:
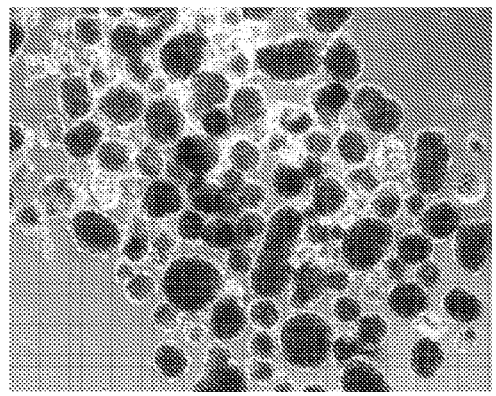

FIG. 5, panels a-b shows the effect of CDK inhibitor III on dithazone (DTZ) staining of clusters. Cell clusters treated with CDK inhibitor and stained with DTZ, showed a more reddish staining pattern as compared to clusters not treated with the CDK inhibitor III.

Example 5

FACS Analysis of Insulin Producing Cells Produced by the Methods of the Present Invention Cells of the human embryonic stem cell line H1 at passage 42 were cultured on MATRIGEL®-coated plates, and differentiated into insulin producing cells using the following protocol:
 a. RPMI medium supplemented with 2% BSA (Catalog#152401, MP Biomedical, Ohio), and 100 ng/ml activin A (R&D Systems, MN) plus 20 ng/ml WNT-3a (Catalog#1324-WN-002, R&D Systems, MN) plus 8 ng/ml of bFGF (Catalog#100-18B, PeproTech, NJ), for one day followed by treatment with RPMI media supplemented with 2% BSA and 100 ng/ml activin A plus 8 ng/ml of bFGF for an additional two days (Stage 1), then
 b. DMEM/F12+2% BSA+50 ng/ml FGF7+0.25 μM Cyclopamine-KAAD (#239804, Calbiochem, CA) for two days (Stage 2), then
 c. DMEM/F12+1% B27 (Invitrogen, CA)+50 ng/ml FGF7+0.25 μM Cyclopamine-KAAD+2 μM Retinoic acid (RA) (Sigma, Mo.)+100 ng/ml of Noggin (R & D Systems, MN) for four days (Stage 3), then
 d. DMEM/F12+1% B27 (Invitrogen, CA)+100 ng/ml Noggin+1 μM DAPT (a gamma-secretase inhibitor) (Catalog#565784, Calbiochem, CA)+1 μM ALK5 inhibitor II (Catalog#616452, Calbiochem, Ca)+100 ng/ml of Netrin-4 (R&D Systems, MN) for three days (Stage 4), then
 e. DMEM/F12+1% B27 (Invitrogen, CA)+1 μM ALK5 inhibitor II (Calbiochem, Ca) for seven days (Stage 5), then
 f. DMEM/F12+1% B27 for seven days (Stage 6), then
 g. Treatment with Accutase for 5 minutes, followed by scraping to remove any remaining attached cells. The cell suspension was then passed through a 40 μm cell strainer. The cells retained on the strainer were removed by rinsing in basal media and cultured in suspension on Ultra-Low culture plates in DMEM-High Glucose (Catalogue#11995-073, Invitrogen, Ca)+1% B27+20 ng/ml of activin A (AA) 1 μm of CDK inhibitor III (Catalog#217714, Calbiochem, Ca) for 5 days (Stage 7).

Islet-like clusters were dispersed into single cells using TrypLE Express (Invitrogen, Carlsbad, Calif.) and washed in cold PBS. For fixation, the cells were resuspended in 200-300 μl Cytofix/Cytoperm Buffer (BD 554722, BD, Ca) and incubated for 30 min at 4° C. Cells were washed two times in 1 ml Perm/Wash Buffer Solution (BD 554723) and resuspended in 100 μl staining/blocking solution containing 2% normal goat serum in Perm/Wash buffer. For flow cytometric analysis, cells were stained with the following primary antibodies: Anti-Insulin (Rabbit mAb, Cell Signaling No. C279; 1:100 dilution); Anti-Glucagon (Mouse Mab, Sigma No. G2654, 1:100); Anti-Synaptophysin (Rabbit Polyclonal antibody, DakoCytomation No A0010, 1:50). Cells were incubated for 30 min at 4° C. followed by two washes in Perm/Wash buffer and a further 30 min incubation in appropriate secondary antibodies as follows: Goat anti-Rabbit Alexa 647 (Invitrogen No. A21246) or Goat anti-Mouse 647 (Invitrogen No. A21235); Goat anti-Rabbit R-PE (BioSource No. AL14407). All secondary antibodies were used at a 1:200 dilution. Cells were washed at least once in Perm/Wash buffer and analyzed using BD FACSArray. At least 10,000 events were acquired for analysis. Controls included undifferentiated H1 cells and the β-TC (CRL-11506™ ATCC, VA) cell line.

Figure 6A:
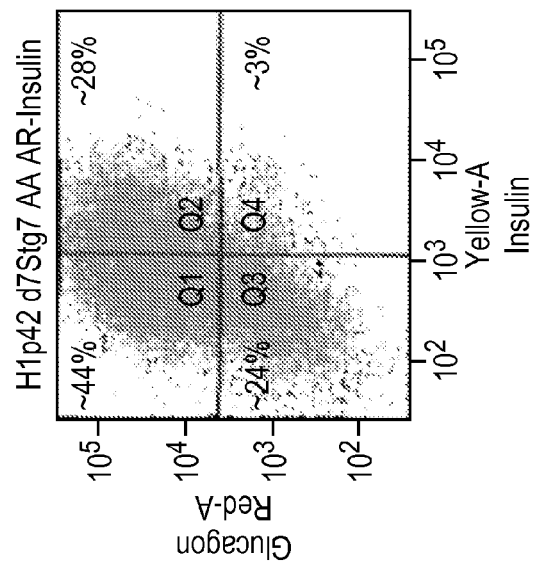
FIG. 6 shows the expression of insulin, synaptophysin and glucagon in insulin-producing cells produced according to the methods described in Example 5. Expression of the proteins indicated was determined by FACS.
Figure 6B:
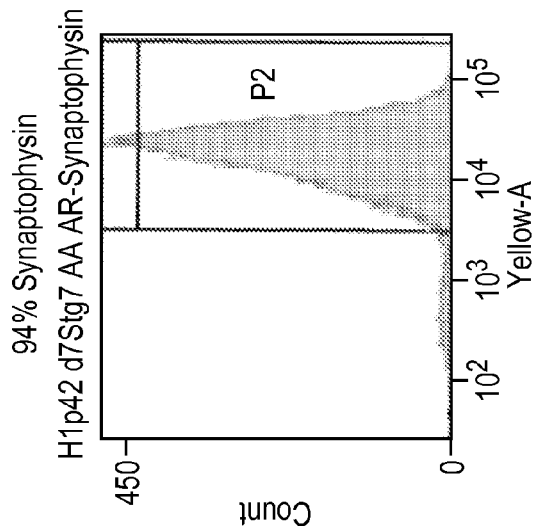
Figure 6C:
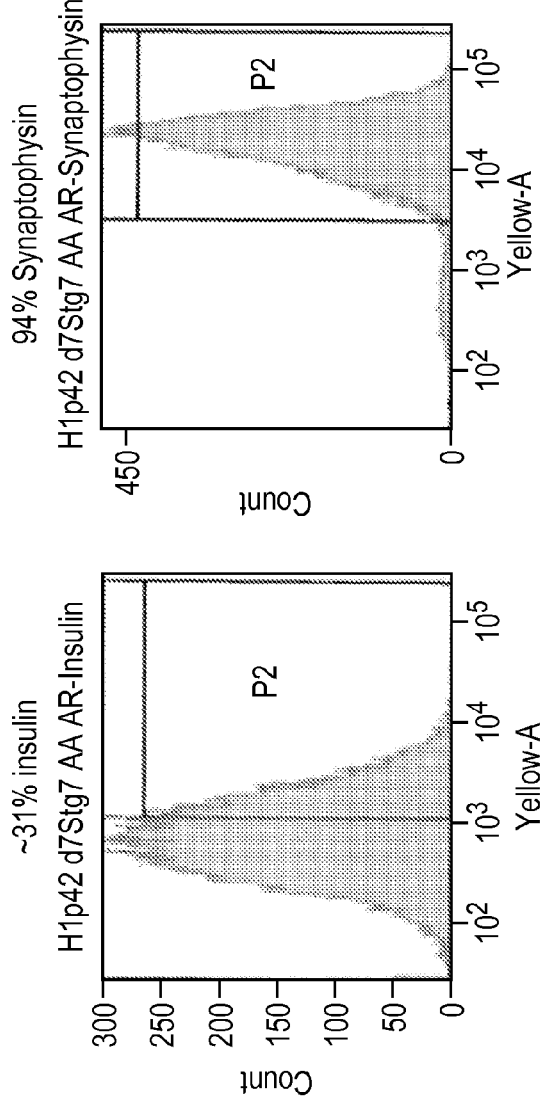
Figure 7C:
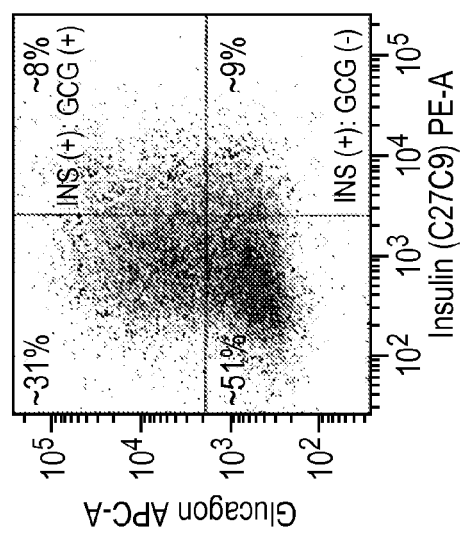
FIG. 7 shows the expression of insulin, synaptophysin and glucagon in insulin-producing cells produced according to the methods described in Example 5. Expression of the proteins indicated was determined by FACS.
Figure 7B:
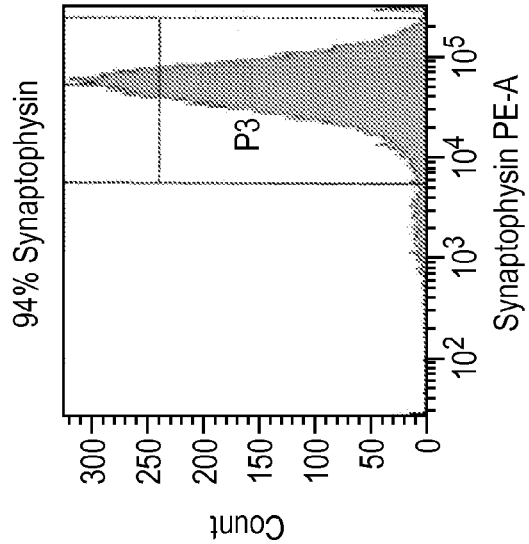
Figure 7A:
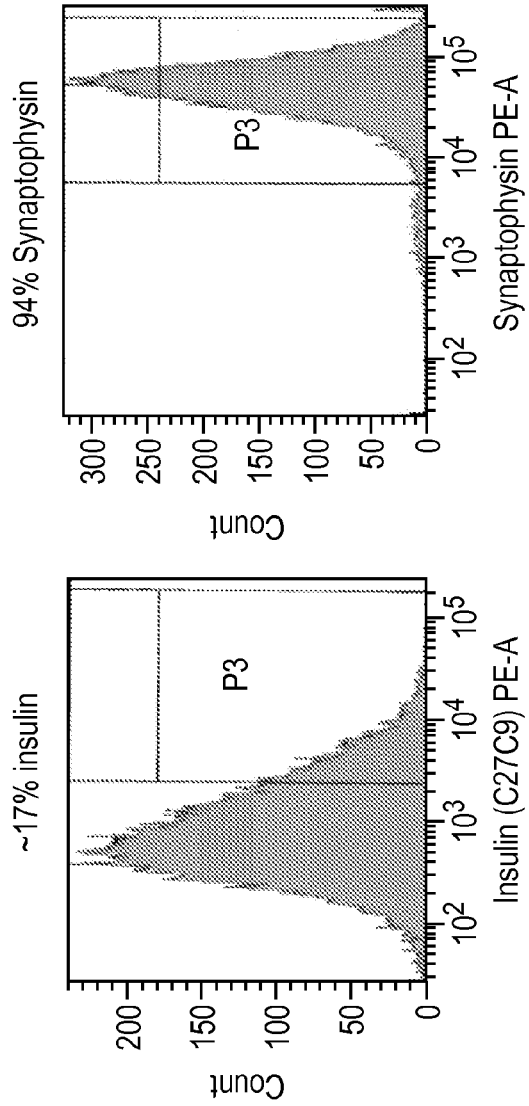

FIG. 6, panels a-c show the percentage insulin positive, synapthophysin positive, and glucagon positive cells in cells following treatment with Stage 7, in medium containing vehicle. FIG. 7, panels a-c shows the percentage insulin positive, synapthophysin positive, and glucagon positive cells following treatment with Stage 7 in medium containing 1 μM CDK inhibitor III for 5 days. The number of single hormonal insulin positive cells increased from 3% to 8% following treatment with the CDK inhibitor. Additionally, the percentage of poly hormonal (insulin and glucagon positive) cells decreased following treatment with the CDK inhibitor.

Example 6

Kinetics of CDK Inhibitor-Induced MAFA Expression

Cells of the human embryonic stem cell line H1 at passage 42 were cultured on MATRIGEL®-coated plates, and differentiated into insulin producing cells using the following protocol:
 a. RPMI medium supplemented with 2% BSA (Catalog#152401, MP Biomedical, Ohio), and 100 ng/ml activin A (R&D Systems. MN) plus 20 ng/ml WNT-3a (Catalog#1324-WN-002, R&D Systems, MN) plus 8 ng/ml of bFGF (Catalog#100-18B, PeproTech, NJ), for one day followed by treatment with RPMI media supplemented with 2% BSA and 100 ng/ml activin A plus 8 ng/ml of bFGF for an additional two days (Stage 1), then
 b. DMEM/F12+2% BSA+50 ng/ml FGF7+0.25 μM Cyclopamine-KAAD (#239804, Calbiochem, CA) for two days (Stage 2), then
 c. DMEM/F12+1% B27 (Invitrogen, CA)+50 ng/ml FGF7+0.25 μM Cyclopamine-KAAD+2 μM Retinoic acid (RA) (Sigma, Mo.)+100 ng/ml of Noggin (R & D Systems, MN) for four days (Stage 3), then
 d. DMEM/F12+1% B27 (Invitrogen, CA)+100 ng/ml Noggin+1 μM DAPT (a gamma-secretase inhibitor) (Catalog#565784, Calbiochem, CA)+1 μM ALK5 inhibitor II (Catalog#616452, Calbiochem, Ca)+100 ng/ml of Netrin-4 (R&D Systems, MN) for three days (Stage 4), then
 e. DMEM/F12+1% B27 (Invitrogen, CA)+1 μM ALK5 inhibitor II (Calbiochem, Ca) for seven days (Stage 5), then
 f. DMEM/F12+1% B27 for seven days (Stage 6), then
 g. Treatment with Accutase for 5 minutes, followed by scraping to remove any remaining attached cells. The cell suspension was then passed through a 40 μm cell strainer. The cells retained on the strainer were removed by rinsing in basal media and cultured in suspension on Ultra-Low culture plates in DMEM-High Glucose (Catalogue#11995-073, Invitrogen, Ca)+1% B27+20 ng/ml of activin A (AA) 2 μm of CDK inhibitor III (Catalog#217714, Calbiochem, Ca) for 1-8 days (Stage 7).

Samples were collected for PCR analysis at days 1, 2, 3, and 4. Following 4 days of treatment with CDK inhibitor, the CDK inhibitor was removed from culture and the cells were cultured additional 4 days in DMEM-F12+1% B27+20 ng/ml of activin A. At the end of the four days, samples were collected in triplicate for PCR analysis.

Figure 8A:
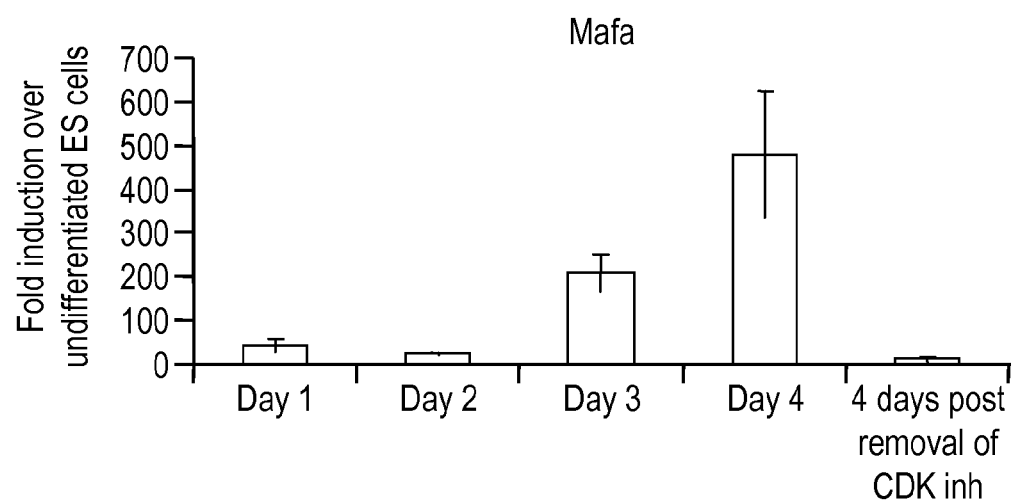
FIG. 8 shows the expression of MAFA (Panel a) and insulin (Panel b), in insulin-producing cells, produced by the methods of the present invention. Samples of cells were taken for PCR analysis at days 1, 2, 3, and 4. Following 4 days of treatment with CDK inhibitor, the CDK inhibitor was removed from culture and the cells were cultured additional 4 days in DMEM-F12+1% B27+20 ng/ml of activin A. At the end of the four days, samples were collected in triplicate for PCR analysis.
Figure 8B:
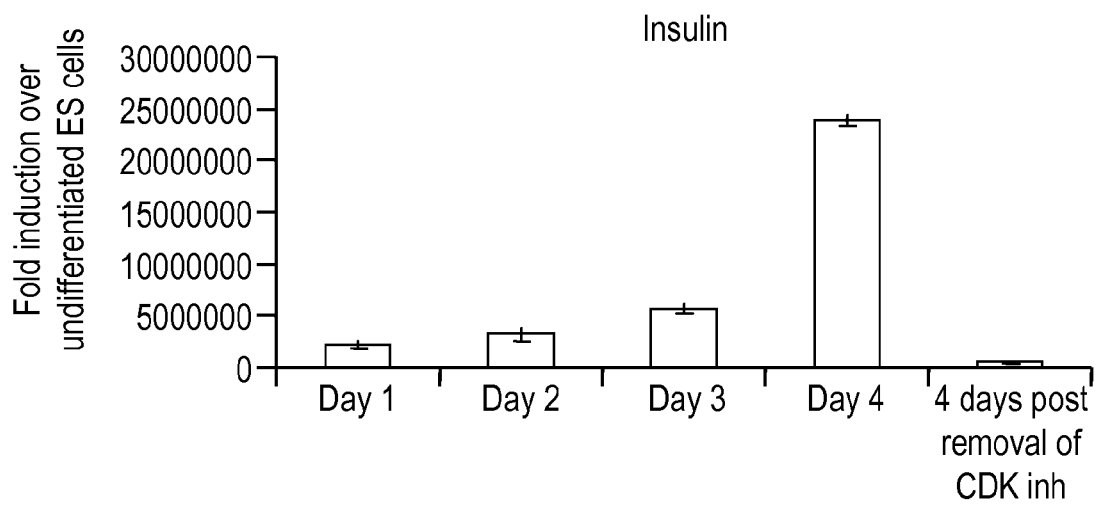
Figure 10A:
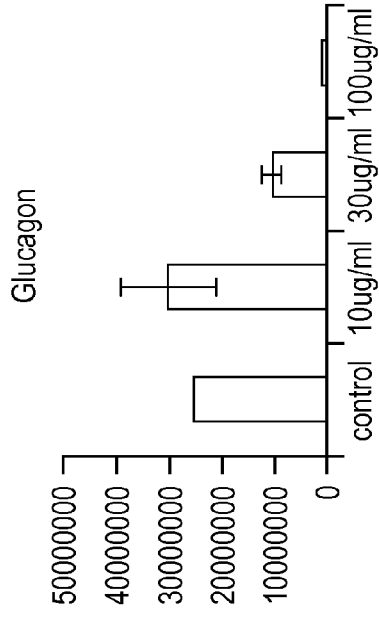
FIG. 10 shows the effect of genestein on the mRNA expression of insulin, glucagon, somatostatin and MAFA in cells expressing markers characteristic of the pancreatic endocrine lineage, as determined by real-time PCR.
Figure 10B:
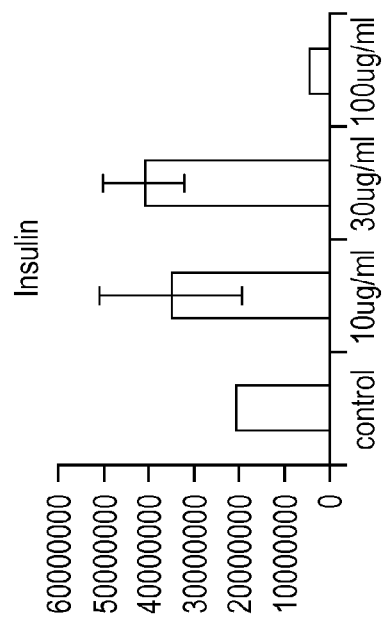
Figure 10C:
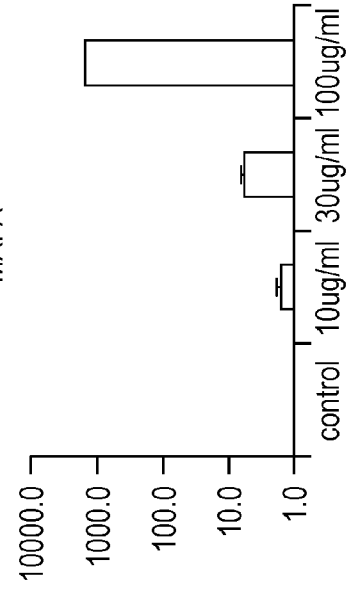
Figure 10D:
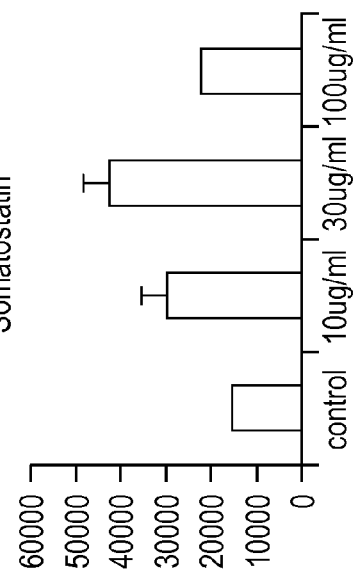

FIG. 8, panels a-b show expression pattern of MAFA and insulin at various time points of stage 7. CDK inhibitor treatment resulted in significant increase in MAFA and insulin expression which increased as a function of time. However, removal of CDK inhibitor resulted in a significant drop to both MAFA and insulin expression, in samples obtained four days after removal of the compound.

Example 7

Screening of the Effects of Compounds from the BIOMOL™ Kinase Inhibitor Library on Cells that have been Treated According to the Differentiation Protocol Outlined in Example 1

Cells of the human embryonic stem cell line H1 at passage 51 were seeded onto MATRIGEL®-coated 24-well dishes (1:30 dilution), and differentiated according to the methods described in Example 1 up to stage 5. Following this, the cells were grown for one day in DMEM/F12+1% B27 and then treated for six days in DMEM/F12+1% B27 containing a compound from a BIOMOL™ compound library (Catalog#2832, BIOMOL, Plymouth Meeting, Pa.) at a final concentration of 4 µM. Wells containing vehicle were included as a control. Throughout the treatment protocol media containing vehicle or compound was changed every other day. All samples were treated in duplicate. At the completion of this treatment RNA was collected for PCR analysis. Samples were analyzed by real-time PCR for expression of insulin, glucagon, MAFA, and ARX4. Results are expressed as a ratio insulin/glucagon (Table 2), or MAFA versus Arx4 (Table 2) of the treated samples relative to the untreated control, as measured by real-time PCR. The corresponding catalog#, CAS#, and compound name or ID number for each alpha numeric well# is listed in Table 3.

Treatment of cells expressing markers characteristic of the pancreatic endocrine lineage with compounds C8 or F1 at a 4 µM concentration resulted in an insulin/glucagon expression ratio of approximately 10.0 or higher. Cells treated with D9 had an insulin/glucagon expression ratio of approximately 1840.0 (Table 2).

We next examined the effect of these compounds on the ratio of MAFA/ARX4, and we observed that treatment of cells expressing markers characteristic of the pancreatic endocrine lineage with several of the compounds resulted in a much greater change in the ratio of MAFA to ARX4 than other compounds tested in the library: Cells treated with compound B6 or F1 showed a ratio of MAFA/ARX4 of approximately greater than 10. Treatment of cells expressing markers characteristic of the pancreatic endocrine lineage with compound C8 resulted in a MAFA/ARX4 ratio of approximately 84, while cells treated with D9 had a MAFA/ARX4 ratio of approximately 212. (Table 2).

Example 8

The Effect of Cyclin Dependant Kinase Inhibitors on Insulin and MAFA Expression in Cells Treated According to the Differentiation Protocol Outlined in Example 1

Cells of the human embryonic stem cell line H1 at passage 51 were seeded onto MATRIGEL™ coated 24-well dishes (1:30 dilution), and differentiated according to the methods described in Example 1 up to stage 5. Following this, the cells were grown for eight days in DMEM/F12+1% B27 and then treated for four days in DMEM/F12+1% B27 containing a cyclin dependent kinase inhibitor at a final concentration of 0.6125, 1.25, or 5.0 µM. We tested 6 inhibitors: PubChem ID#5330812 (EMD cat#217714), PubChem ID#4566 (EMD cat#217713), PubChem ID#5330797 (EMD cat#219476), PubChem ID#73292 (EMD cat#341251), PubChem ID#4592 (EMD cat#495620), and PubChem ID#160355 (EMD cat #557360). Wells containing vehicle were included as a control. Throughout the treatment protocol media containing vehicle or compound was changed every other day. All samples were treated in duplicate. At the completion of this treatment RNA was collected for PCR analysis. Samples were analyzed by real-time PCR for expression of insulin, glucagon, MAFA, and ARX4. Results are expressed as the fold change relative to the vehicle treated control, as measured by real-time PCR.

We observed that the compounds PubChem ID#5330812, PubChem ID#4566, PubChem ID#5330797, and PubChem ID#73292 all stimulated MAFA expression at the concentrations tested (Table 4). PubChem ID#4592 and PubChem ID#160355 did not stimulate MAFA at the concentrations tested (Table 4). The compounds PubChem ID#5330812, PubChem ID#4566, PubChem ID#5330797, PubChem ID#4592 and PubChem ID#160355 all appeared to stimulate insulin expression (Table 4). The compound PubChem ID#5330797 reduced both glucagon and Arx4 expression (Table 4) while stimulating MAFA expression.

Example 9

Differentiation of Human Embryonic Stem Cells of the Cell Line H1 to Pancreatic Endocrine Cells with DMEM Containing 25 mM Glucose (DMEM-HG), Lacking Fetal Bovine Serum Cells of the human embryonic stem cells line H1 were cultured on MATRIGEL®-coated dishes (1:30 dilution) and differentiated into cells expressing markers characteristic of the pancreatic endocrine lineage using the following protocol:

a. RPMI medium supplemented with 2% BSA (Catalog#152401, MP Biomedical, Ohio), and 100 ng/ml activin A (R&D Systems, MN) plus 20 ng/ml WNT-3a (Catalog#1324-WN-002, R&D Systems, MN) plus 8 ng/ml of bFGF (Catalog#100-18B, PeproTech, NJ), for one day followed by treatment with RPMI media supplemented with 2% BSA and 100 ng/ml activin A plus 8 ng/ml of bFGF for an additional two days (Stage 1), then b. RPMI medium supplemented with 2% BSA+50 ng/ml FGF7+0.25 µM Cyclopamine-KAAD (#239804, Calbiochem, CA) for two days (Stage 2), then c. DMEM-HG+1% B27 (Invitrogen, CA)+50 ng/ml FGF7+0.25 µM Cyclopamine-KAAD+2 µM Retinoic acid (RA) (Sigma, Mo.)+100 ng/ml of Noggin (R & D Systems, MN) for six days (Stage 3), then d. DMEM-HG+1% B27 (Invitrogen, CA)+100 ng/ml Noggin+1 µM ALK5 inhibitor II (Catalog#616452, Calbiochem, Ca) for three days (Stage 4), then e. DMEM-HG+1% B27 (Invitrogen, CA)+1 µM ALK5 inhibitor II (Calbiochem, Ca) for seven days (Stage 5).

Medium was changed daily. At each stage the cell number was calculated using a hemocytometer and RNA was collected for PCR analysis. All samples were collected in triplicate.

Example 10

Screening of the Effects of Compounds from the EMD Kinase Inhibitor Library I on Cells Treated According to the Differentiation Protocol Outlined in Example 9

Cells of the human embryonic stem cell line H1 at passage 45 were seeded onto MATRIGEL®-coated 24-well dishes (1:30 dilution), and differentiated according to the methods described in Example 9 up to stage 5. Following this, the cells were fed and treated on day 1, 3, and 5 of stage 5 with media comprising DMEM-HG, 1% B27 (Invitrogen, CA), 1 µM ALK5 inhibitor II (Calbiochem, Ca) and a compound from an EMD Calbiochem compound library 1 solubilized in DMSO (Catalog#539744, Calbiochem, San Diego, Calif.) and treated at a final concentration of 2.5 µM. Wells containing vehicle were included as a control. Throughout the protocol media was changed daily except at stage 5 when media was changed every other day. All samples were treated in duplicate.

At the completion of this treatment RNA was collected for PCR analysis. Samples were analyzed by real-time PCR for expression of MAFA. Results are expressed as the fold increase in MAFA expression versus untreated H1 human embryonic stein cells (Table 5), as measured by real-time PCR.

Treatment of cells expressing markers characteristic of the pancreatic endocrine lineage with compounds A4 (Cat#, 124001, Akt Inhibitor IV), E8 (Cat#527450. PKR Inhibitor), and F9 (Cat#539648, Staurosporine, N-benzoyl-) at a 2.5 µM concentration resulted in an increase in MAFA expression at least 4 fold higher than vehicle treated controls (Table 5). Treatment with the compound E6 (Cat#521233, PDGF Receptor Tyrosine Kinase Inhibitor IV) at a 2.5 µM concentration resulted in an increase in MAFA expression at least 2.5 fold higher than vehicle treated controls (Table 5).

Example 11

Screening of the Effects of Compounds from the EMD Kinase Inhibitor Library II on Cells Treated According to the Differentiation Protocol Outlined in Example 9

Cells of the human embryonic stem cell line H1 at passage 46 were seeded onto MATRIGEL®-coated 24-well dishes (1:30 dilution), and differentiated according to the methods described in Example 9 up to stage 5. Following this, the cells were fed and treated on day 1, 3, and 5 of stage 5 with media comprising DMEM-HG, 1% B27 (Invitrogen, CA), 1 µM ALK5 inhibitor II (Calbiochem, Ca) (Stage 5) and a compound from an EMD Calbiochem compound library II solubilized in DMSO (Tables 1 and 6, Calbiochem, San Diego, Calif.) and treated at a final concentration of 2.5 µM. Wells containing vehicle were included as a control. Throughout the protocol media was changed daily except at stage 5 when media was changed every other day. All samples were treated in duplicate.

At the completion of this treatment RNA was collected for PCR analysis. Samples were analyzed by real-time PCR for expression of MAFA. Results for compounds that stimulated the expression of MAFA are shown and expressed as the fold increase in MAFA expression versus control samples (FIG. 9), as measured by real-time PCR.

Treatment of cells expressing markers characteristic of the pancreatic endocrine lineage with either: Alsterpaullone, 2-Cyanoethyl; SU9516; Alsterpaullone; Cdk1/2 Inhibitor III; Casein Kinase I Inhibitor, D4476; or MEK1/2 Inhibitor at a 2.5 µM concentration resulted in a 4.5 fold increase in MAFA expression versus untreated controls (Table 7).

Example 12

Inhibiting Cell Cycle Progression in Cells Expressing Markers Characteristic of the Pancreatic Endocrine Lineage with Small Molecule Inhibitors Promotes MAFA Expression in Cells Expressing Markers Characteristic of the Pancreatic Endocrine Lineage Cell growth resulting from cell cycle progression can be activated and maintained by stimulating cells with extracellular growth factors. Growth factors bind to the extracellular domains of growth factor receptors, inducing a conformational switch in the receptor's intracellular domain. This shift initiates receptor dimerization and activation of tyrosine kinases located on the intracellular domain of the receptor leading to phosphorylation and activation of multiple serine/threonine kinases downstream, ultimately resulting in cell cycle progression and cell proliferation.

Under normal physiologic conditions mature pancreatic beta cells, characterized by expression of insulin and the transcription factor MAFA, are quiescent and tend to remain in G0 of the cell cycle. Yet, in order to generate enough cells to form a functional organ and meet the needs of a mature animal, the cells expressing markers characteristic of the pancreatic endocrine lineage of the present invention must be cell cycling. Consequently, at some point in embryonic development, the cells expressing markers characteristic of the pancreatic endocrine lineage of the present invention differentiate to beta cells and transition from an actively cell-cycling proliferating cell, to a quiescent cell.

Our data indicate that by inhibiting cell cycle progression by blocking signaling cascades with small molecule kinase inhibitors, we can induce the cells expressing markers characteristic of the pancreatic endocrine lineage to express MAFA, a marker of mature pancreatic beta cells. Kinase inhibitors targeted to a growth factor receptor, (PDGF Receptor Tyrosine Kinase Inhibitor IV), or inhibitors which disrupt kinases downstream of tyrosine kinase receptors (MEK1/2 Inhibitor, PKR Inhibitor, or Akt Inhibitor IV) disrupt proliferative growth factor/kinase based signaling resulting in cell cycle arrest and induction of MAFA expression. Use of a broad spectrum inhibitor like staurosporine, can effectively induce MAFA, however it is also cytotoxic at effective concentrations. More directed compounds like cyclin dependent kinase inhibitors (Alsterpaullone, 2-Cyanoethyl; SU9516; Alsterpaullone; or Cdk1/2 Inhibitor III) induce MAFA with less toxicity than a broad spectrum inhibitor like staurosporine.

In order to determine if a broad spectrum kinase inhibitor could induce MAFA expression and a more mature phenotype in the cells expressing markers characteristic of the pancreatic endocrine lineage of the present invention we differentiated H1 human ES cells according to the methods described in example 9, and treated them on days 1, 3, and 5 of stage 5 with the protein-tyrosine kinase inhibitor, Genistein, which has been shown to induce G2 phase arrest in human and murine cell lines and inhibit multiple kinases. At doses of 10 and 30 ng/ml the endocrine hormones insulin, somatostatin, and the transcription factor MAFA, all showed increased expression versus untreated controls, while at 10 ng/ml the endocrine hormone glucagon had increased expression (FIG. 10). We observed significant toxicity at a 100 ng/ml dose of genistein that correlated with loss of insulin, glucagon, and somatostatin expression.

These data indicate that by inhibiting cell cycle progression by blocking signaling cascades with small molecule kinase inhibitors targeted to inhibit signal transduction from a growth factor receptor tyrosine kinase through intracellular signaling kinases to the nucleus and cyclin dependent kinases, we can induce the cells expressing markers characteristic of the pancreatic endocrine lineage of the present invention to express MAFA, a marker of mature pancreatic beta cells.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

TABLE 1

AlphaNumeric Well Label and the Corresponding PubChem ID# for EMD Calbiochem ® Kinase Inhibitor II compound library

| Well | PubChemID# | Well | PubChemID# | Well | PubChemID# | Well | PubChemID# |
|---|---|---|---|---|---|---|---|
| A2 | 16760529 | B2 | 16760303 | C2 | 5330797 | D2 | 9797929 |
| A3 | 5278396 | B3 | 5326739 | C3 | 3004085 | D3 | 11493598 |
| A4 | 6605258 | B4 | 5353431 | C4 | 481747 | D4 | 16760417 |
| A5 | 5005498 | B5 | 2422 | C5 | 1893668 | D5 | 73292 |
| A6 | 16760286 | B6 | 5472558 | C6 | 9969021 | D6 | 4124851 |
| A7 | 5326843 | B7 | 2794188 | C7 | 2856 | D7 | 6539732 |
| A8 | 3641059 | B8 | 5330812 | C8 | 6918386 | D8 | 448014 |
| A9 | 6604931 | B9 | 438981 | C9 | 10202471 | D9 | 5287844 |
| A10 | 11524144 | B10 | 6419753 | C10 | 9549301 | D10 | 6538818 |
| A11 | 9549303 | B11 | 16760346 | C11 | 5339183 | D11 | 10020713 |
| E2 | 5312137 | F2 | 11382492 | G2 | 6419739 | H2 | 176155 |
| E3 | 6419766 | F3 | 11624601 | G3 | 4665 | H3 | 16219471 |
| E4 | 6419741 | F4 | 490561 | G4 | 4713 | H4 | 3387354 |
| E5 | 3674 | F5 | 3820 | G5 | 4712 | H5 | 5174 |
| E6 | 9903786 | F6 | 5312122 | G6 | 5164 | H6 | 5228 |
| E7 | 6419764 | F7 | 9951490 | G7 | 4987 | H7 | 16760659 |
| E8 | 8515 | F8 | 389898 | G8 | 9549289 | H8 | 451705 |
| E9 | 11665831 | F9 | 9549284 | G9 | 5702541 | H9 | 16760660 |
| E10 | 11422035 | F10 | 11644425 | G10 | 5162 | H10 | 5289419 |
| E11 | 16760525 | F11 | 509554 | G11 | 5353940 | H11 | 9549300 |

TABLE 2

The Effect of compounds of the BIOMOL Inhibitor compound library on the Ratio of Insulin/glucagon and MAFA/Arx4 expression as determined by real-time PCR in Cells Expressing Markers Characteristic of the Pancreatic Endocrine Lineage.

| | Ratio vs. Control | |
|---|---|---|
| Well # | Insulin to Glucagon | MAFA to Arx4 |
| B1 | 1.6 | 0.9 |
| B2 | 2.4 | 1.3 |
| B3 | 2.9 | 2.9 |
| B4 | 1.1 | 2.0 |
| B5 | 1.3 | 1.3 |
| B6 | 1.6 | 16.3 |
| B7 | 1.3 | 0.5 |
| B8 | 1.6 | 0.5 |
| B9 | 1.1 | 1.5 |
| B10 | 1.2 | 1.5 |
| B11 | 1.1 | 2.1 |
| B12 | 1.0 | 2.0 |
| C1 | 0.7 | 0.8 |
| C2 | 0.9 | 1.0 |
| C3 | 1.3 | 0.9 |
| C4 | 1.2 | 1.7 |
| C5 | 1.0 | 1.1 |
| C6 | 1.6 | 1.2 |
| C7 | 4.3 | 0.2 |
| C8 | 40.2 | 84.3 |
| C9 | 0.8 | 0.5 |
| C10 | 2.3 | 1.9 |
| C11 | 1.1 | 0.4 |
| C12 | 1.0 | 0.4 |
| D1 | 2.7 | 1.2 |
| D2 | 3.4 | 1.3 |
| D3 | 1.7 | 2.1 |
| D4 | 5.8 | 6.4 |
| D5 | 1.4 | 1.1 |
| D6 | 1.8 | 3.9 |
| D7 | 1.7 | 0.6 |
| D8 | 2.8 | 5.1 |
| D9 | 1842.5 | 212.6 |
| D10 | 0.9 | 1.3 |
| D11 | 1.0 | 0.7 |
| D12 | 1.1 | 2.5 |
| E1 | 1.1 | 0.9 |
| E2 | 0.8 | 0.8 |
| E3 | 1.2 | 1.0 |
| E4 | 2.1 | 1.3 |
| E5 | 1.3 | 1.1 |
| E6 | 2.0 | 1.5 |
| E7 | 4.8 | 0.2 |

TABLE 2-continued

The Effect of compounds of the BIOMOL Inhibitor compound library on the Ratio of Insulin/glucagon and MAFA/Arx4 expression as determined by real-time PCR in Cells Expressing Markers Characteristic of the Pancreatic Endocrine Lineage.

| Well # | Insulin to Glucagon | MAFA to Arx4 |
|---|---|---|
| E8 | 3.7 | 0.0 |
| E9 | 1.0 | 0.8 |
| E10 | 0.6 | 0.2 |
| E11 | 1.0 | 0.3 |
| E12 | 0.8 | 0.2 |
| F1 | 10.3 | 9.5 |
| F2 | 2.9 | 1.9 |
| F3 | 2.6 | 2.5 |
| F4 | 1.5 | 2.7 |
| F5 | 1.9 | 1.4 |
| F6 | 1.6 | 1.2 |
| F7 | 1.9 | 0.6 |
| F8 | 1.5 | 0.6 |
| F9 | 1.0 | 1.4 |
| F10 | 5.4 | 3.4 |
| F11 | 0.8 | 1.9 |
| F12 | 1.0 | 1.4 |
| G1 | 0.8 | 1.2 |
| G2 | 0.6 | 1.1 |
| G3 | 2.0 | 1.6 |
| G4 | 1.3 | 1.6 |
| G5 | 1.7 | 1.5 |
| G6 | 1.5 | 1.3 |
| G7 | 4.6 | 0.2 |
| G8 | 3.9 | 0.4 |
| G9 | 1.0 | 0.7 |
| G10 | 1.3 | 0.7 |
| G11 | 1.9 | 0.6 |
| G12 | 1.4 | 0.8 |
| H1 | 3.1 | 0.6 |
| H2 | 1.8 | 3.5 |
| H3 | 1.8 | 3.9 |
| H4 | 1.2 | 4.0 |
| H5 | 1.8 | 2.0 |
| H6 | 1.4 | 2.9 |
| H7 | 1.5 | 0.6 |
| H8 | 2.1 | 0.8 |
| vehicle control | 1.0 | 1.0 |

The AlphaNumeric well# corresponds to the compound identity in Table 3.

TABLE 3

AlphaNumeric Well Label and the Corresponding Catalog#, CAS#, and Compound Name or ID Number for the BIOMOL Kinase Inhibitor compound library

| PLATE LOCATION | CATALOG # | CAS # | COMPOUND NAME OR ID NUMBER |
|---|---|---|---|
| B1 | EI-360 | 167869-21-8 | PD-98059 |
| B2 | EI-282 | 109511-58-2 | U-0126 |
| B3 | EI-286 | 152121-47-6 | SB-203580 |
| B4 | EI-148 | 84477-87-2 | H-7 |
| B5 | EI-195 | 84468-17-7 | H-9 |
| B6 | EI-156 | 62996-74-1 | Staurosporine |
| B7 | EI-228 | 133550-35-5 | AG-494 |
| B8 | EI-267 | | AG-825 |
| B9 | EI-185 | 125697-92-9 | Lavendustin A |
| B10 | EI-253 | 136831-49-7 | RG-14620 |
| B11 | EI-191 | 118409-57-7 | Tyrphostin 23 |
| B12 | EI-187 | 118409-58-8 | Tyrphostin 25 |
| C1 | EI-257 | 122520-85-8 | Tyrphostin 46 |
| C2 | EI-188 | 122520-86-9 | Tyrphostin 47 |
| C3 | EI-189 | 122520-90-5 | Tyrphostin 51 |
| C4 | EI-190 | 2826-26-8 | Tyrphostin 1 |
| C5 | EI-335 | 116313-73-6 | Tyrphostin AG 1288 |
| C6 | EI-277 | 63177-57-1 | Tyrphostin AG 1478 |
| C7 | AC-1133 | 71897-07-9 | Tyrphostin AG 1295 |
| C8 | EI-215 | 10537-47-0 | Tyrphostin 9 |
| C9 | EI-247 | | HNMPA (Hydroxy-2-naphthalenylmethylphosphonic acid) |
| C10 | EI-370 | 120685-11-2 | PKC-412 |
| C11 | EI-271 | 10083-24-6 | Piceatannol |
| C12 | EI-275 | 172889-26-8 | PP1 |
| D1 | EI-272 | 133550-35-3 | AG-490 |
| D2 | EI-263 | | AG-126 |
| D3 | EI-229 | | AG-370 |
| D4 | EI-258 | | AG-879 |
| D5 | ST-420 | 154447-36-6 | LY 294002 |
| D6 | ST-415 | 19545-26-7 | Wortmannin |
| D7 | EI-246 | 133052-90-1 | GF 109203X |
| D8 | EI-226 | 548-04-9 | Hypericin |
| D9 | EI-283 | 138489-18-6 | Ro 31-8220 |
| D10 | EI-155 | 123-78-4 | Sphingosine |
| D11 | EI-196 | 127243-85-0 | H-89 |
| D12 | EI-158 | 84478-11-5 | H-8 |
| E1 | EI-184 | 91742-10-8 | HA-1004 |
| E2 | EI-233 | 103745-39-7 | HA-1077 |

TABLE 3-continued

AlphaNumeric Well Label and the Corresponding Catalog#, CAS#, and Compound Name or ID Number for the BIOMOL Kinase Inhibitor compound library

| PLATE LOCATION | CATALOG # | CAS # | COMPOUND NAME OR ID NUMBER |
|---|---|---|---|
| E3 | EI-232 | | HDBA (2-Hydroxy-5-(2,5-dihydroxybenzylamino)benzoic acid) |
| E4 | EI-230 | 127191-97-3 | KN-62 |
| E5 | EI-268 | | KN-93 |
| E6 | EI-197 | 109376-83-2 | ML-7 |
| E7 | EI-153 | 105637-50-1 | ML-9 |
| E8 | CC-100 | 452-06-2 | 2-Aminopurine |
| E9 | CC-202 | 158982-15-1 | N9-Isopropyl-olomoucine |
| E10 | CC-200 | 101622-51-9 | Olomoucine |
| E11 | CC-201 | 101622-50-8 | iso-Olomoucine |
| E12 | CC-205 | 186692-46-6 | Roscovitine |
| F1 | EI-293 | 24386-93-4 | 5-Iodotubercidin |
| F2 | EI-295 | 62004-35-7 | LFM-A13 |
| F3 | EI-294 | 152121-30-7 | SB-202190 |
| F4 | EI-297 | 172889-27-9 | PP2 |
| F5 | EI-298 | 208260-29-1 | ZM 336372 |
| F6 | EI-306 | 5812-07-7 | SU 4312 |
| F7 | EI-303 | 146535-11-7 | AG-1296 |
| F8 | EI-307 | 220904-83-6 | GW 5074 |
| F9 | AC-1121 | 6865-14-1 | Palmitoyl-DL-carnitine Cl |
| F10 | EI-270 | 82-08-6 | Rottlerin |
| F11 | EI-147 | 446-72-0 | Genistein |
| F12 | ST-110 | 486-66-8 | Daidzein |
| G1 | EI-146 | 63177-57-1 | Erbstatin analog |
| G2 | AC-1142 | 6151-25-3 | Quercetin dihydrate |
| G3 | AC-1293 | | SU1498 |
| G4 | EI-357 | 4452-06-6 | ZM 449829 |
| G5 | EI-278 | 195462-67-7 | BAY 11-7082 |
| G6 | EI-231 | 53-85-0 | DRB (5,6-Dichloro-1-β-D-ribofuranosylbenzimidazole) |
| G7 | EI-273 | | HBDDE (2,2',3,3',4,4'-Hexahydroxy-1,1'-biphenyl-6,6'-dimethanol dimethyl ether) |
| G8 | EI-305 | 129-56-6 | SP 600125 |
| G9 | CC-206 | 479-41-4 | Indirubin |
| G10 | CC-207 | 160807-49-8 | Indirubin-3'-monoxime |
| G11 | EI-299 | 146986-50-7 | Y-27632 |
| G12 | EI-310 | 142273-20-9 | Kenpaullone |
| H1 | EI-328 | 121-40-4 | Terreic acid |
| H2 | EI-332 | 35943-35-2 | Triciribine |
| H3 | EI-336 | | BML-257 |
| H4 | EI-343 | | SC-514 |
| H5 | EI-344 | | BML-259 |
| H6 | EI-345 | 520-36-5 | Apigenin |
| H7 | EI-346 | | BML-265 (Erlotinib analog) |
| H8 | A-275 | 53123-88-9 | Rapamycin |

TABLE 4

The Effect of compounds of the BIOMOL Inhibitor compound library on the Expression of Insulin, glucagon, MAFA and Arx4 in Cells Expressing Markers Characteristic of the Pancreatic Endocrine Lineage

| Concentration and PubChem ID# | MAFA | Insulin | Glucagon | Arx4 |
|---|---|---|---|---|
| 0.61 μM 5330812 | 46.3 | 0.9 | 0.26 | 0.68 |
| 1.25 μM 5330812 | 209.2 | 1.3 | 0.31 | 0.66 |
| 5.0 μM 5330812 | 2909.9 | 66.3 | 4.71 | 0.92 |
| 0.61 μM 4566 | 1.0 | 1.0 | 0.77 | 0.78 |
| 1.25 μM 4566 | 0.8 | 1.1 | 0.90 | 0.78 |
| 5.0 μM 4566 | 1.0 | 1.1 | 0.96 | 0.69 |
| 0.61 μM 5330797 | 0.7 | 0.6 | 0.34 | 0.36 |
| 1.25 μM 5330797 | 1.5 | 0.8 | 0.25 | 0.37 |
| 5.0 μM 5330797 | 6.3 | 1.3 | 0.04 | 0.16 |
| 0.61 μM 73292 | 0.7 | 0.7 | 0.29 | 0.38 |
| 1.25 μM 73292 | 1.3 | 1.0 | 0.25 | 0.42 |
| 5.0 μM 73292 | 3.1 | 0.8 | 0.13 | 0.33 |
| 0.61 μM 4592 | 0.9 | 0.9 | 0.81 | 0.61 |
| 1.25 μM 4592 | 1.0 | 1.0 | 0.70 | 0.54 |
| 5.0 μM 4592 | 0.6 | 1.3 | 1.08 | 0.77 |
| 0.61 μM 160355 | 0.9 | 0.9 | 0.76 | 0.77 |
| 1.25 μM 160355 | 0.7 | 1.0 | 0.61 | 0.65 |
| 5.0 μM 160355 | 0.8 | 1.1 | 0.59 | 0.86 |
| Vehicle Treated | 1.0 | 1.0 | 1.00 | 1.00 |

TABLE 5

AlphaNumeric Well Label and the Corresponding Catalog#, and Compound Name or ID Number for the EMD Calbiochem Kinase Inhibitor compound library I

| Plate Location | Catalog# | Compound Name | Gene Induction vs. H1: MAFa |
|---|---|---|---|
| A10 | 197221 | Bcr-abl Inhibitor | 1.5 |
| A11 | 203290 | Bisindolylmaleimide I | 0.8 |
| A12 | DMSO | Control | 1.5 |
| A2 | 121767 | AG 1024 | 0.8 |
| A3 | 121790 | AGL 2043 | 0.8 |
| A4 | 124011 | Akt Inhibitor IV | 45.7 |
| A5 | 124012 | Akt Inhibitor V, Triciribine | 0.9 |
| A6 | 124018 | Akt Inhibitor VIII, Isozyme-Selective, Akti-1/2 | 1.6 |
| A7 | 124020 | Akt Inhibitor X | 1.4 |
| A8 | 521275 | PDK1/Akt/Flt Dual Pathway Inhibitor | 2.1 |
| A9 | 189404 | Aurora Kinase Inhibitor II | 1.3 |
| B10 | 317200 | DMBI | 1.9 |
| B11 | 324673 | EGFR/ErbB-2 Inhibitor | 2.4 |
| B12 | DMSO | Control | 1.9 |
| B2 | 203297 | Bisindolylmaleimide IV | 1.9 |
| B3 | 203696 | BPIQ-I | 1.6 |
| B4 | 220285 | Chelerythrine Chloride | 2.3 |
| B5 | 234505 | Compound 56 | 1.8 |
| B6 | 260961 | DNA-PK Inhibitor II | 2.0 |
| B7 | 260962 | DNA-PK Inhibitor III | 2.2 |
| B8 | 528100 | PI-103 | 1.9 |
| B9 | 266788 | Diacylglycerol Kinase Inhibitor II | 1.5 |
| C10 | 375670 | Herbimycin A, *Streptomyces* sp. | 1.3 |
| C11 | 343022 | Flt-3 Inhibitor III | 1.1 |
| C12 | DMSO | Control | 1.1 |
| C2 | 324674 | EGFR Inhibitor | 3.5 |
| C3 | 324840 | EGFR/ErbB-2/ErbB-4 Inhibitor | 0.9 |
| C4 | 343020 | Flt-3 Inhibitor | 0.6 |
| C5 | 343021 | Flt-3 Inhibitor II | 0.5 |
| C6 | 344036 | cFMS Receptor Tyrosine Kinase Inhibitor | 2.2 |
| C7 | 365250 | Gö 6976 | 1.9 |
| C8 | 365251 | Gö 6983 | 1.0 |
| C9 | 371806 | GTP-14564 | 0.7 |
| D10 | 440203 | LY 303511 | 1.7 |
| D11 | 448101 | Met Kinase Inhibitor | 2.1 |
| D12 | BLANK | | 1.7 |
| D2 | 407248 | IGF-1R Inhibitor II | 1.6 |
| D3 | 407601 | IRAK-1/4 Inhibitor | 2.2 |
| D4 | 420099 | JAK Inhibitor I | 1.4 |
| D5 | 420104 | JAK3 Inhibitor II | 2.0 |
| D6 | 420121 | JAK3 Inhibitor IV | 1.7 |
| D7 | 420126 | JAK3 Inhibitor VI | 1.9 |
| D8 | 428205 | Lck Inhibitor | 1.9 |
| D9 | 440202 | LY 294002 | 2.3 |
| E10 | 528106 | PI 3-Kg Inhibitor | 1.6 |
| E11 | 528108 | PI 3-KbInhibitor II | 1.4 |
| E12 | BLANK | | 1.6 |
| E2 | 513035 | PD 158780 | 0.8 |
| E3 | 513040 | PD 174265 | 1.0 |
| E4 | 521231 | PDGF Receptor Tyrosine Kinase Inhibitor II | 0.8 |
| E5 | 521232 | PDGF Receptor Tyrosine Kinase Inhibitor III | 1.7 |
| E6 | 521233 | PDGF Receptor Tyrosine Kinase Inhibitor IV | 5.5 |
| E7 | 521234 | PDGF RTK Inhibitor | 1.9 |
| E8 | 527450 | PKR Inhibitor | 24.6 |
| E9 | 527455 | PKR Inhibitor, Negative Control | 1.5 |
| F10 | 567805 | Src Kinase Inhibitor I | 2.3 |
| F11 | 572660 | SU11652 | 1.7 |
| F12 | DMSO | Control | 2.1 |
| F2 | 529574 | PP3 | 1.3 |
| F3 | 529581 | PP1 Analog II, 1NM-PP1 | 2.3 |
| F4 | 539652 | PKCbII/EGFR Inhibitor | 1.8 |
| F5 | 539654 | PKCb Inhibitor | 1.6 |
| F6 | 553210 | Rapamycin | 1.2 |
| F7 | 555553 | Rho Kinase Inhibitor III, Rockout | 1.7 |
| F8 | 555554 | Rho Kinase Inhibitor IV | 2.3 |
| F9 | 539648 | Staurosporine, N-benzoyl- | 11.7 |
| G10 | 658550 | AG 1295 | 1.4 |
| G11 | 658551 | AG 1296 | 1.1 |
| G12 | DMSO | Control | 1.2 |
| G2 | 574711 | Syk Inhibitor | 1.2 |
| G3 | 574712 | Syk Inhibitor II | 0.8 |
| G4 | 574713 | Syk Inhibitor III | 1.1 |

TABLE 5-continued

AlphaNumeric Well Label and the Corresponding Catalog#, and Compound Name or ID Number for the EMD Calbiochem Kinase Inhibitor compound library I

| Plate Location | Catalog# | Compound Name | Gene Induction vs. H1: MAFa |
|---|---|---|---|
| G5 | 616451 | TGF-b RI Kinase Inhibitor | 1.1 |
| G6 | 616453 | TGF-b RI Inhibitor III | 1.6 |
| G7 | 658390 | AG 9 | 1.5 |
| G8 | 658401 | AG 490 | 1.4 |
| G9 | 658440 | AG 112 | 1.4 |
| H10 | 189405 | Aurora Kinase Inhibitor III | 2.0 |
| H11 | 569397 | Staurosporine, *Streptomyces* sp. | 0.0* |
| H12 | DMSO | Control | 1.5 |
| H2 | 658552 | AG 1478 | 2.7 |
| H3 | 676480 | VEGF Receptor 2 Kinase Inhibitor I | 1.7 |
| H4 | 676481 | VEGF Receptor Tyrosine Kinase Inhibitor II | 1.0 |
| H5 | 676482 | VEGF Receptor Tyrosine Kinase Inhibitor III, KRN633 | 1.6 |
| H6 | 676485 | VEGF Receptor 2 Kinase Inhibitor II | 1.0 |
| H7 | 676487 | VEGF Receptor 2 Kinase Inhibitor III | 1.1 |
| H8 | 676489 | VEGF Receptor 2 Kinase Inhibitor IV | 2.1 |
| H9 | 260964 | DNA-PK Inhibitor V | 1.5 |

TABLE 6

AlphaNumeric Well Label, Corresponding Catalog#, and Compound # for EMD Calbiochem ® Kinase Inhibitor II compound library

| Well # | Catalog # | Compound # | |
|---|---|---|---|
| A1 | DMSO | | |
| A2 | 422706 | KN-62 | |
| A3 | 118500 | ATM Kinase Inhibitor | |
| A4 | 118501 | ATM/ATR Kinase Inhibitor | |
| A5 | 126870 | Alsterpaullone | |
| A6 | 126871 | Alsterpaullone, | 2-Cyanoethyl |
| A7 | 128125 | Aloisine A, RP107 | |
| A8 | 128135 | Aloisine, RP106 | |
| A9 | 164640 | Aminopurvalanol A | |
| A10 | 171260 | AMPK Inhibitor, | Compound C |
| A11 | 189405 | Aurora Kinase Inhibitor III | |
| A12 | BLANK | | |
| B1 | DMSO | | |
| B2 | 189406 | Aurora Kinase/Cdk Inhibitor | |
| B3 | 402085 | Indirubin-3'-monoxime | |
| B4 | 196870 | BAY 11-7082 | |
| B5 | 203600 | Bohemine | |
| B6 | 217695 | Cdk1 Inhibitor | |
| B7 | 217696 | Cdk1 Inhibitor, | CGP74514A |
| B8 | 217714 | Cdk1/2 Inhibitor III | |
| B9 | 217720 | Cdk1/5 Inhibitor | |
| B10 | 218696 | Casein Kinase I Inhibitor, D4476 | |
| B11 | 218710 | Casein Kinase II Inhibitor III, TBCA | |
| B12 | BLANK | | |
| C1 | DMSO | | |
| C2 | 219476 | Cdk4 Inhibitor | |
| C3 | 219477 | Cdk4 Inhibitor II, | NSC 625987 |
| C4 | 219478 | Cdk4 Inhibitor III | |
| C5 | 219479 | Cdc2-Like Kinase Inhibitor, TG003 | |
| C6 | 220486 | Chk2 Inhibitor II | |
| C7 | 234503 | Compound 52 | |
| C8 | 238803 | Cdk2 Inhibitor III | |
| C9 | 238804 | Cdk2 Inhibitor IV, | NU6140 |
| C10 | 219491 | Cdk/Crk Inhibitor | |
| C11 | 328009 | ERK Inhibitor III | |
| C12 | BLANK | | |
| D1 | DMSO | | |
| D2 | 688000 | ROCK Inhibitor, Y-27632 | |
| D3 | 328007 | ERK Inhibitor II, FR180204 | |
| D4 | 328008 | ERK Inhibitor II, | Negative control |
| D5 | 341251 | Fascaplysin, Synthetic | |
| D6 | 361540 | GSK-3b Inhibitor I | |
| D7 | 361541 | GSK-3b Inhibitor II | |
| D8 | 361549 | GSK-3b Inhibitor VIII | |

TABLE 6-continued

AlphaNumeric Well Label, Corresponding Catalog#, and Compound # for EMD Calbiochem ® Kinase Inhibitor II compound library

| Well # | Catalog # | Compound # | |
|---|---|---|---|
| D9 | 361550 | GSK-3 Inhibitor IX | |
| D10 | 361551 | GSK-3 Inhibitor X | |
| D11 | 361553 | GSK-3b Inhibitor XI | |
| D12 | BLANK | | |
| E1 | DMSO | | |
| E2 | 572635 | SU6656 | |
| E3 | 361555 | GSK-3 Inhibitor XIII | |
| E4 | 371957 | Isogranulatimide | |
| E5 | 400090 | IC261 | |
| E6 | 401481 | IKK-2 Inhibitor IV | |
| E7 | 402081 | Indirubin Derivative E804 | |
| E8 | 420119 | JNK Inhibitor II | |
| E9 | 420123 | JNK Inhibitor, | Negative Control |
| E10 | 420129 | JNK Inhibitor V | |
| E11 | 420136 | JNK Inhibitor IX | |
| E12 | BLANK | | |
| F1 | DMSO | | |
| F2 | 475863 | MK2a Inhibitor | |
| F3 | 420135 | JNK Inhibitor VIII | |
| F4 | 420298 | K-252a, *Nocardiopsis* sp. | |
| F5 | 422000 | Kenpaullone | |
| F6 | 422708 | KN-93 | |
| F7 | 444937 | MEK Inhibitor I | |
| F8 | 444938 | MEK Inhibitor II | |
| F9 | 444939 | MEK1/2 Inhibitor | |
| F10 | 454861 | MNK1 Inhibitor | |
| F11 | 481406 | NF-κB Activation Inhibitor | |
| F12 | BLANK | | |
| G1 | DMSO | | |
| G2 | 506121 | p38 MAP Kinase Inhibitor III | |
| G3 | 506126 | p38 MAP Kinase Inhibitor | |
| G4 | 513000 | PD 98059 | |
| G5 | 513030 | PD 169316 | |
| G6 | 559396 | SB220025 | |
| G7 | 540500 | Purvalanol A | |
| G8 | 361554 | GSK3b Inhibitor XII, TWS119 | |
| G9 | 371963 | H-89, Dihydrochloride | |
| G10 | 559387 | SB 202474, Negative control for p38 MAPK inhibition studies | |
| G11 | 559388 | SB 202190 | |
| G12 | BLANK | | |
| H1 | DMSO | | |
| H2 | 559389 | SB 203580 | |
| H3 | 371970 | HA 1077, Dihydrochloride | Fasudil |
| H4 | 559402 | SB 218078 | |
| H5 | 565625 | SC-68376 | |
| H6 | 567305 | SKF-86002 | |
| H7 | 567731 | Sphingosine Kinase Inhibitor | |
| H8 | 569397 | Staurosporine, *Streptomyces* sp. | |
| H9 | 570250 | STO-609 | |
| H10 | 572650 | SU9516 | |
| H11 | 616373 | Tpl2 Kinase Inhibitor | |
| H12 | BLANK | | |

TABLE 7

Fold Induction of MAFA expression by several Compounds from the EMD Kinase Inhibitor Library II on Cells Treated according to the Differentiation Protocol Outlined in Example 9

| well# | fold vs. control | cat# | drug name |
|---|---|---|---|
| A6 | 24.8 | 126871 | Alsterpaullone, 2-Cyanoethyl |
| H10 | 18.0 | 572650 | SU9516 |
| A5 | 15.3 | 126870 | Alsterpaullone |
| B8 | 8.2 | 217714 | Cdk1/2 Inhibitor III |
| B10 | 5.7 | 218696 | Casein Kinase I Inhibitor, D4476 |
| F9 | 4.92 | 444939 | MEK1/2 Inhibitor |

What is claimed is:

1. A method for increasing the expression of insulin and MAFA in cells expressing markers characteristic of the pancreatic endocrine lineage, the method comprising the steps of:
  a. sequentially differentiating human pluripotent stem cells to obtain cells expressing markers characteristic of the pancreatic endocrine lineage;
  b. culturing the cells expressing markers characteristic of the pancreatic endocrine lineage in medium comprising an added amount of a cyclin-dependant kinase inhibitor to cause an increase in expression of insulin and MAFA as compared to cells expressing markers characteristic of the pancreatic endocrine lineage that are not cultured in medium comprising the added cyclin-dependent kinase inhibitor;

wherein the cyclin-dependent kinase inhibitor is Ethyl-(6-hydroxy-4-phenylbenzo[4,5]furo[2,3-b])pyridine-3-carboxylate.

2. The method of claim 1, wherein the ethyl-(6-hydroxy-4-phenylbenzo[4,5]furo[2,3-b])pyridine-3-carboxylate is added to cells expressing markers characteristic of the endocrine lineage at a concentration from about 0.1 µM to about 10 µM for about one to seven days.

* * * * *